United States Patent [19]
Kojima et al.

[11] Patent Number: 5,389,626
[45] Date of Patent: Feb. 14, 1995

[54] 3-ARYLOXMETHYL-CEPHALOSPORIN DERIVATIVES, AND THEIR MEDICAL USE

[75] Inventors: Koichi Kojima; Kazuo Koyama; Shigeo Amemiya; Masayuki Iwata, all of Hiromachi, Japan

[73] Assignee: Sankyo Company, Limited, Tokyo, Japan

[21] Appl. No.: 880,295

[22] Filed: May 5, 1992

Related U.S. Application Data

[63] Continuation of Ser. No. 742,091, Aug. 2, 1991, abandoned, which is a continuation of Ser. No. 416,923, Oct. 4, 1989, abandoned.

[30] Foreign Application Priority Data

Oct. 7, 1988 [JP] Japan .................. 63-253253

[51] Int. Cl.$^6$ ............... C07D 501/26; A61K 31/545
[52] U.S. Cl. .................... 514/202; 540/222
[58] Field of Search ........... 514/201, 202; 540/222, 540/221

[56] References Cited

U.S. PATENT DOCUMENTS

| | | | |
|---|---|---|---|
| 4,535,156 | 8/1985 | Blumbach et al. | 540/222 |
| 4,912,212 | 3/1990 | Ochiai et al. | |
| 4,918,070 | 4/1990 | Nakagawa et al. | 540/221 |
| 4,992,431 | 2/1991 | Heyms et al. | 540/222 |
| 5,112,967 | 5/1992 | Keith et al. | 540/215 |

FOREIGN PATENT DOCUMENTS 60-41681  3/1985  Japan .
62-33185  2/1987  Japan .

OTHER PUBLICATIONS

Chemical Abstracts vol. 177:7704(a) 1992.
Chemical Abstracts vol. 115:158830l(1991).
Chemical Abstracts vol. 113:152140k (1989).
Chemical Abstracts vol. 107:115432n (1987).
Hiroshi Sadaki et al, "Studies on β-Lactam Antibiotics for Medicinal Purpose. XVIII. Synthesis and Structure–Activity Relationships of 7β-[(Z)-2-(2-Aminothiazol-4-yl)-2-methoxyimino-acetamido]-3-substituted Methyl-3-cephem-4-carboxlic Acid Derivatives", *Yakugaku Zasshi*, 106(2), 129-146, (1986), Japan. *Chemical Abstracts*, 107, 612 (1987) 107:115432n.

*Primary Examiner*—Nicholas S. Rizzo
*Attorney, Agent, or Firm*—Frishauf, Holtz, Goodman & Woodward

[57] ABSTRACT

Compounds of formula (I):

in which: $R^1$ is hydrogen or acyl; $R^2$ is hydrogen or $C_1$–$C_4$ alkoxy; and Ar is phenyl or substituted phenyl and pharmaceutically acceptable salts and esters thereof have valuable antibiotic activity, including against Methicillin-resistant strains of Staphylococcus. The invention also provides a process for preparing the compounds and methods and compositions using them.

21 Claims, No Drawings

3-ARYLOXMETHYL-CEPHALOSPORIN DERIVATIVES, AND THEIR MEDICAL USE

This application is a continuation of application Ser. No. 07/742,091, filed Aug. 2, 1991, now abandoned; which is a continuation of Ser. No. 07/416,923, filed Oct. 4, 1989, (abandoned).

BACKGROUND TO THE INVENTION

The present invention relates to a series of new cephalosporin derivatives having an aryloxymethyl, more specifically an optionally substituted phenoxymethyl, group at the 3-position and having an amino or optionally substituted acylamino group at the 7-position. These compounds are cephalosporin antibiotics or are precursors in the preparation of cephalosporin antibiotics having a wide spectrum of antibacterial activity. The invention also provides a method for preparing these new compounds and processes and compositions using them.

Since the first discovery of the cephalosporin family of antibiotics, which really began in the 1950's, considerable interest has been shown in this range of antibiotics and many of them have been found to be of considerable practical use in the treatment of microbial infections. The earliest members of the cephalosporin family to find practical use, which might be termed "the first generation", started to become generally available in the 1970's and are typified by Cefazolin. These antibiotics were extremely good for their time but were and are susceptible to microorganisms capable of producing β-lactamase, and these microorganisms were thus resistant to them, with the result that the value of the first generation cephalosporin antibiotics decreased with time. The next group of cephalosporin antibiotics, which may be termed "the second generation", overcame this problem of resistance by microorganisms which produce β-lactamase and are typified by Cefmetazole and Cefothiam. In recent years, we have seen the emergence of a third generation of cephalosporin antibiotics, which are distinguished from the second generation by their broader antibacterial spectrum of activity, especially against Gram-negative bacteria. Many hopes are pinned on this third generation, most particularly to find an antibiotic which is active against Methicillin-resistant strains of Staphylococcus, which have been the cause of many deaths, especially in hospitals, and much difficulty and distress for patients and medical practitioners. Hitherto, so far as we are, at the time of writing, aware, this search has proved fruitless.

We have now surprisingly found a series of cephalosporin derivatives which have a wide spectrum of antibacterial activity and to which, quite unexpectedly, Methicillin-resistant strains of Staphylococcus appear to be susceptible. The compounds are also believed to have a sufficiently low toxicity to humans and other animals that it is expected that they will find practical therapeutic use. The compounds of the present invention are characterised by the presence of an optionally substituted phenoxymethyl group at the 3-position.

Surprisingly, compounds having such an optionally substituted phenoxymethyl group at the 3-position do not appear to have been disclosed in the past, although such compounds are covered by general references to a wide range of groups at the 3-position in a number of prior patents, for example Japanese Patent Application No. Kokai (i.e. as laid open to public inspection prior to examination) No. Sho. 60-41681. However, it appears to be the presence of this group that leads to the unexpected activity of the compounds of the present invention.

BRIEF SUMMARY OF THE INVENTION

It is, therefore, an object of the present invention to provide a series of new cephalosporin derivatives, which are characterised by the presence of an optionally substituted phenoxymethyl group at the 3-position, and which are, or are precursors of, a range of highly active antibiotics.

It is a further object of the present invention to provide a pharmaceutical composition containing such cephalosporin antibiotics and to provide a method of using such cephalosporin antibiotics for the treatment or prophylaxis of bacterial infections.

Other objects and advantages of the present invention will become apparent as the description proceeds.

The compounds of the invention are cephalosporin derivatives having the formula (I):

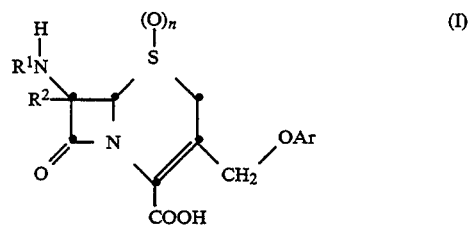

in which:

$R^1$ represents a hydrogen atom or an acyl group selected from the group consisting of: $C_1$-$C_{10}$ alkanoyl groups; substituted $C_1$-$C_{10}$ alkanoyl groups having at least one substituent selected from the group consisting of substituents (a), defined below; $C_3$-$C_{10}$ alkenoyl groups; substituted $C_3$-$C_{10}$ alkenoyl groups having at least one substituent selected from the group consisting of substituents (a), defined below; $C_3$-$C_6$ alkynoyl groups; carbocyclic aromatic carboxylic acyl groups having from 7 to 11 carbon atoms which are unsubstituted or have at least one substituent selected from the group consisting of substituents (b), defined below; groups of formula Het—CO— in which Het represents a heterocyclic group having from 4 to 7 ring atoms of which from 1 to 4 are hetero-atoms selected from the group consisting of nitrogen, oxygen and sulfur hetero-atoms, which heterocyclic group is unsubstituted or has at least one substituent selected from the group consisting of substituents (c), defined below; and cycloalkyl-carbonyl groups in which the cycloalkyl part has from 3 to 7 ring carbon atoms and is unsubstituted or has at least one substituent selected from the group consisting of substituents (b), defined below;

$R^2$ represents a hydrogen atom or a $C_1$-$C_4$ alkoxy group; and

Ar represents a phenyl group or a substituted phenyl group having at least one substituent selected from the group consisting of substituents (b), defined below;

substituents (a):

$C_1$-$C_6$ alkoxy groups; $C_1$-$C_6$ alkylthio groups; substituted $C_1$-$C_6$ alkoxy groups having at least one substituent selected from the group consisting of substituents (d), defined below; substituted $C_1$-$C_6$ alkylthio groups having at least one substituent selected from the group consisting of substituents (d), defined below; groups of formula Het—O—, in which Het is as defined above; groups of formula Het—S—, in which Het is as defined above; aryloxy groups in which the aryl part is $C_6$-$C_{10}$ and is unsubstituted or has at least one substituent selected from the group consisting of substituents (e), defined below; arylthio groups in which the aryl part is $C_6$-$C_{10}$ and is unsubstituted or has at least one substituent selected from the group consisting of substituents (e), defined below; amino groups; mono- and di- alkylamino groups in which the or each alkyl part has from 1 to 6 carbon atoms; carbamoyl groups; mono- and di- alkylcarbamoyl groups in which the or each alkyl part has from 1 to 6 carbon atoms; carboxy groups; $C_2$-$C_{11}$ alkoxycarbonyl groups; aryloxycarbonyl groups in which the aryl part is $C_6$-$C_{10}$ and is unsubstituted or has at least one substituent selected from the group consisting of substituents (e), defined below; aralkyloxycarbonyl groups in which the alkyl part is $C_1$-$C_4$ and the or each aryl part is $C_6$-$C_{10}$ and is unsubstituted or has at least one substituent selected from the group consisting of substituents (e), defined below; $C_1$-$C_6$ aliphatic carboxylic acyl groups; substituted $C_1$-$C_6$ aliphatic carboxylic acyl groups having at least one substituent selected from the group consisting of substituents (f), defined below; carbocyclic aromatic carboxylic acyl groups in which the aryl part is $C_6$-$C_{10}$ and is unsubstituted or has at least one substituent selected from the group consisting of substituents (e), defined below; $C_1$-$C_6$ aliphatic carboxylic acyloxy groups; substituted $C_1$-$C_6$ aliphatic carboxylic acyloxy groups having at least one substituent selected from the group consisting of substituents (f), defined below; carbocyclic aromatic carboxylic acyloxy groups in which the aryl part is $C_6$-$C_{10}$ and is unsubstituted or has at least one substituent selected from the group consisting of substituents (e), defined below; groups of formula Het—CO—O—, in which Het is as defined above; groups of formula Het—CO—NH—, in which Het is as defined above; $C_1$-$C_6$ aliphatic carboxylic acylamino groups; substituted $C_1$-$C_6$ aliphatic carboxylic acylamino groups having at least one substituent selected from the group consisting of substituents (f), defined below; aromatic carboxylic acylamino groups in which the aryl part is $C_6$-$C_{10}$ carbocyclic and is unsubstituted or has at least one substituent selected from the group consisting of substituents (e), defined below; $C_1$-$C_6$ alkylsulfinyl groups; $C_1$-$C_6$ alkylsulfonyl groups; arylsulfinyl groups in which the aryl part is $C_6$-$C_{10}$ carbocyclic and is unsubstituted or has at least one substituent selected from the group consisting of substituents (e), defined below; arylsulfonyl groups in which the aryl part is $C_6$-$C_{10}$ carbocyclic and is unsubstituted or has at least one substituent selected from the group consisting of substituents (e), defined below; nitro groups; cyano groups; halogen atoms; hydroxy groups; mercapto groups; groups of formula =$NOR^3$; heterocyclic groups having from 5 to 7 ring atoms of which from 1 to 4 are hetero-atoms selected from the group consisting of nitrogen, oxygen and sulfur hetero-atoms and being unsubstituted or having at least one substituent selected from the group consisting of substituents (c), defined below; $C_6$-$C_{10}$ carbocyclic aryl groups which are unsubstituted or have at least one substituent selected from the group consisting of substituents (e), defined below; sulfo groups; cycloaliphatic hydrocarbon groups having from 5 to 7 ring carbon atoms and one or two carbon-carbon double bonds; and cycloalkyl groups having from 3 to 7 ring carbon atoms;

$R^3$ represents: a hydrogen atom; a $C_1$-$C_6$ alkyl group; a substituted $C_1$-$C_6$ alkyl group having at least one substituent selected from the group consisting of substituents (g), defined below; a $C_2$-$C_6$ alkenyl group; a $C_2$-$C_6$ alkynyl group; an aralkyl group in which the alkyl part is $C_1$-$C_4$ and the group has from 1 to 3 aryl parts, each of which is $C_6$, or has one aryl part which is $C_6$-$C_{14}$, said aryl part or parts being unsubstituted or having at least one substituent selected from the group consisting of substituents (e), defined below; a $C_3$-$C_7$ cycloalkyl group; a $C_1$-$C_6$ aliphatic carboxylic acyl group; a substituted $C_1$-$C_6$ aliphatic carboxylic acyl group having at least one substituent selected from the group consisting of substituents (f), defined below; an aromatic carboxylic acyl group in which the aryl part is $C_6$-$C_{10}$ carbocyclic and is unsubstituted or has at least one substituent selected from the group consisting of substituents (e), defined below; a group of formula Het—CO— in which Het is as defined above; a $C_2$-$C_{11}$ alkoxycarbonyl group; a $C_4$-$C_8$ cycloalkoxycarbonyl group; an aryloxycarbonyl group in which the aryl part is $C_6$-$C_{10}$ carbocyclic and is unsubstituted or has at least one substituent selected from the group consisting of substituents (e), defined below; an aralkyloxycarbonyl group in which the alkyl part is $C_1$-$C_4$ and the or each aryl part is $C_6$-$C_{10}$ carbocyclic and is unsubstituted or has at least one substituent selected from the group consisting of substituents (e), defined below; a heterocyclic group having from 5 to 7 ring atoms of which from 1 to 4 are hetero-atoms selected from the group consisting of nitrogen, oxygen and sulfur hetero-atoms, said heterocyclic group being monocyclic or being fused to a benzene ring or to another such heterocyclic group and being unsubstituted or having at least one substituent selected from the group consisting of substituents (c), defined below; a phthalidyl group which is unsubstituted or has at least one substituent selected from the group consisting of substituents (e), defined below; a carbamoyl group; or a mono- or di- alkylcarbamoyl group in which the or each alkyl part has from 1 to 6 carbon atoms;

substituents (b):

$C_1$-$C_6$ alkyl groups; $C_1$-$C_6$ alkoxy groups; $C_1$-$C_6$ alkylthio groups; substituted $C_1$-$C_6$ alkyl groups having at least one substituent selected from the group consisting of substituents (f), defined below; substituted $C_1$-$C_6$ alkoxy groups having at least one substituent selected from the group consisting of substituents (f), defined below; substituted $C_1$-$C_6$ alkylthio groups having at least one substituent selected from the group consisting of substituents (f), defined below; $C_2$-$C_6$ alkenyl groups; $C_2$-$C_6$ alkynyl groups; aralkyloxy groups in which the alkyl part is $C_1$-$C_4$ and the or each aryl part is $C_6$-$C_{10}$ carbocyclic and is unsubstituted or has at least one substituent selected from the group consisting of substituents (h), defined below; amino groups; mono- and di- alkylamino groups in which the or each alkyl part has from 1 to 6 carbon atoms; carbamoyl groups; mono- and di- alkylcarbamoyl groups in which the or each alkyl part has from 1 to 6 carbon atoms; carboxy groups; $C_2$-$C_{11}$ alkoxycarbonyl groups; $C_2$-$C_{11}$ alkoxycarbonyloxy groups; aryloxycarbonyl groups in which the aryl part is $C_6$-$C_{10}$ carbocyclic and is unsubstituted or has at least one substituent selected from the group consisting of substituents (h), defined below; aryloxycarbonyloxy groups in which the aryl part is $C_6$-$C_{10}$ carbocyclic and is unsubstituted or has at least one substituent selected from the group consisting of substituents (h), defined below; aralkyloxycarbonyl groups in which the alkyl part is $C_1$-$C_4$ and the or each aryl part is $C_6$-$C_{10}$ carbocyclic and is unsubstituted or has at least one substituent selected from the group consisting of substituents (h), defined below; aralkyloxycarbonyloxy groups in which the alkyl part is $C_1$-$C_4$ and the or each aryl part is $C_6$-$C_{10}$ carbocyclic and is unsubstituted or has at least one substituent selected from the group consisting of substituents (h), defined below; $C_1$-$C_6$ aliphatic carboxylic acyl groups; substituted $C_1$-$C_6$ aliphatic carboxylic acyl groups having at least one substituent selected from the group consisting of substituents (f), defined below; aromatic carboxylic acyl groups in which the aryl part is $C_6$-$C_{10}$ carbocyclic and is unsubstituted or has at least one substituent selected from the group consisting of substituents (h), defined below; $C_1$-$C_6$ aliphatic carboxylic acyloxy groups; substituted $C_1$-$C_6$ aliphatic carboxylic acyloxy groups having at least one substituent selected from the group consisting of substituents (f), defined below; aromatic carboxylic acyloxy groups in which the aryl part is $C_6$-$C_{10}$ carbocyclic and is unsubstituted or has at least one substituent selected from the group consisting of substituents (h), defined below; $C_1$-$C_6$ aliphatic carboxylic acylamino groups; substituted $C_1$-$C_6$ aliphatic carboxylic acylamino groups having at least one substituent selected from the group consisting of substituents (f), defined below; aromatic carboxylic acylamino groups in which the aryl part is $C_6$-$C_{10}$ carbocyclic and is unsubstituted or has at least one substituent selected from the group consisting of substituents (h), defined below; $C_1$-$C_6$ alkylsulfinyl groups; $C_1$-$C_6$ alkylsulfonyl groups; $C_1$-$C_6$ alkylsulfonylamino groups; arylsulfinyl groups in which the aryl part is $C_6$-$C_{10}$ carbocyclic and is unsubstituted or has at least one substituent selected from the group consisting of substituents (h), defined below; arylsulfonyl groups in which the aryl part is $C_6$-$C_{10}$ carbocyclic and is unsubstituted or has at least one substituent selected from the group consisting of substituents (h), defined below; sulfo groups; arylsulfonylamino groups in which the aryl part is $C_6$-$C_{10}$ carbocyclic and is unsubstituted or has at least one substituent selected from the group consisting of substituents (h), defined below; $C_1$-$C_4$ alkylene groups; $C_1$-$C_3$ alkylenedioxy groups; nitro groups; cyano groups; halogen atoms; hydroxy groups; and mercapto groups;

substituents (c):
oxygen atoms (to form an oxo group); $C_1$-$C_6$ alkyl groups; hydroxy groups; mercapto groups; $C_1$-$C_6$ alkoxy groups; $C_1$-$C_6$ alkylthio groups: amino groups; mono- and di- alkylamino groups in which the or each alkyl part has from 1 to 6 carbon atoms; mono- and di- alkylcarbamoyl groups in which the or each alkyl part has from 1 to 6 carbon atoms; $C_1$-$C_6$ alkylidene groups; substituted $C_1$-$C_6$ alkylidene groups having at least one substituent selected from the group consisting of substituents (i), defined below; $C_1$-$C_6$ aliphatic carboxylic acyl groups; substituted $C_1$-$C_6$ aliphatic carboxylic acyl groups having at least one substituent selected from the group consisting of substituents (d), defined above; aromatic carboxylic acyl groups in which the aryl part is $C_6$-$C_{10}$ carbocyclic and is unsubstituted or has at least one substituent selected from the group consisting of substituents (e), defined above; $C_1$-$C_6$ aliphatic carboxylic acyloxy groups; substituted $C_1$-$C_6$ aliphatic carboxylic acyloxy groups having at least one substituent selected from the group consisting of substituents (d), defined above; aromatic carboxylic acyloxy groups in which the aryl part is $C_6$-$C_{10}$ carbocyclic and is unsubstituted or has at least one substituent selected from the group consisting of substituents (e), defined above; $C_1$-$C_6$ alkylthio groups; substituted $C_1$-$C_6$ alkylthio groups having at least one substituent selected from the group consisting of substituents (d), defined below; arylthio groups in which the aryl part is $C_6$-$C_{10}$ and is unsubstituted or has at least one substituent selected from the group consisting of substituents (e), defined below; $C_1$-$C_6$ alkylsulfinyl groups; $C_1$-$C_6$ alkylsulfonyl groups; arylsulfinyl groups in which the aryl part is $C_6$-$C_{10}$ carbocyclic and is unsubstituted or has at least one substituent selected from the group consisting of substituents (e), defined below; arylsulfonyl groups in which the aryl part is $C_6$-$C_{10}$ carbocyclic and is unsubstituted or has at least one substituent selected from the group consisting of substituents (e), defined below; mono- and di- alkylsulfamoyl groups in which the or each alkyl part has from 1 to 6 carbon atoms; and sulfo groups;

substituents (d):
halogen atoms, cyano groups, amino groups, mono- and di- alkylamino groups in which the or each alkyl part has from 1 to 6 carbon atoms, carboxy groups, $C_2$-$C_7$ alkoxycarbonyl groups, aryloxycarbonyl groups in which the aryl part is $C_6$-$C_{10}$ carbocyclic and is unsubstituted or has at least one substituent selected from the group consisting of substituents (e), defined below, and aralkyloxycarbonyl groups in which the alkyl part is $C_1$-$C_4$ and the or each aryl part is $C_6$-$C_{10}$ carbocyclic and is unsubstituted or has at least one substituent selected from the group consisting of substituents (e), defined below;

substituents (e):
hydroxy groups, $C_1$-$C_6$ alkyl groups, $C_1$-$C_6$ alkoxy groups, $C_1$-$C_6$ aminoalkyl groups, nitro groups, cyano groups and halogen atoms;

substituents (f):
$C_1$-$C_6$ alkoxy groups; $C_1$-$C_6$ alkylthio groups; substituted $C_1$-$C_6$ alkylthio groups having at least one substituent selected from the group consisting of amino groups and mono- and di- alkylamino groups in which the or each alkyl part is $C_1$-$C_6$; amino groups; mono- and di- alkylamino groups in which the or each alkyl part has from 1 to 6 carbon atoms; carbamoyl groups; mono- and di- alkylcarbamoyl groups in which the or each alkyl part has from 1 to 6 carbon atoms; carboxy groups; $C_2$-$C_7$ alkoxycarbonyl groups; aryloxycarbonyl groups in which the aryl part is $C_6$-$C_{10}$ carbocyclic and is unsubstituted or has at least one substituent selected from the group consisting of substituents (e), defined above; aralkyloxycarbonyl groups in which the alkyl part is $C_1$-$C_4$ and the or each aryl part is $C_6$-$C_{10}$ carbocyclic and is unsubstituted or has at least one substituent selected from the group consisting of substituents (e), defined above; $C_1$-$C_6$ aliphatic carboxylic acyl groups; substituted $C_1$-$C_6$ aliphatic carboxylic acyl groups having at least one substituent selected from the group consisting of substituents (d), defined above; aromatic carboxylic acyl groups in which the aryl part is $C_6$-$C_{10}$ carbocyclic and is unsubstituted or has at least one substituent selected from the group consisting of substituents (e), defined above; $C_1$-$C_6$ aliphatic carboxylic acyloxy groups; substituted $C_1$-$C_6$ aliphatic carboxylic acyloxy groups having at least one substituent selected from the group consisting of substituents (d), defined above; aromatic carboxylic acyloxy groups in which the aryl part is $C_6$-$C_{10}$ carbocyclic and is unsubstituted or has at least one substituent selected from the group consisting of substituents (e), defined above; sulfo groups; $C_1$-$C_6$ alkylsulfinyl groups; $C_1$-$C_6$ alkylsulfonyl groups; arylsulfinyl groups in which the aryl part is $C_6$-$C_{10}$ carbocyclic and is unsubstituted or has at least one substituent selected from the group consisting of substituents (e), defined above; arylsulfonyl groups in which the aryl part is $C_6$-$C_{10}$ carbocyclic and is unsubstituted or has at least one substituent selected from the group consisting of substituents (e), defined above; nitro groups; cyano groups; halogen atoms; hydroxy groups; and mercapto groups;

substituents (g):

halogen atoms; carboxy groups; $C_2$-$C_7$ alkoxycarbonyl groups; substituted $C_2$-$C_7$ alkoxycarbonyl groups having at least one substituent selected from the group consisting of substituents (d), defined above; aryloxycarbonyl groups in which the aryl part is $C_6$-$C_{10}$ carbocyclic and is unsubstituted or has at least one substituent selected from the group consisting of substituents (e), defined above; aralkyloxycarbonyl groups in which the alkyl part is $C_1$-$C_4$ and the or each aryl part is $C_6$-$C_{10}$ carbocyclic and is unsubstituted or has at least one substituent selected from the group consisting of substituents (e), defined above; $C_2$-$C_7$ alkoxycarbonyloxy groups; substituted $C_2$-$C_7$ alkoxycarbonyloxy groups having at least one substituent selected from the group consisting of substituents (d), defined above; aryloxycarbonyloxy groups in which the aryl part is $C_6$-$C_{10}$ carbocyclic and is unsubstituted or has at least one substituent selected from the group consisting of substituents (e), defined above; aralkyloxycarbonyloxy groups in which the alkyl part is $C_1$-$C_4$ and the or each aryl part is $C_6$-$C_{10}$ carbocyclic and is unsubstituted or has at least one substituent selected from the group consisting of substituents (e), defined above; heterocyclic groups having from 5 to 7 ring atoms of which from 1 to 4 are hetero-atoms selected from the group consisting of nitrogen, oxygen and sulfur hetero-atoms, said heterocyclic group being monocyclic or being fused to a benzene ring or to another such heterocyclic group and being unsubstituted or having at least one substituent selected from the group consisting of substituents (c), defined above; $C_1$-$C_6$ alkylthio groups; substituted $C_1$-$C_6$ alkylthio groups having at least one substituent selected from the group consisting of substituents (d), defined above; arylthio groups in which the aryl part is $C_6$-$C_{10}$ and is unsubstituted or has at least one substituent selected from the group consisting of substituents (e), defined below; $C_1$-$C_6$ alkylsulfinyl groups; $C_1$-$C_6$ alkylsulfonyl groups; arylsulfinyl groups in which the aryl part is $C_6$-$C_{10}$ carbocyclic and is unsubstituted or has at least one substituent selected from the group consisting of substituents (e), defined below; arylsulfonyl groups in which the aryl part is $C_6$-$C_{10}$ carbocyclic and is unsubstituted or has at least one substituent selected from the group consisting of substituents (e), defined below; mono- and di- alkylsulfamoyl groups in which the or each alkyl part has from 1 to 6 carbon atoms; sulfo groups; carbamoyl groups; mono- and di- alkylcarbamoyl groups in which the or each alkyl part has from 1 to 6 carbon atoms; amino groups; mono- and di- alkylamino groups in which the or each alkyl part has from 1 to 6 carbon atoms; $C_3$-$C_7$ cycloalkyl groups; and $C_6$-$C_{10}$ carbocyclic aryl groups which are unsubstituted or have at least one substituent selected from the group consisting of substituents (e), defined above;

substituents (h):

$C_1$-$C_6$ alkyl groups; $C_1$-$C_6$ alkoxy groups; $C_1$-$C_6$ alkylthio groups; amino groups; mono- and di- alkylamino groups in which the or each alkyl part has from 1 to 6 carbon atoms: carbamoyl groups; mono- and di- alkylcarbamoyl groups in which the or each alkyl part has from 1 to 6 carbon atoms; carboxy groups; $C_2$-$C_7$ alkoxycarbonyl groups; aryloxycarbonyl groups in which the aryl part is $C_6$-$C_{10}$ carbocyclic and is unsubstituted or has at least one substituent selected from the group consisting of substituents (e), defined above; aralkyloxycarbonyl groups in which the alkyl part is $C_1$-$C_4$ and the or each aryl part is $C_6$-$C_{10}$ carbocyclic and is unsubstituted or has at least one substituent selected from the group consisting of substituents (e), defined above; $C_1$-$C_6$ aliphatic carboxylic acyl groups; substituted $C_1$-$C_6$ aliphatic carboxylic acyl groups having at least one substituent selected from the group consisting of substituents (d), defined above; aromatic carboxylic acyl groups in which the aryl part is $C_6$-$C_{10}$ carbocyclic and is unsubstituted or has at least one substituent selected from the group consisting of substituents (e), defined above; $C_1$-$C_6$ aliphatic carboxylic acyloxy groups; substituted $C_1$-$C_6$ aliphatic carboxylic acyloxy groups having at least one substituent selected from the group consisting of substituents (d), defined above; aromatic carboxylic acyloxy groups in which the aryl part is $C_6$-$C_{10}$ carbocyclic and is unsubstituted or has at least one substituent selected from the group consisting of substituents (e), defined above; $C_1$-$C_6$ alkylsulfinyl groups: $C_1$-$C_6$ alkylsulfonyl groups; arylsulfinyl groups in which the aryl part is $C_6$-$C_{10}$ carbocyclic and is unsubstituted or has at least one substituent selected from the group consisting of substituents (e), defined above; arylsulfonyl groups in which the aryl part is $C_6$-$C_{10}$ carbocyclic and is unsubstituted or has at least one substituent selected from the group consisting of substituents (e), defined above; nitro groups; cyano groups; halogen atoms; hydroxy groups; and mercapto groups;

substituents (i):

carboxy groups, carbamoyl groups; mono- and di- alkylcarbamoyl groups in which the or each alkyl part has from 1 to 6 carbon atoms; $C_2$-$C_7$ alkoxycarbonyl groups; aryloxycarbonyl groups in which the aryl part is $C_6$-$C_{10}$ carbocyclic and is unsubstituted or has at least one substituent selected from the group consisting of substituents (e), defined above; and aralkyloxycarbonyl groups in which the alkyl part is $C_1$-$C_4$ and the or each aryl part is $C_6$-$C_{10}$ carbocyclic and is unsubstituted or has at least one substituent selected from the group consisting of substituents (e), defined above;

and pharmaceutically acceptable salts and esters thereof.

The invention also provides a pharmaceutical composition for the treatment of bacterial infections and comprising an effective amount of an antibiotic, wherein the antibiotic is selected from the group consisting of compounds of formula (I), shown above, in which $R^1$ represents said acyl group, and pharmaceutically acceptable salts and esters thereof.

The invention still further provides a method of treating an animal, preferably a mammal, which may be human, suffering from a bacterial infection (including infection by Methicillin-resistant Staphylococcus), by administering to said animal an effective amount of an antibiotic, wherein the antibiotic is selected from the group consisting of compounds of formula (I), shown above, in which $R^1$ represents said acyl group, and pharmaceutically acceptable salts and esters thereof.

DETAILED DESCRIPTION OF INVENTION

In the compounds of the present invention, Ar represents a phenyl group which may be unsubstituted or may have at least one substituent selected from the group consisting of substituents (b), defined above and exemplified below. Where Ar represents a substituted phenyl group, it may have from 1 to 5 such substituents, and, where there are two or more substituents, these may be the same or different from each other. Examples of such substituents include:

$C_1$–$C_6$ alkyl groups, which may be straight or branched chain alkyl groups containing from 1 to 6 carbon atoms, and examples include the methyl, ethyl, propyl, isopropyl, butyl, isobutyl, sec-butyl, t-butyl, pentyl, isopentyl, 2-methylbutyl, hexyl, isohexyl and 2-methylpentyl groups, of which the methyl, ethyl, propyl and butyl groups are preferred, the methyl group generally being most preferred;

$C_1$–$C_6$ alkoxy groups, which may be straight or branched chain alkoxy groups containing from 1 to 6 carbon atoms, and examples include the methoxy, ethoxy, propoxy, isopropoxy, butoxy, isobutoxy, sec-butoxy, t-butoxy, pentyloxy, isopentyloxy, 2-methylbutoxy, hexyloxy, isohexyloxy and 2-methylpentyloxy groups, of which the methoxy, ethoxy, propoxy and butoxy groups are preferred, the methoxy group generally being most preferred;

$C_1$–$C_6$ alkylthio groups, which may be straight or branched chain alkylthio groups containing from 1 to 6 carbon atoms, and examples include the methylthio, ethylthio, propylthio, isopropylthio, butylthio, isobutylthio, sec-butylthio, t-butylthio, pentylthio, isopentylthio, 2-methylbutylthio, hexylthio, isohexylthio and 2-methylpentylthio groups, of which the methylthio, ethylthio, propylthio and butylthio groups are preferred, the methylthio group generally being most preferred;

substituted $C_1$–$C_6$ alkyl, alkoxy or alkylthio groups having at least one substituent selected from the group consisting of substituents (f), defined above and exemplified below; the parent alkyl, alkoxy and alkylthio groups are as exemplified above in relation to the unsubstituted groups and the substituents are generally exemplified elsewhere; specific examples of such substituted groups include the trifluoromethyl, difluoromethyl, fluoromethyl, 2,2,2-trifluoroethyl, 2,2,2-trichloroethyl, cyanomethyl, 1-cyanoethyl, 2-cyanoethyl, 3-cyanopropyl, 3-cyanobutyl, 4-cyanobutyl, 5-cyanopentyl, 6-cyanohexyl, hydroxymethyl, 1-hydroxyethyl, 2-hydroxyethyl, 3-hydroxypropyl, 2-hydroxypropyl, 6-hydroxyhexyl, carboxymethyl, methoxycarbonylmethyl, 2-methoxycarbonylethyl, aminomethyl, 2-aminoethyl, (methylamino)methyl, (dimethylamino)methyl, 2-(dimethylamino)ethyl, (2-aminoethylthio)methyl, 2-aminoethylthio, carbamoylmethyl, 2-carbamoylethyl, 3-carbamoylpropyl, 4-carbamoylbutyl, 5-carbamoylpentyl, 6-carbamoylhexyl, (dimethylcarbamoyl)methyl, 2-(dimethylcarbamoyl)ethyl, mercaptomethyl and 2-mercaptoethyl groups and substituted alkoxy and alkylthio groups corresponding to these substituted alkyl groups;

$C_2$–$C_6$ alkenyl groups, which have from 2 to 6 carbon atoms and which may be straight or branched chain groups; examples include the vinyl, 1-propenyl, allyl, isopropenyl, methallyl, 1-butenyl, 2-butenyl, 3-butenyl, 2-propylallyl, 1-pentenyl, 2-pentenyl, 3-pentenyl, 4-pentenyl, 1-butylvinyl, 2-methyl-3-pentenyl, 4-methyl-3-pentenyl, 1-methyl-4-pentenyl, 1-hexenyl, 2-hexenyl, 3-hexenyl, 4-hexenyl, 5-hexenyl, 3-methyl-1-butenyl, 3-methyl-2-butenyl, 3-methyl-3-butenyl, 3-methyl-1-pentenyl, 3-methyl-2-pentenyl, 3-methyl-3-pentenyl, 3-methyl-4-pentenyl and 3-methyl-1-hexenyl groups, of which the vinyl, allyl, butenyl and pentenyl groups are preferred and the vinyl and allyl groups are most prefered;

$C_2$–$C_6$ alkynyl groups, which have from 2 to 6 carbon atoms and which may be straight or branched chain groups; examples include the ethynyl, 1-propynyl, 2-propynyl (i.e. propargyl), 1-butynyl, 2-butynyl, 3-butynyl, 1-methyl-2-butynyl, 1-pentynyl, 2-pentynyl, 3-pentynyl, 4-pentynyl, 1-methyl-2-pentynyl, 1-methyl-3-pentynyl, 1-hexynyl, 2-hexynyl, 3-hexynyl, 4-hexynyl, 5-hexynyl, 3-methyl-1-butynyl, 3-methyl-2-butynyl, 3-methyl-3-butynyl, 3-methyl-1-pentynyl, 3-methyl-2-pentynyl, 3-methyl-3-pentynyl, 3-methyl-4-pentynyl and 3-methyl-1-hexynyl groups, of which the ethynyl, propargyl, butynyl and pentynyl groups are preferred and the ethynyl and propargyl groups are most preferred;

aralkyloxy groups in which the alkyl part is $C_1$–$C_4$ and the or each aryl part is $C_6$–$C_{10}$ carbocyclic and is unsubstituted or has at least one substituent selected from the group consisting of substituents (h), defined above; the alkyl part may be any of those alkyl groups having from 1 to 4 carbon atoms listed above, but is preferably a methyl, ethyl or propyl group, more preferably a methyl or ethyl group and most preferably a methyl group; the aryl part is preferably a phenyl or naphthyl (1- or 2- naphthyl) group, which may be substituted or unsubstituted; and preferred aralkyloxy groups are the benzyloxy, phenethyloxy, 1-phenylethoxy, 3-phenylpropoxy, 2-phenylpropoxy, 1-phenylpropoxy and 4-phenylbutoxy groups;

amino groups;

mono- and di- alkylamino groups in which the or each alkyl part has from 1 to 6 carbon atoms, such as the methylamino, ethylamino, propylamino, isopropylamino, butylamino, isobutylamino, sec-butylamino, t-butylamino, pentylamino, isopentylamino, hexylamino, isohexylamino, dimethylamino, diethylamino, dipropylamino, diisopropylamino, dibutylamino, methylethylamino, methylpropylamino, methylbutylamino and ethylpropylamino groups;

carbamoyl groups;

mono- and di- alkylcarbamoyl groups in which the or each alkyl part has from 1 to 6 carbon atoms, such as the methylcarbamoyl, ethylcarbamoyl, propylcarbamoyl, isopropylcarbamoyl, butylcarbamoyl, isobutylcarbamoyl, sec-butylcarbamoyl, t-butylcarbamoyl, pentylcarbamoyl, isopentylcarbamoyl, hexylcarbamoyl, isohexylcarbamoyl, dimethylcarbamoyl, diethylcarbamoyl, dipropylcarbamoyl, diisopropylcarbamoyl, dibutylcarbamoyl, methylethylcarbamoyl, methylpropylcarbamoyl, methylbutylcarbamoyl and ethylpropylcarbamoyl groups;

carboxy groups;

$C_2$-$C_{11}$, preferably $C_2$-$C_7$, alkoxycarbonyl groups (i.e. the alkoxy part has from 1 to 10, preferably 1 to 6, carbon atoms and may be any of the alkoxy groups exemplified above), such as the methoxycarbonyl, ethoxycarbonyl, propoxycarbonyl, isopropoxycarbonyl, butoxycarbonyl, isobutoxycarbonyl, sec-butoxycarbonyl, t-butoxycarbonyl, 1-ethylpropoxycarbonyl, 1,1-dipropylbutoxycarbonyl, pentyloxycarbonyl, isopentyloxycarbonyl, 2-methylbutoxycarbonyl, hexyloxycarbonyl, isohexyloxycarbonyl, 2-methylpentyloxycarbonyl, heptyloxycarbonyl, octyloxycarbonyl, 2-ethylhexyloxycarbonyl, nonyloxycarbonyl and decyloxycarbonyl groups;

$C_2$-$C_{11}$ alkoxycarbonyloxy groups, preferably $C_2$-$C_7$ alkoxycarbonyloxy groups (i.e. the alkoxy part has from 1 to 10, preferably 1 to 6, carbon atoms and may be any of the alkoxy groups exemplified above), such as the methoxycarbonyloxy, ethoxycarbonyloxy, propoxycarbonyloxy, isopropoxycarbonyloxy, butoxycarbonyloxy, isobutoxycarbonyloxy, sec-butoxycarbonyloxy, t-butoxycarbonyloxy, 1-ethylpropoxycarbonyloxy, 1,1-dipropylbutoxycarbonyloxy, pentyloxycarbonyloxy, isopentyloxycarbonyloxy, 2-methylbutoxycarbonyloxy, hexyloxycarbonyloxy, isohexyloxycarbonyloxy, 2-methylpentyloxycarbonyloxy, heptyloxycarbonyloxy, octyloxycarbonyloxy, 2-ethylhexyloxycarbonyloxy, nonyloxycarbonyloxy and decyloxycarbonyloxy groups;

aryloxycarbonyl groups in which the aryl part is $C_6$-$C_{10}$ and is unsubstituted or has at least one substituent selected from the group consisting of substituents (h), defined above and exemplified below, especially the phenoxycarbonyl and naphthyloxycarbonyl (1- and 2-) groups, which may be substituted or unsubstituted;

aryloxycarbonyloxy groups in which the aryl part is $C_6$-$C_{10}$ and is unsubstituted or has at least one substituent selected from the group consisting of substituents (h), defined above and exemplified below, especially the phenoxycarbonyloxy and naphthyloxycarbonyloxy (1- and 2-) groups, which may be substituted or unsubstituted;

aralkyloxycarbonyl groups in which the alkyl part is $C_1$-$C_4$, preferably $C_1$-$C_3$ and more preferably $C_1$ or $C_2$, and the or each aryl part is $C_6$-$C_{10}$ and is unsubstituted or has at least one substituent selected from the group consisting of substituents (h), defined above and exemplified below, especially the benzyloxycarbonyl, phenethyloxycarbonyl, 1-phenylethoxycarbonyl, 3-phenylpropoxycarbonyl, p-nitrobenzyloxycarbonyl and naphthylmethoxycarbonyl (1- and 2-) groups, which may be substituted or unsubstituted;

aralkyloxycarbonyloxy groups in which the alkyl part is $C_1$-$C_4$, preferably $C_1$-$C_3$ and more preferably $C_1$ or $C_2$, and the or each aryl part is $C_6$-$C_{10}$ and is unsubstituted or has at least one substituent selected from the group consisting of substituents (h), defined above and exemplified below, especially the benzyloxycarbonyloxy, phenethyloxycarbonyloxy, 1-phenylethoxycarbonyloxy, 3-phenylpropoxycarbonyloxy, p-nitrobenzyloxycarbonyloxy and naphthylmethoxycarbonyloxy (1- and 2-) groups, which may be substituted or unsubstituted;

$C_1$-$C_6$ aliphatic carboxylic acyl groups, which may be unsubstituted or may have at least one substituent selected from the group consisting of substituents (f), defined above and exemplified below; these may be straight or branched chain alkanoyl groups containing from 1 to 6 carbon atoms, and examples include the formyl, acetyl, propionyl, butyryl, isobutyryl, valeryl, isovaleryl, pivaloyl and hexanoyl groups, of which the formyl and acetyl groups are more preferred;

aromatic carboxylic acyl groups in which the aryl part is $C_6$-$C_{10}$ and is unsubstituted or has at least one substituent selected from the group consisting of substituents (h), defined below, such as the benzoyl, 1-naphthoyl and 2-naphthoyl groups and such groups bearing one or more of substituents (h);

$C_1$-$C_6$ aliphatic carboxylic acyloxy groups, which may be unsubstituted or may have at least one substituent selected from the group consisting of substituents (f), defined above and exemplified below; these may be straight or branched chain alkanoyloxy groups containing from 1 to 6 carbon atoms, and examples include the formyloxy, acetoxy, propionyloxy, butyryloxy, isobutyryloxy, valeryloxy, isovaleryloxy, pivaloyloxy and hexanoyloxy groups, of which the formyloxy and acetoxy groups are more preferred; such groups may be substituted or unsubstituted;

aromatic carboxylic acyloxy groups in which the aryl part is $C_6$-$C_{10}$ and is unsubstituted or has at least one substituent selected from the group consisting of substituents (h), defined below, such as the benzoyloxy, 1-naphthoyloxy and 2-naphthoyloxy groups and such groups bearing one or more of substituents (h);

$C_1$-$C_6$ aliphatic carboxylic acylamino groups, which may be unsubstituted or may have at least one substituent selected from the group consisting of substituents (f), defined above and exemplified below; these may be straight or branched chain alkanoylamino groups containing from 1 to 6 carbon atoms, and examples include the formamido, acetamido, propionamido, butyramido, isobutyramido, valeramido, isovaleramido, pivaloylamino and hexanoylamino groups, of which the formylamino and acetamino groups are more preferred; such groups may be substituted or unsubstituted;

aromatic carboxylic acylamino groups in which the aryl part is $C_6$-$C_{10}$ and is unsubstituted or has at least one substituent selected from the group consisting of substituents (h), defined below, such as the benzamido, 1-naphthoylamino and 2-naphthoylamino groups and such groups bearing one or more of substituents (h);

sulfo groups;

$C_1$-$C_6$ alkylsulfinyl groups, which may be straight or branched chain alkylsulfinyl groups containing from 1 to 6 carbon atoms, and examples include the methylsulfinyl, ethylsulfinyl, propylsulfinyl, isopropylsulfinyl, butylsulfinyl, isobutylsulfinyl, sec-butylsulfinyl, t-butylsulfinyl, pentylsulfinyl, isopentylsulfinyl, 2-methylbutylsulfinyl, hexylsulfinyl, isohexylsulfinyl and 2-methylpentylsulfinyl groups, of which the methylsulfinyl, ethylsulfinyl, propylsulfinyl and butylsulfinyl groups are preferred, the methylsulfinyl group generally being most preferred;

$C_1$–$C_6$ alkylsulfonyl groups, which may be straight or branched chain alkylsulfonyl groups containing from 1 to 6 carbon atoms, and examples include the methylsulfonyl, ethylsulfonyl, propylsulfonyl, isopropylsulfonyl, butylsulfonyl, isobutylsulfonyl, sec-butylsulfonyl, t-butylsulfonyl, pentylsulfonyl, isopentylsulfonyl, 2-methylbutylsulfonyl, hexylsulfonyl, isohexylsulfonyl and 2-methylpentylsulfonyl groups, of which the methylsulfonyl, ethylsulfonyl, propylsulfonyl and butylsulfonyl groups are preferred, the methylsulfonyl group generally being most preferred;

$C_1$–$C_6$ alkylsulfonylamino groups, which may be straight or branched chain alkylsulfonylamino groups containing from 1 to 6 carbon atoms, and examples include the methylsulfonylamino, ethylsulfonylamino, propylsulfonylamino, isopropylsulfonylamino, butylsulfonylamino, isobutylsulfonylamino, sec-butylsulfonylamino, t-butylsulfonylamino, pentylsulfonylamino, isopentylsulfonylamino, 2-methylbutylsulfonylamino, hexylsulfonylamino, isohexylsulfonylamino and 2-methylpentylsulfonylamino groups, of which the methylsulfonylamino, ethylsulfonylamino, propylsulfonylamino and butylsulfonylamino groups are preferred, the methylsulfonylamino group generally being most preferred;

arylsulfinyl groups in which the aryl part is $C_6$–$C_{10}$ and is unsubstituted or has at least one substituent selected from the group consisting of substituents (h), defined below, such as the benzenesulfinyl, 1-naphthylsulfinyl and 2-naphthylsulfinyl groups, and such groups bearing one or more of substituents (h), for example the p-toluenesulfinyl group;

arylsulfonyl groups in which the aryl part is $C_6$–$C_{10}$ and is unsubstituted or has at least one substituent selected from the group consisting of substituents (h), defined below, such as the benzenesulfonyl, 1-naphthylsulfonyl and 2-naphthylsulfonyl groups, and such groups bearing one or more of substituents (h), for example the p-toluenesulfonyl group;

arylsulfonylamino groups in which the aryl part is $C_6$–$C_{10}$ and is unsubstituted or has at least one substituent selected from the group consisting of substituents (h), defined below, such as the benzenesulfonylamino, 1-naphthylsulfonylamino and 2-naphthylsulfonylamino groups, and such groups bearing one or more of substituents (h), for example the p-toluenesulfonylamino group;

$C_1$–$C_4$ alkylene groups, which may be straight or branched chain groups, such as the methylene, dimethylene, trimethylene, tetramethylene, 1-methylmethylene, 1-methyldimethylene, 1-methyltrimethylene, 2-methyltrimethylene and 1-ethyldimethylene groups, of which the trimethylene group is preferred;

$C_1$–$C_3$ alkylenedioxy groups, which may be straight or branched chain groups, such as the methylenedioxy, dimethylenedioxy, trimethylenedioxy or 1-methylmethylenedioxy groups, of which the methylenedioxy group is preferred;nitro groups;

cyano groups;

halogen atoms, for example the fluorine, chlorine, iodine and bromine atoms, of which the fluorine, chlorine and bromine atoms are preferred, the fluorine and chlorine atoms being most preferred;

hydroxy groups; and mercapto groups.

Preferred examples of groups which may be represented by Ar include the phenyl group itself and phenyl groups having one or more (up to 5) substituents selected from the group consisting of: cyano groups; halogen atoms; carboxy groups; methyl groups; ethyl groups; methoxycarbonyl groups; trifluoromethyl groups; carbamoyl groups; cyanomethyl groups; methylthio groups; methoxy groups; methylsulfinyl groups; methylsulfonyl groups; nitro groups; dimethylamino groups; hydroxymethyl groups; 2-hydroxyethyl groups; carboxymethyl groups; methoxycarbonyl methyl groups; dimethylaminomethyl groups; 2-aminoethylthiomethyl groups; 2-dimethylaminoethyl groups; hydroxy groups; acetyl groups; vinyl groups; ethynyl groups; 2-mercaptoethyl groups; mercapto groups; acetamido groups; and methylsulfonylamino groups. Where there are two or more of these groups, the groups may be the same or different.

Specific preferred examples of groups which may be represented by Ar include the 4-carboxyphenyl, 4-methylphenyl, 3-methylphenyl, 3-ethylphenyl, 4-ethylphenyl, 3-methoxycarbonylphenyl, 4-methoxycarbonylphenyl, 4-chlorophenyl, 3-chlorophenyl, 4-fluorophenyl, 3-fluorophenyl, 2-fluorophenyl, 4-bromophenyl, 3,4-difluorophenyl, 2,4-difluorophenyl, 4-chloro-2-fluorophenyl, 4-trifluoromethylphenyl, 3-trifluoromethylphenyl, 4-carbamoylphenyl, 3-carbamoylphenyl, 4-cyanophenyl, 3-cyanophenyl, 2-cyanophenyl, 4-(cyanomethyl)phenyl, 3-(cyanomethyl)phenyl, 2-(cyanomethyl)phenyl, 3-ethoxycarbonylphenyl, 4-ethoxycarbonylphenyl, 2,4-dichlorophenyl, 4-methylthiophenyl, 4-methoxyphenyl, 3-methylthiophenyl, 3-methoxyphenyl, 4-methylsulfinylphenyl, 3-methylsulfinylphenyl, 3-methylsulfonylphenyl, 4-methylsulfonylphenyl, 4-nitrophenyl, 3-nitrophenyl, phenyl, 4-dimethylaminophenyl, 4-(hydroxymethyl)phenyl, 2-(2-hydroxyethyl)phenyl, 4-(2-hydroxyethyl)phenyl, 4-(carboxymethyl)phenyl, 4-(methoxycarbonylmethyl)phenyl, 2-(2-dimethylaminoethyl)phenyl, 4-[(2-aminoethyl)thiomethyl]phenyl, 4-(2-aminoethylthio)phenyl, 4-hydroxyphenyl, 3-hydroxyphenyl, 4-acetylphenyl, 4-acetyl-3-hydroxyphenyl, 4-vinylphenyl, 4-ethynylphenyl, 3-carbamoylmethylphenyl, 3-(2-mercaptoethyl)phenyl, 4-mercaptophenyl, 3-(cyanomethyl)phenyl, 4-acetamidophenyl, 3,4,5-trimethoxyphenyl and 4-methylsulfonylaminophenyl groups.

In the case of those compounds of the present invention where $R^1$ represents a hydrogen atom, these are 7-amino compounds and are of considerable value in the preparation of other derivatives, including those of the present invention. In general, such 7-amino compounds are not expected to have any substantial antibacterial activity in their own right.

Where $R^1$ represents an acyl group, this may be: an optionally substituted $C_1$–$C_{10}$ alkanoyl group; an optionally substituted $C_3$–$C_{10}$ alkenoyl group; a $C_3$–$C_6$ alkynoyl group; an aromatic acyl group having from 7 to 11 carbon atoms which is unsubstituted or has at least one of substituents (b); a group of formula Het—CO— in which Het represents a heterocyclic group; or an optionally substituted cycloalkyl-carbonyl group.

Where $R^1$ represents an optionally substituted $C_1$–$C_{10}$ alkanoyl group, this may be a straight or branched chain group. Examples of such groups include the formyl, acetyl, propionyl, butyryl, isobutyryl, 2-methylpropionyl, pentanoyl, 2-methylbutyryl, pivaloyl, valeryl, isovaleryl, hexanoyl, 2-methylpentanoyl, 3-methylpentanoyl, 4-methylpentanoyl, heptanoyl, 2-methylhexanoyl, 3-ethylhexanoyl, octahoyl, 2-methylheptanoyl, 3-ethylheptanoyl, 2-ethyl-3-methylpentanoyl, 3-ethyl-2-methylpentanoyl, nonanoyl, 2-methyloctanoyl, 7-methyloctanoyl, 4-ethylheptanoyl, 3-ethyl-2-methylhexanoyl, 2-ethyl-1-methylhexanoyl, decanoyl, 2-methylnonanoyl, 8-methylnonanoyl, 5-ethyloctanoyl, 3-ethyl-2-methylheptanoyl and 3,3-diethylhexanoyl groups. Such groups may be unsubstituted or they may have one or more of substituents (a), defined above and exemplified generally below. Without prejudice to the generality of the definition of these substituted groups, amongst examples of such substituted groups are included the thiazolylacetyl and 1,2,4-thiadiazolylacetyl groups and such groups having one or more of substituents (c) on the thiazolyl or thiadiazolyl group (preferably at the 2-position of the thiazolyl group or at the 5-position of the thiadiazolyl group, and more preferably an amino group at the 2-position of the thiazolyl group or at the 5-position of the thiadiazolyl group) and/or having a group of formula $=NOR^3$, a halogen atom or an alkyl group on the α-carbon atom of the acetyl group, as described in greater detail hereafter. Other examples of such substituted alkanoyl groups include the glycoloyl, lactoyl, glyceroyl, tropoyl, benziloyl, alanyl, β-alanyl, phenylalanyl, histidyl, homoseryl, isoleucyl, leucyl, lysyl, methionyl, norleucyl, norvalyl, ornithyl, sarcosyl, threonyl, thyronyl, tyrosyl, valyl, cysteinyl, homocysteinyl, tryptophyl, hippuryl, hydratropoyl, α-amino-α-phenylacetyl, α-amino-α-(p-hydroxyphenyl)acetyl, α-hydroxy-α-phenylacetyl, α-formyloxy-α-phenylacetyl, α-phenyl-α-sulfoacetyl, α-carboxy-α-phenylacetyl, α-carboxy-α-(p-hydroxyphenyl)acetyl, α-(4-hydroxynicotinoylamino)-α-(p-hydroxyphenyl)acetyl, α-(4-ethyl-2,3-dioxo-1-piperazinylcarbonyl-amino)-α-(p-hydroxyphenyl)acetyl, phenylacetyl, o-aminomethylphenylacetyl, α-amino-α-cyclohexa-1,4-dienylacetyl, cyanoacetyl, thienylacetyl, furylacetyl, α-furyl-α-hydroxyiminoacetyl, α-furyl-α-methoxyiminoacetyl, 4-pyridylthioacetyl, 4-pyridyloxyacetyl, tetrazolylacetyl, (difluoromethylthio)acetyl, (cyanomethylthio)acetyl, chloroacetyl and (2-amino-2-carboxyethylthio)acetyl groups.

Where $R^1$ represents an optionally substituted $C_3$–$C_{10}$ alkenoyl group, this may be a straight or branched chain group. Examples of such unsubstituted groups include the acryloyl, methacryloyl, crotonoyl, isocrotonoyl and decenoyl groups. These groups may be unsubstituted or may have one or more of substituents (a), defined above and exemplified below. Examples of such substituted groups include the atropoyl, cinnamoyl and 2-(2-aminothiazolyl)-4-carboxybut-2-enoyl groups.

Where $R^1$ represents a $C_3$–$C_6$ alkynoyl group, this may be a straight or branched chain group. Examples of such groups include the propioloyl group.

Where $R^1$ represents a carbocyclic aromatic carboxylic acyl group, this has from 7 to 11 carbon atoms and is unsubstituted or has at least one substituent selected from the group consisting of substituents (b), defined above and exemplified below. Examples of the unsubstituted groups include the benzoyl, 1-naphthoyl, 2-naphthoyl groups. Examples of such substituted groups include the o-carboxybenzoyl, m-carboxybenzoyl, p-carboxybenzoyl, o-toluoyl, p-toluoyl, m-toluoyl, salicyloyl, anisoyl, vanilloyl, veratroyl, piperonoyl, protocatechuoyl and galloyl groups.

Where $R^1$ represents a group of formula Het—CO—, Het represents a heterocyclic group having from 4 to 7, more preferably from 4 to 6, ring atoms of which from 1 to 4 are hetero-atoms selected from the group consisting of nitrogen, oxygen and sulfur hetero-atoms. More preferably, the heterocyclic group has 0 or from 1 to 4 nitrogen atoms, 0, 1 or 2 oxygen atoms and 0, 1 or 2 sulfur atoms, provided that the total number of heteroatoms is at least 1 and does not exceed 4 or does not exceed a number 1 fewer than the number of ring atoms. The heterocyclic group may be unsubstituted or may have at least one substituent selected from the group consisting of substituents (c), defined above and exemplified below. Specific examples of such substituted and unsubstituted heterocyclic carbonyl groups include the nicotinoyl, isonicotinoyl, furoyl, thenoyl, picolinyl, prolyl and 4-(α-carbamoyl-α-carboxymethylene)-1,3-dithietanylcarbonyl groups.

Where $R^1$ represents a cycloalkylcarbonyl group, the cycloalkyl part has from 3 to 7 ring carbon atoms and is unsubstituted or has at least one substituent selected from the group consisting of substituents (b), defined above and exemplified below. Examples of such groups include the cyclopropylcarbonyl, cyclobutylcarbonyl, cyclopentylcarbonyl, cyclohexylcarbonyl and cycloheptylcarbonyl groups and such groups having one or more of substituents (b).

Where substituent (a) is a $C_1$–$C_6$ alkoxy group, a $C_1$–$C_6$ alkylthio group, a substituted $C_1$–$C_6$ alkoxy group, a substituted $C_1$–$C_6$ alkylthio group, a mono- or di- alkylamino group, a mono- or di- alkylcarbonyl group, a $C_2$–$C_{11}$, preferably $C_2$–$C_7$, alkoxycarbonyl group, an aryloxycarbonyl group, an aralkyloxycarbonyl group, a $C_1$–$C_6$ aliphatic carboxylic acyl group, a substituted $C_1$–$C_6$ aliphatic carboxylic acyl group, an aromatic carboxylic acyl group, a $C_1$–$C_6$ aliphatic carboxylic acyloxy group, a substituted $C_1$–$C_6$ aliphatic carboxylic acyloxy group, an aromatic carboxylic acyloxy group, a $C_1$–$C_6$ aliphatic carboxylic acylamino group, a substituted $C_1$–$C_6$ aliphatic carboxylic acylamino group, an aromatic carboxylic acylamino group, a $C_1$–$C_6$ alkylsulfinyl group, a $C_1$–$C_6$ alkylsulfonyl group, an arylsulfinyl group, an arylsulfonyl group or a halogen atom, these may be as exemplified above in relation to the same groups and atoms which may be included within substituents (b).

In the case of the groups of formula Het—O—, Het—S—, Het—CO—O— and Het—CO—NH—, Het represents a heterocyclic group having from 4 to 7 ring atoms of which from 1 to 4 are hetero-atoms selected from the group consisting of nitrogen, oxygen and sulfur hetero-atoms. More preferably, the heterocyclic group represented by Het has 0 or from 1 to 4 nitrogen atoms, 0, 1 or 2 oxygen atoms and 0, 1 or 2 sulfur atoms, provided that the total number of hetero-atoms is at least 1 and does not exceed 4 or does not exceed a number 1 fewer than the number of ring atoms. More preferably, the group has from 1 to 3 such hetero-atoms, the maximum number of nitrogen atoms then being 3. The heterocyclic group may be unsubstituted or it may have at least one substituent selected from the group consisting of substituents (c), defined above and exemplified below. Examples of such unsubstituted heterocyclic groups include the thienyl, furyl, pyranyl, pyrrolyl, imidazolyl, pyrazolyl, thiazolyl, isothiazolyl, thiadiazolyl, triazolyl, oxazolyl, isoxazolyl, pyridyl, pyrazinyl, pyrimidinyl, pyridazinyl, furazanyl, pyrrolidinyl, pyrrolinyl, imidazolidinyl, imidazolinyl, pyrazolidinyl, pyrazolinyl, piperidyl (e.g. piperidino and 4-piperidyl), piperazinyl, morpholinyl, thiomorpholinyl and azepinyl groups. Examples of such substituted heterocyclic groups include the 6-chloro-3-pyridyl, 6-(trifluoromethyl)-3-pyridyl, 5-chloro-2-pyridyl, 5-(trifluoromethyl)-2-furyl, 5-(trifluoromethyl)-2-thienyl, 5-chloro-2-thienyl, 4-hydroxy-3-pyridyl, 5-methyl-2-oxo-1,3-dioxolen-4-yl and 4-ethyl-2,3-dioxo-1-piperazinyl groups.

Where substituent (a) is an aryloxy, arylthio or aryl group, the aryl group or the aryl part of the aryloxy or arylthio group has from 6 to 10 ring carbon atoms and is unsubstituted or is substituted by one or more of substituents (e), defined below. Preferred unsubstituted aryl groups are the phenyl and the naphthyl (1- and 2-) groups. Preferred examples of substituted groups include the 4-methylphenyl, 3-methylphenyl, 3-ethylphenyl, 4-ethylphenyl, 4-chlorophenyl, 3-chlorophenyl, 4-fluorophenyl, 3-fluorophenyl, 2-fluorophenyl, 4-bromophenyl, 3,4-difluorophenyl, 2,4-difluorophenyl, 4-chloro-2-fluorophenyl 4-cyanophenyl, 3-cyanophenyl, 2-cyanophenyl, 2,4-dichlorophenyl, 4-nitrophenyl, 3-nitrophenyl, 4-aminomethylphenyl, 4-hydroxyphenyl, 3-hydroxyphenyl and 4-acetyl-3-hydroxyphenyl groups.

Where substituent (a) is an acylamino group, each acyl part is an aliphatic carboxylic acyl group having from 1 to 6 carbon atoms, e.g. an alkanoyl, alkenoyl or alkynoyl group, or is an aromatic carboxylic acyl group in which the aromatic part is an aryl group having from 6 to 10 ring carbon atoms and is unsubstituted; examples of such acylamino and diacylamino groups include the acetamido, propionamido, butyrylamino, isobutyrylamino, valeramido, isovaleramido, pivaloylamino, hexanoylamino, N,N-diacetylamino, N,N-dipropionylamino, benzamido, o-, m- and p-toluamido and naphthoylamino groups.

Where substituent (a) is a heterocyclic group, this has from 5 to 7 ring atoms of which from 1 to 4 are heteroatoms selected from the group consisting of nitrogen, oxygen and sulfur hetero-atoms and is unsubstituted or has at least one substituent selected from the group consisting of substituents (c), defined above and exemplified below. More preferably, the heterocyclic group has 0 or from 1 to 4 nitrogen atoms, 0, 1 or 2 oxygen atoms and 0, 1 or 2 sulfur atoms, provided that the total number of hetero-atoms is at least 1 and does not exceed 4 or does not exceed a number 1 fewer than the number of ring atoms. Examples of such heterocyclic groups include the thienyl, furyl, pyranyl, pyrrolyl, imidazolyl, pyrazolyl, thiazolyl, isothiazolyl, thiadiazolyl, triazolyl, oxazolyl, isoxazolyl, pyridyl, pyrazinyl, pyrimidinyl, pyridazinyl, furazanyl, pyrrolidinyl, pyrrolinyl, imidazolidinyl, imidazolinyl, pyrazolidinyl, pyrazolinyl, piperidyl (e.g. piperidino and 4-piperidyl), piperazinyl, morpholinyl (e.g. morpholino), thiomorpholinyl (e.g. thiomorpholino), azepinyl, 6-chloro-3-pyridyl, 6-(trifluoromethyl)-3-pyridyl, 5-chloro-2-pyridyl, 5-(trifluoromethyl)-2-furyl, 5-(trifluoromethyl)-2-thienyl, 5-chloro-2-thienyl and 5-methyl-2-oxo-1,3-dioxolen-4-yl groups.

Where substituent (a) is a cycloaliphatic hydrocarbon group having one or two carbon-carbon double bonds, it has from 5 to 7 ring carbon atoms, and where it is a cycloalkyl group it has from 3 to 7 ring carbon atoms. Examples include the cyclopropyl, cyclobutyl, cyclopentyl, cyclohexyl, cycloheptyl, cyclopentenyl, cyclohexenyl and cyclohexadienyl groups.

Where $R^3$ represents a $C_1$-$C_6$ alkyl group, a substituted $C_1$-$C_6$ alkyl group, a $C_2$-$C_6$ alkenyl group, a $C_2$-$C_6$ alkynyl group, a $C_3$-$C_7$ cycloalkyl group, a $C_2$-$C_{11}$, preferably $C_2$-$C_7$, alkoxycarbonyl group, an aryloxycarbonyl group, an aralkyloxycarbonyl group, an aliphatic or aromatic acyl group, a group of formula Het—CO—, a carbamoyl group or a mono- or di- alkylcarbamoyl group in which the or each alkyl part has from 1 to 6 carbon atoms, these groups may be as exemplified hereinabove in relation to the same groups which may be included among the groups of substituents (a).

Where $R^3$ represents an aralkyl group, the alkyl part is $C_1$-$C_4$ (and may be any of those alkyl groups having from 1 to 4 carbon atoms exemplified above. The group also has from 1 to 3 aryl parts, each of which is $C_6$, or has one aryl part which is $C_6$-$C_{14}$, said aryl part or parts being unsubstituted or having at least one substituent selected from the group consisting of substituents (e), defined below; these aryl parts are preferably phenyl ($C_6$), naphthyl (1- or 2-, $C_{10}$) or anthryl ($C_{14}$). Preferred examples include the benzyl, phenethyl, 1-phenylethyl, 3-phenylpropyl, 2-phenylpropyl, 1-phenylpropyl, 4-phenylbutyl, benzhydryl and anthrylmethyl groups.

Where $R^3$ represents a heterocyclic group, this has from 5 to 7 ring atoms of which from 1 to 4 are heteroatoms selected from the group consisting of nitrogen, oxygen and sulfur hetero-atoms, said heterocyclic group being monocyclic or is fused to a benzene ring or to another such heterocyclic group and it is unsubstituted or has at least one substituent selected from the group consisting of substituents (c), defined above. Examples of such groups include the thienyl, benzothienyl, pyridyl, furyl, pyranyl, isobenzofuranyl, pyrrolyl, imidazolyl, pyrazolyl, pyrazinyl, pyrimidinyl, pyridazinyl, indolizinyl, isoindolyl, 3H-indolyl, purinyl, thiazolyl, thiadiazolyl, quinolyl, isooxazolyl, pyrrolidinyl, pyrrolynyl, imidazolydinyl, imidazolinyl, pyrazolidinyl, piperidyl, pyrazolinyl, piperazinyl, indolinyl and morpholinyl groups.

Where $R^3$ represents a $C_4$-$C_8$ cycloalkoxycarbonyl group, this may be a cyclopropoxycarbonyl, cyclobutoxycarbonyl, cyclopentyloxycarbonyl, cyclohexyloxycarbonyl or cycloheptyloxycarbonyl group. Especially preferred groups which may be represented by $R^3$ include the hydrogen atom, the methyl group, the ethyl group, the fluoromethyl group, the difluoromethyl group, the trifluoromethyl group, the chloromethyl group, the dichloromethyl group, the trichloromethyl group, the iodomethyl group, the bromomethyl group, the cyanomethyl group, the butyryl group, the 2-aminoethoxycarbonyl group, the benzoyl group, the allyl group, the 2-propynyl group, the carboxymethyl group, the 1-carboxy-1-methylethyl group, the ethoxycarbonyl group, the isopropoxycarbonyl group, the methylcarbamoyl group, the methoxycarbonyl group, the cyclohexylcarbonyl group, the 2-oxo-5-methyl-1,3-dioxolen-4-ylmethyl group, the 2-aminoethyl group, the 2-amino-2-carboxyethyl group, the 2-methylaminoethyl group, the 2-dimethylaminoethyl group and the α-carboxy-3,4-dihydroxybenzyl group, of which the hydrogen atom, the methyl group, the ethyl group, the fluoromethyl group, the difluoromethyl group, the trifluoromethyl group, the chloromethyl group and the dichloromethyl group are particularly preferred.

The groups and atoms which may be included within substituents (c) to (i), may all be as exemplified in relation to the corresponding groups and atoms exemplified above, except as follows:

the aminoalkyl group of substituent (e), which is a $C_1$–$C_6$ group where the alkyl part may be a straight or branched chain group, and examples include the aminomethyl, 1-aminoethyl, 2-aminoethyl, 3-aminopropyl, 2-aminopropyl, 4-aminobutyl, 1-aminobutyl, 5-aminopentyl and 6-aminohexyl groups;

the $C_1$–$C_6$ alkylidene groups and substituted $C_1$–$C_6$ alkylidene groups of substituents (c), of which examples include the methylene, ethylidene, propylidene, isopropylidene, butylidene, isobutylidene, pentylidene and hexylidene groups and such groups having one or more of substituents (iO, defined above; and mono- and di- alkylsulfamoyl groups in which the or each alkyl part has from 1 to 6 carbon atoms, such as the methylsulfamoyl, ethylsulfamoyl, propylsulfamoyl, isopropylsulfamoyl, butylsulfamoyl, isobutylsulfamoyl, sec-butylsulfamoyl, t-butylsulfamoyl, pentylsulfamoyl, isopentylsulfamoyl, hexylsulfamoyl, isohexylsulfamoyl, dimethylsulfamoyl, diethylsulfamoyl, dipropylsulfamoyl, diisopropylsulfamoyl, dibutylsulfamoyl, methylethylsulfamoyl, methylpropylsulfamoyl, methylbutylsulfamoyl and ethylpropylsulfamoyl groups.

Preferred compounds of the invention are those classes of compounds of formula (I), defined above, in which:

(A) $R^1$ represents a $C_1$–$C_6$ alkanoyl group having at least one substituent selected from the group consisting of substituents ($a^1$), defined below;

(B) $R^2$ represents a hydrogen atom or a methoxy group;

(C) Ar represents an unsubstituted phenyl group or a substituted phenyl group having at least one substituent selected from the group consisting of substituents ($b^1$), defined below, more preferably the substituted phenyl group;

substituents ($a^1$):

$C_1$–$C_6$ alkoxy groups; $C_1$–$C_6$ alkylthio groups; substituted $C_1$–$C_6$ alkoxy groups having at least one substituent selected from the group consisting of substituents ($d^1$), defined below; substituted $C_1$–$C_6$ alkylthio groups having at least one substituent selected from the group consisting of substituents ($d^1$), defined below; groups of formula $Het^1$—O—, in which $Het^1$ is as defined below; groups of formula $Het^1$—S—, in which $Het^1$ is as defined below; phenoxy groups in which the phenyl part is unsubstituted or has at least one substituent selected from the group consisting of substituents (e), defined above; phenylthio groups in which the phenyl part is unsubstituted or has at least one substituent selected from the group consisting of substituents (e), defined above; amino groups; mono- and di- alkylamino groups in which the or each alkyl part has from 1 to 6 carbon atoms; carboxy groups; $C_2$–$C_7$ alkoxycarbonyl groups; phenoxycarbonyl groups in which the phenyl part is unsubstituted or has at least one substituent selected from the group consisting of substituents (e), defined above; aralkyloxycarbonyl groups in which the alkyl part is $C_1$–$C_4$ and the or each aryl part is $C_6$–$C_{10}$ and is unsubstituted or has at least one substituent selected from the group consisting of substituents (e), defined above; groups of formula $Het^1$—CO—NH—, in which $Het^1$ is as defined below; $C_1$–$C_6$ aliphatic carboxylic acylamino groups; substituted $C_1$–$C_6$ aliphatic carboxylic acylamino groups having at least one substituent selected from the group consisting of substituents ($f^1$), defined below; aromatic carboxylic acylamino groups in which the aryl part is a phenyl group which is unsubstituted or has at least one substituent selected from the group consisting of substituents (e), defined above; cyano groups; halogen atoms; hydroxy groups; groups of formula $=NOR^3$; heterocyclic groups having from 5 to 7 ring atoms of which from 1 to 4 are hetero-atoms selected from the group consisting of nitrogen, oxygen and sulfur hetero-atoms and being unsubstituted or having at least one substituent selected from the group consisting of substituents (c), defined above; $C_6$–$C_{10}$ carbocyclic aryl groups which are unsubstituted or have at least one substituent selected from the group consisting of substituents (e), defined above; sulfo groups; cycloaliphatic hydrocarbon groups having from 5 to 7 ring carbon atoms and one or two carbon-carbon double bonds; and cycloalkyl groups having from 3 to 7 ring carbon atoms;

$Het^1$ represents a heterocyclic group having from 4 to 6 ring atoms of which from 1 to 4 are hetero-atoms selected from the group consisting of nitrogen, oxygen and sulfur hetero-atoms, which group is unsubstituted or has at least one substituent selected from the group consisting of substituents (c), defined below;

$R^3$ represents: a hydrogen atom; a $C_1$–$C_6$ alkyl group; a substituted $C_1$–$C_6$ alkyl group having at least one substituent selected from the group consisting of substituents (g), defined above; a $C_3$ or $C_4$ alkenyl group; a $C_3$ or $C_4$ alkynyl group; a $C_1$–$C_6$ aliphatic carboxylic acyl group; a substituted $C_1$–$C_6$ aliphatic carboxylic acyl group having at least one substituent selected from the group consisting of substituents ($f^1$), defined below; an aromatic carboxylic acyl group in which the aryl part is $C_6$–$C_{10}$ and is unsubstituted or has at least one substituent selected from the group consisting of substituents (e), defined above; a group of formula $Het^2$—CO— in which $Het^2$ represents a heterocyclic group having 5 or 6 ring atoms of which one is a nitrogen atom and 1 or 2 are additional hetero-atoms selected from the group consisting of nitrogen, oxygen and sulfur hetero-atoms, said heterocyclic group being unsubstituted or having at least one substituent selected from the group consisting of substituents (c), defined below; a $C_2$–$C_{11}$ alkoxycarbonyl group; a $C_5$ or $C_6$ cycloalkoxycarbonyl group; an aryloxycarbonyl group in which the aryl part is a phenyl group which is unsubstituted or has at least one substituent selected from the group consisting of substituents (e), defined above; or an aralkyloxycarbonyl group in which the alkyl part is $C_1$–$C_2$ and the or each aryl part is a phenyl group which is unsubstituted or has at least one substituent selected from the group consisting of substituents (e), defined above;

substituents ($b^1$):

$C_1$–$C_6$ alkyl groups; $C_1$–$C_6$ alkoxy groups; $C_1$–$C_6$ alkylthio groups; substituted $C_1$–$C_6$ alkyl groups having at least one substituent selected from the group consisting of substituents ($f^1$), defined below; substituted $C_1$–$C_6$ alkoxy groups having at least one substituent selected from the group consisting of substituents ($f^1$), defined below; substituted $C_1$–$C_6$ alkylthio groups having at least one substituent selected from the group consisting of substituents (f¹), defined below; $C_2$-$C_4$ alkenyl groups; $C_2$-$C_4$ alkynyl groups; amino groups; mono- and di- alkylamino groups in which the or each alkyl part has from 1 to 6 carbon atoms; carbamoyl groups; mono- and di- alkylcarbamoyl groups in which the or each alkyl part has from 1 to 6 carbon atoms; carboxy groups; $C_2$-$C_5$ alkoxycarbonyl groups; $C_1$-$C_6$ aliphatic carboxylic acyl groups; substituted $C_1$-$C_6$ aliphatic carboxylic acyl groups having at least one substituent selected from the group consisting of substituents (f¹), defined below; aromatic carboxylic acyl groups in which the aryl part is $C_6$-$C_{10}$ and is unsubstituted or has at least one substituent selected from the group consisting of substituents (e), defined above; $C_1$-$C_6$ aliphatic carboxylic acyloxy groups; substituted $C_1$-$C_6$ aliphatic carboxylic acyloxy groups having at least one substituent selected from the group consisting of substituents (f¹), defined below; aromatic carboxylic acyloxy groups in which the aryl part is $C_6$-$C_{10}$ and is unsubstituted or has at least one substituent selected from the group consisting of substituents (e), defined above; $C_1$-$C_4$ alkylsulfinyl groups; $C_1$-$C_4$ alkylsulfonyl groups; arylsulfinyl groups in which the aryl part is a phenyl group which is unsubstituted or has at least one substituent selected from the group consisting of substituents (e), defined above; arylsulfonyl groups in which the aryl part is a phenyl group which is unsubstituted or has at least one substituent selected from the group consisting of substituents (e), defined above; nitro groups; cyano groups; halogen atoms; hydroxy groups; and mercapto groups;

substituents (d¹):

halogen atoms, cyano groups, amino groups, mono- and di- alkylamino groups in which the or each alkyl part has from 1 to 4 carbon atoms, carboxy groups, $C_2$-$C_5$ alkoxycarbonyl groups, aryloxycarbonyl groups in which the aryl part is a phenyl group which is unsubstituted or has at least one substituent selected from the group consisting of substituents (e), defined above, and aralkyloxycarbonyl groups in which the alkyl part is $C_1$-$C_3$ and the or each aryl part is a phenyl group which is unsubstituted or has at least one substituent selected from the group consisting of substituents (e), defined above;

substituents (f¹):

$C_1$-$C_6$ alkoxy groups; $C_1$-$C_6$ alkylthio groups; amino groups; mono- and di- alkylamino groups in which the or each alkyl part has from 1 to 6 carbon atoms; carbamoyl groups; mono- and di- alkylcarbamoyl groups in which the or each alkyl part has from 1 to 4 carbon atoms; carboxy groups; $C_2$-$C_9$ alkoxycarbonyl groups; aryloxycarbonyl groups in which the aryl part is a phenyl group which is unsubstituted or has at least one substituent selected from the group consisting of substituents (e), defined above; aralkyloxycarbonyl groups in which the alkyl part is $C_1$-$C_3$ and the or each aryl part is a phenyl group which is unsubstituted or has at least one substituent selected from the group consisting of substituents (e), defined above; $C_1$-$C_6$ aliphatic carboxylic acyl groups; aromatic carboxylic acyl groups in which the aryl part is a phenyl group which is unsubstituted or has at least one substituent selected from the group consisting of substituents (e), defined above; $C_1$-$C_6$ aliphatic carboxylic acyloxy groups; aromatic carboxylic acyloxy groups in which the aryl part is a phenyl group which is unsubstituted or has at least one substituent selected from the group consisting of substituents (e), defined above; $C_1$-$C_4$ alkylsulfinyl groups; $C_1$-$C_4$ alkylsulfonyl groups; arylsulfinyl groups in which the aryl part is a phenyl group which is unsubstituted or has at least one substituent selected from the group consisting of substituents (e), defined above; arylsulfonyl groups in which the aryl part is a phenyl group which is unsubstituted or has at least one substituent selected from the group consisting of substituents (e), defined above; nitro groups; cyano groups; halogen atoms; hydroxy groups; and mercapto groups;

and pharmaceutically acceptable salts and esters thereof.

More preferred are those compounds in which $R^1$ is as defined in (A) above, and $R^2$ is as defined in (B) above, and Ar is as defined in (C) above.

One of the more preferred classes of compounds of the present invention are:

(D) those compounds of formula (I) in which $R^1$ represents an alkanoyl group having a thiazolyl or 1,2,4-thiadiazolyl group on its α-carbon atom, and optionally having a group of formula =N—$OR^3$ or =$CR^{3'}R^{3''}$, also on its α-carbon atom and pharmaceutically acceptable salts and esters thereof.

Such compounds may be represented by the formula (Ia):

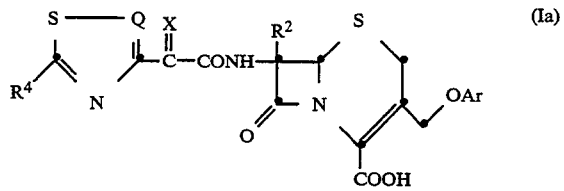

(in which Ar and $R^2$ are as defined above, $R^4$ represents a hydrogen atom or an amino group, Q represents a nitrogen atom or a CH group and X represents a group of formula =N—$OR^3$ or =$CR^{3'}R^{3''}$, where:

$R^3$ is as defined above; and $R^{3'}$ and $R^{3''}$ are independently selected from the group consisting of hydrogen atoms, halogen atoms, $C_1$-$C_6$ alkyl groups and $C_1$-$C_6$ alkyl groups having at least one substituent selected from the group consisting of substituents (g), defined and exemplified above;

or X represents two hydrogen atoms or 1 hydrogen atom and an acylamino group where the acyl part is a $C_1$-$C_6$ aliphatic carboxylic acyl group, a substituted $C_1$-$C_6$ aliphatic carboxylic acyl group having at least one substituent selected from the group consisting of substituents (f), defined above, or an aromatic carboxylic acyl group in which the aryl part is $C_6$-$C_{10}$ and is unsubstituted or has at least one substituent selected from the group consisting of substituents (e), defined above;

and pharmaceutically acceptable salts and esters thereof.

More preferred are said compounds of formula (Ia), where X represents said group of formula =N—$OR^3$ or =$CR^{3'}R^{3''}$, still more preferred are such compounds in which X represents said group of formula =N—$OR^3$ or =$CR^{3'}R^{3''}$ and $R^4$ represents an amino group, and most preferred are such compounds in which $R^2$ represents a hydrogen atom, X represents said group of formula 'N—OR$^3$ or =CR$^{3'}$R$^{3''}$ and R$^4$ represents an amino group.

In the compounds of formula (Ia), we especially prefer those compounds in which:

Ar represents a substituted phenyl group having at least one substituent selected from the group consisting of substituents (b$^1$), defined above;

R$^2$ represents a hydrogen atom or a methoxy group;

R$^4$ represents a hydrogen atom or an amino group;

Q represents a nitrogen atom or a CH group; and

X represents a group of formula =N—OR$^3$ or =CR$^{3'}$R$^{3''}$, where:

R$^3$ represents: a hydrogen atom; a C$_1$–C$_6$ alkyl group; a substituted C$_1$–C$_6$ alkyl group having at least one substituent selected from the group consisting of substituents (g), defined above; a C$_3$ or C$_4$ alkenyl group; a C$_3$ or C$_4$ alkynyl group; a C$_1$–C$_6$ aliphatic carboxylic acyl group; a substituted C$_1$–C$_6$ aliphatic carboxylic acyl group having at least one substituent selected from the group consisting of substituents (f$^1$), defined above; an aromatic carboxylic acyl group in which the aryl part is C$_6$–C$_{10}$ and is unsubstituted or has at least one substituent selected from the group consisting of substituents (e), defined above; a group of formula Het—CO— in which Het$^2$ represents a heterocyclic group having 5 or 6 ring atoms of which one is a nitrogen atom and 1 or 2 are additional hetero-atoms selected from the group consisting of nitrogen, oxygen and sulfur hetero-atoms, said heterocyclic group being unsubstituted or having at least one substituent selected from the group consisting of substituents (c), defined above; a C$_2$–C$_{11}$ alkoxycarbonyl group; a C$_5$ or C$_6$ cycloalkoxycarbonyl group; an aryloxycarbonyl group in which the aryl part is a phenyl group which is unsubstituted or has at least one substituent selected from the group consisting of substituents (e), defined above; or an aralkyloxycarbonyl group in which the alkyl part is C$_1$–C$_2$ and the or each aryl part is a phenyl group which is unsubstituted or has at least one substituent selected from the group consisting of substituents (e), defined above; and R$^{3'}$ and R$^{3''}$ are independently selected from the group consisting of hydrogen atoms, halogen atoms, C$_1$–C$_6$ alkyl groups and C$_1$–C$_6$ alkyl groups having at least one substituent selected from the group consisting of substituents (g), defined and exemplified above.

In the case of the compounds of formula (Ia), preferred thiazolylalkanoyl and thiadiazolylalkanoyl groups which may be at the 7-position of the cephem system include the: 4-thiazolylacetyl, 2-amino-4-thiazolylacetyl, 2-(2-aminothiazol-4-yl)-4-carboxybut-2-enoyl, α-(2-aminothiazol-4-yl)-α-formamidoacetyl, α-(2-aminothiazol-4-yl)-α-hydroxyiminoacetyl, α-(2-aminothiazol-4-yl)-α-methoxyiminoacetyl, α-(2-aminothiazol-4-yl)-α-ethoxyiminoacetyl, α-(2-aminothiazol-4-yl)-α-allyloxyiminoacetyl, α-(2-aminothiazol-4-yl)-α-(2-propynyloxyimino)acetyl, α-(2-aminothiazol-4-yl)-α-(carboxymethoxyimino)acetyl, α-(2-aminothiazol-4-yl)-α-(1-carboxy-1-methylethoxyimino)acetyl, α-(5-amino-1,2,4-thiadiazol-3-yl)-α-hydroxyiminoacetyl, α-(5-amino-1,2,4-thiadiazol-3-yl)-α-methoxyiminoacetyl, α-(5-amino-1,2,4-thiadiazol-3-yl)-α-ethoxyiminoacetyl, α-(2-aminothiazol-4-yl)-α-(ethoxycarbonyloxyimino)acetyl, α-(2-aminothiazol-4-yl)-α-(methoxycarbonyloxyimino)acetyl, α-(2-aminothiazol-4-yl)-α-(isopropoxycarbonyloxyimino)acetyl, α-(2-aminothiazol-4-yl)-α-methylcarbamoyloxyiminoacetyl, α-(2-aminothiazol-4-yl)-α-ethylcarbamoyloxyiminoacetyl, α-(2-aminothiazol-4-yl)-α-(cyclohexyloxycarbonyloxyimino)acetyl, α-(2-aminothiazol-4-yl)-α-(2-oxo-5-methyl-1,3-dioxolen-4-ylmethoxyimino)acetyl, α-(2-aminothiazol-4-yl)-β-chloroacryloyl, α-(2-aminoethoxyimino)-α-(2-aminothiazol-4-yl)acetyl , α-(2-amino-2-carboxyethoxyimino)-α-(2-aminothiazol-4-yl)acetyl, α-(2-aminothiazol-4-yl)-α-(2-methylaminoethoxyimino)acetyl, α-(2-aminothiazol-4-yl)-α-(2-dimethylaminoethoxyimino)acetyl, α-(2-aminothiazol-4-yl)-α-(cyanomethoxyimino)acetyl, α-(2-aminothiazol-4-yl)-α-(fluoromethoxyimino)acetyl, α-(2-aminothiazol-4-yl)-α-(difluoromethoxyimino)acetyl, α-(2-aminothiazol-4-yl)-α-(butyryloxyimino)acetyl, α-(2-aminothiazol-4-yl)-α-(2-aminoethoxycarbonyloxyimino)acetyl, and α-(2-aminothiazol-4-yl)-α-(α-carboxy-3,4-dihydroxybenzyloxyimino)acetyl groups.

Other preferred acyl groups represented by R$^1$ and which may be present at the 7-position in the compounds of the present invention include the α-amino-α-phenylacetyl, α-amino-α-(4-hydroxyphenyl)acetyl, α-hydroxy-α-phenylacetyl, α-formyloxy-α-phenylacetyl, α-sulfo-α-phenylacetyl, α-carboxy-α-(4-hydroxyphenyl)acetyl, α-(4-hydroxynicotinoylamino)-α-(4-hydroxyphenyl)acetyl, α-(4-ethyl-2,3dioxo-1-piperazinylcarbonylamino)-α-(4-hydroxyphenyl)acetyl, α-(2-aminomethylphenyl)acetyl, α-amino-α-(cyclohexa-1,4-dienyl)acetyl, cyanoacetyl, 2-thienylacetyl, α-(methoxyimino)-α-(2-furyl)acetyl, (2-amino-4-thiazolyl)acetyl, 2-(2-amino-4-thiazolyl)-4-carboxyisocrotonoyl, α-(2-amino-4-thiazolyl)-α-(formamido)acetyl, 4-pyridylthioacetyl, 1H-tetrazolylacetyl, difluoromethylthioacetyl, fluoromethylthioacetyl, cyanomethylthioacetyl, (2-amino-2-carboxyethylthio)acetyl and 4-(α-carbamoyl-α-carboxymethylene)-1,3-dithietanylcarbonyl groups.

Those compounds of formula (I) in which R$^1$ represents a hydrogen atom, that is to say the 7-amino compounds, are valuable intermediates in the preparation of others of the compounds of the invention which have useful antibiotic activity, as explained hereafter. Additionally certain of the other compounds of the invention are of more value as intermediates than as antibiotics.

The compounds presently believed to be of potentially the greatest value as antibiotics are those of formula (Ia), defined above.

The compounds of the present invention contain a carboxy group at the 4-position and can, therefore, form esters, which also form part of the present invention. There is no limitation upon the nature of such esters, provided that, where the resulting compound is to be used for therapeutic purposes, it is pharmaceutically acceptable, which, as is well known in the art, means that the compound does not have reduced activity (or unacceptably reduced activity) or increased toxicity (or unacceptably increased toxicity) as compared with the corresponding compound of formula (I), i.e. the free acid. Where, however, the compound is to be used for non-therapeutic purposes, e.g. as an intermediate in the preparation of ocher compounds, even this limitation does not apply, and the nature of the ester group may be chosen having regard simply to process criteria. Examples of suitable ester groups which may replace the hydrogen atom of the carboxy group at the 4-position include:

$C_1$–$C_{20}$ alkyl groups, more preferably $C_1$–$C_6$ alkyl groups, such as those exemplified in relation to substituents (b) etc. and higher alkyl groups as are well known in the art, such as the heptyl, 1-methylhexyl, 2-methylhexyl, 5-methylhexyl, 3-ethylpentyl, octyl, 2-methylheptyl, 5-methylheptyl, 2-ethylhexyl, 2-ethyl-3-methylpentyl, 3-ethyl-2-methylpentyl, nonyl, 2-methyloctyl, 7-methyloctyl, 4-ethylheptyl, 3-ethyl-2-methylhexyl, 2-ethyl-1-methylhexyl, decyl, 2-methylnonyl, 8-methylnonyl, 5-ethyloctyl, 3-ethyl-2methylheptyl, 3,3-diethylhexyl, undecyl, 2-methyldecyl, 9-methyldecyl, 4-ethylnonyl, 3,5-dimethylnonyl, 3-propyloctyl, 5-ethyl-4-methyloctyl, dodecyl, 1-methylundecyl, 10-methylundecyl, 3-ethyldecyl, 5-propylnonyl, 3,5-diethyloctyl, tridecyl, 11-methyldodecyl, 7-ethylundecyl, 4-propyldecyl, 5-ethyl-3-methyldecyl, 3-pentyloctyl, tetradecyl, 12-methyltridecyl, 8-ethyldodecyl, 6-propylundecyl, 4-butyldecyl, 2-pentylnonyl, pentadecyl, 13-methyltetradecyl, 10-ethyltridecyl, 7-propyldodecyl, 5-ethyl-3-methyldodecyl, 4-pentyldecyl, hexadecyl, 14-methylpentadecyl, 6-ethyltetradecyl, 4-propyltridecyl, 2-butyldodecyl, heptadecyl, 15-methylhexadecyl, 7-ethylpentadecyl, 3-propyltetradecyl, 5-pentyldodecyl, octadecyl, 16-methylheptadecyl, 5-propylpentadecyl, nonadecyl, 17-methyloctadecyl, 4-ethylheptadecyl, icosyl, 18-methylnonadecyl and 3-ethyloctadecyl groups, but most preferably the methyl, ethyl and t-butyl groups;

$C_3$–$C_7$ cycloalkyl groups, for example the cyclopropyl, cyclobutyl, cyclopentyl, cyclohexyl or cycloheptyl group;

aralkyl groups in which the aromatic group is $C_6$–$C_{14}$, which may be substituted or unsubstituted, and, if substituted may have at least one substituent selected from the group consisting of substituents (e), defined and exemplified above; examples of such aralkyl groups include the benzyl, phenethyl, 1-phenylethyl, 3-phenylpropyl, 2-phenylpropyl, 1-naphthylmethyl, 2-naphthylmethyl, 2-(1-naphthyl)ethyl, 2-(2-naphthyl)ethyl, benzhydryl (i.e. diphenylmethyl), triphenylmethyl, bis(o-nitrophenyl)methyl, 9-anthrylmethyl, 2,4,6-trimethylbenzyl, 4-bromobenzyl, 2-nitrobenzyl, 4-nitrobenzyl, 2-nitrobenzyl, 4-methoxybenzyl and piperonyl groups;

alkenyl groups such as those defined and exemplified above in relation to substituents (b), but which may be substituted or unsubstituted and, if substituted have at least one substituent selected from the group consisting of substituents (f) defined above; examples of the unsubstituted groups are given above in relation to substituents (b), and preferred groups include the allyl, 2-chloroallyl and 2-methylallyl groups;

halogenated $C_1$–$C_6$, preferably $C_1$–$C_4$, alkyl groups in which the alkyl part is as defined and exemplified in relation to the alkyl groups which may be represented by substituents (b) etc. and the halogen atom is chlorine, fluorine, bromine or iodine, such as the 2,2,2-trichloroethyl, 2-haloethyl (e.g. 2-chloroethyl, 2-fluoroethyl, 2-bromoethyl or 2-iodoethyl), 2,2-dibromoethyl and 2,2,2-tribromoethyl group;

substituted silylalkyl groups, in which the alkyl part is as defined and exemplified in relation to the alkyl groups which may be represented by substituents (b) etc. and the silyl group has up to 3 substituents selected from the group consisting of $C_1$–$C_6$ alkyl groups and phenyl groups which are unsubstituted or have at least one substituent selected from the group consisting of substituents (e) defined and exemplified above, for example a 2-trimethylsilylethyl group;

phenyl groups, in which the phenyl group is unsubstituted or substituted, preferably with at least one $C_1$–$C_4$ alkyl or acylamino group, for example the phenyl, tolyl and benzamidophenyl groups; phenacyl groups, which may be unsubstituted or have at least one substituent selected from the group consisting of substituents (e) defined and exemplified above, for example the phenacyl group itself or the p-bromophenacyl group;

cyclic and acyclic terpenyl groups, for example the geranyl, neryl, linalyl, phytyl, menthyl (especially m- and p- menthyl), thujyl, caryl, pinanyl, bornyl, norcaryl, norpinanyl, norbornyl, menthenyl, camphenyl and norbornenyl groups;

terpenylcarbonyloxyalkyl and terpenyloxycarbonyloxyalkyl groups, in which the terpenyl group is as exemplified above, and is preferably a cyclic terpenyl group, for example the 1-(menthyloxycarbonyloxy)ethyl, 1-(menthylcarbonyloxy)ethyl, menthyloxycarbonyloxymethyl, menthylcarbonyloxymethyl, 1-(3-pinanyloxycarbonyloxy)ethyl, 1-(3-pinanylcarbonyloxy)ethyl, 3-pinanyloxycarbonyloxymethyl and 3-pinanylcarbonyloxymethyl groups;

alkoxymethyl groups, in which the alkoxy part is $C_1$–$C_6$, preferably $C_1$–$C_4$, and may itself be substituted by a single unsubstituted alkoxy group, such as the methoxymethyl, ethoxymethyl, propoxymethyl, isopropoxymethyl, butoxymethyl and methoxyethoxymethyl groups;

aliphatic acyloxymethyl groups, in which the acyl group is preferably an alkanoyl group and is more preferably a $C_2$–$C_6$ alkanoyl group, such as the acetoxymethyl, propionyloxymethyl, butyryloxymethyl, isobutyryloxymethyl and pivaloyloxymethyl groups;

higher aliphatic acyloxyalkyl groups in which the acyl group is preferably an alkanoyl group and is more preferably a $C_2$–$C_6$ alkanoyl group, and the alkyl part is $C_2$–$C_6$, and preferably $C_2$–$C_4$, such as the 1-pivaloyloxyethyl, 1-acetoxyethyl, 1-isobutyryloxyethyl, 1-pivaloyloxypropyl, 2-methyl-1-pivaloyloxypropyl, 2-pivaloyloxypropyl, 1-isobutyryloxyethyl, 1-isobutyryloxypropyl, 1-acetoxypropyl, 1-acetoxy-2-methylpropyl, 1-propionyloxyethyl, 1-propionyloxypropyl, 2-acetoxypropyl and 1-butyryloxyethyl groups;

cycloalkyl-substituted aliphatic acyloxyalkyl groups, in which the acyl group is preferably an alkanoyl group and is more preferably a $C_2$–$C_6$ alkanoyl group, the cycloalkyl substituent is $C_3$–$C_7$, and the alkyl part is a $C_1$–$C_6$ alkyl group, preferably a $C_1$–$C_4$ alkyl group, such as the (cyclohexylacetoxy)methyl, 1-(cyclohexylacetoxy)ethyl, 1-(cyclohexylacetoxy)propyl, 2-methyl-1-(cyclohexylacetoxy)propyl, (cyclopentylacetoxy)methyl, 1-(cyclopentylacetoxy)ethyl, 1-(cyclopentylacetoxy)propyl and 2-methyl-1-(cyclopentylacetoxy)propyl, groups;

alkoxycarbonyloxyalkyl groups, especially 1-(alkoxycarbonyloxy)ethyl groups, in which the alkoxy part is $C_1$–$C_{10}$, preferably $C_1$–$C_6$, and more preferably $C_1$–$C_4$, and the alkyl part is $C_1$–$C_6$, preferably $C_1$–$C_4$, such as the 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl, 1-isobutoxycarbonyloxyethyl, 1-sec-butoxycarbonyloxyethyl, 1-t-butoxycarbonyloxyethyl, 1-(1-ethylpropoxycarbonyloxy)ethyl and 1-(1,1-dipropylbutoxycarbonyloxy)ethyl groups, and other alkoxycarbonylalkyl groups, in which both the alkoxy and alkyl groups are $C_1$–$C_6$, preferably $C_1$–$C_4$, such as the 2-methyl-1-(isopropoxycarbonyloxy)propyl, 2-(isopropoxycarbonyloxy)propyl, isopropoxycarbonyloxymethyl, t-butoxycarbonyloxymethyl, methoxycarbonyloxymethyl and ethoxycarbonyloxymethyl groups;

cycloalkylcarbonyloxyalkyl and cycloalkyloxycarbonyloxyalkyl groups, in which the cycloalkyl group is $C_3$–$C_{10}$, preferably $C_3$–$C_7$, is mono- or poly- cyclic and is optionally substituted by at least one (and preferably only one) $C_1$–$C_4$ alkyl group (e.g. selected from those alkyl groups exemplified above) and the alkyl group is a $C_1$–$C_6$, more preferably $C_1$–$C_4$, alkyl group (e.g. selected from those alkyl groups exemplified above) and is most preferably methyl, ethyl or propyl, for example the 1-methylcyclohexylcarbonyloxymethyl, 1-methylcyclohexyloxycarbonyloxymethyl, cyclopentyloxycarbonyloxymethyl, cyclopentylcarbonyloxymethyl, 1-cyclohexyloxycarbonyloxyethyl, 1-cyclohexylcarbonyloxyethyl, 1-cyclopentyloxycarbonyloxyethyl, 1-cyclopentylcarbonyloxyethyl, 1-cycloheptyloxycarbonyloxyethyl, 1-cycloheptylcarbonyloxyethyl, 1-methylcyclopentylcarbonyloxymethyl, 1-methylcyclopentyloxycarbonyloxymethyl, 2-methyl-1-(1-methylcyclohexylcarbonyloxy)propyl, 1-(1-methylcyclohexylcarbonyloxy)propyl, 2-(1-methylcyclohexylcarbonyloxy)propyl, 1-(cyclohexylcarbonyloxy)propyl, 2-(cyclohexylcarbonyloxy)propyl, 2- methyl-1-(1-methylcyclopentylcarbonyloxy)propyl, 1-(1-methylcyclopentylcarbonyloxy)propyl, 2-(1-methylcyclopentylcarbonyloxy)propyl, 1-(cyclopentylcarbonyloxy)propyl, 2-(cyclopentylcarbonyloxy)propyl, 1-(1-methylcyclopentylcarbonyloxy)ethyl, 1-(1-methylcyclopentylcarbonyloxy)propyl, adamantyloxycarbonyloxymethyl, adamantylcarbonyloxymethyl, 1-adamantyloxycarbonyloxyethyl and 1-adamantylcarbonyloxyethyl groups: cycloalkylalkoxycarbonyloxyalkyl groups in which the alkoxy group has a single cycloalkyl substituent, the cycloalkyl substituent being $C_3$–$C_{10}$, preferably $C_3$–$C_7$, and mono- or poly- cyclic, for example the cyclopropylmethoxycarbonyloxymethyl, cyclobutylmethoxycarbonyloxymethyl, cyclopentylmethoxycarbonyloxymethyl, cyclohexylmethoxycarbonyloxymethyl, 1-(cyclopropylmethoxycarbonyloxy)ethyl, 1-(cyclobutylmethoxycarbonyloxy)ethyl, 1-(cyclopentylmethoxycarbonyloxy)ethyl and 1-(cyclohexylmethoxycarbonyloxy)ethyl groups;

(5-alkyl- or 5-phenyl- 2-oxo-1,3-dioxolen-4-yl)alkyl groups in which each alkyl group (which may be the same or different) is $C_1$–$C_6$, preferably $C_1$–$C_4$, and the phenyl group may be unsubstituted or substituted by at least one substituent selected from the group consisting of substituents (e), for example the (5-methyl-2-oxo-1,3-dioxolen-4-yl)methyl, (5-phenyl-2-oxo-1,3-dioxolen-4-yl)methyl, (5-isopropyl-2-oxo-1,3-dioxolen-4-yl)methyl, (5-t-butyl-2-oxo-1,3-dioxolen-4-yl)methyl and 1-(5-methyl-2-oxo-1,3-dioxolen-4-yl))ethyl groups; and other groups, especially groups which are easily removed in vivo such as the phthalidyl, indanyl and 2-oxo-4,5,6,7-tetrahydro-1,3-benzodioxolen-4-yl groups.

Of the above groups, we especially prefer those groups which can be removed easily in vivo, and most preferably the aliphatic acyloxymethyl groups, higher aliphatic acyloxyalkyl groups, cycloalkyl-aliphatic acyloxyalkyl groups, alkoxycarbonyloxyalkyl groups, cycloalkylcarbonyloxyalkyl groups, and cycloalkylalkoxycarbonyloxyalkyl groups.

The compounds of the present invention, especially those in which $R^1$ represents an aminothiazolylalkanoyl or aminothiadiazolylalkanoyl group, may contain a basic group and can, therefore, form acid addition salts. In addition, the compounds may form salts with the carboxylic acid group at the 4-position. The nature of such salts is not critical to the invention, provided that, where the compound is intended for use therapeutically, the salt is pharmaceutically acceptable, as explained above. However, where the compound is intended for other uses, e.g. as an intermediate in the preparation of other compounds, even this limitation does not apply and the nature of the salt may be chosen having regard solely to process criteria.

Examples of acids which can form such acid addition salts include: inorganic acids, such as hydrochloric acid, hydrobromic acid, hydroiodic acid, phosphoric acid, sulfuric acid or nitric acid; organic sulfonic acids, such as methanesulfonic acid, ethanesulfonic acid, benzenesulfonic acid or p-toluenesulfonic acid; and organic carboxylic acids, such as formic acid, oxalic acid, tartaric acid, citric acid, maleic acid, succinic acid, acetic acid, benzoic acid, mandelic acid, ascorbic acid, lactic acid, gluconic acid and malic acid.

The compounds of formula (I) may also form salts with cations, examples of which include:

metal atoms, especially alkali metal atoms, such as the sodium and potassium atoms, alkaline earth metal atoms, such as the calcium atom, and other atoms, such as the iron, magnesium, aluminum and cobalt atoms;

the ammonium group; cations derived from a trialkylamine, such as triethylamine, or from another organic base, such as procaine, dibenzylamine, phenethylamine, 2-phenylethylbenzylamine, ethanolamine, diethanolamine, a polyhydroxyalkylamine or N-methylglucosamine; and basic amino acids, such as lysine, arginine, ornithine or histidine.

Of the above, we prefer salts of an alkaline metal or of a mineral acid.

Examples of specific compounds of the invention are given in the following formulae (I-1) to (I-4), in which the substituents are as defined in the corresponding one of Tables 1 to 4, respectively [i.e. Table 1 relates to formula (I-1), Table 2 relates to formula (I-2), Table 3 relates to formula (I-3) and Table 4 relates to formula (I-4)]. In the Tables, the following abbreviations are used:

| Ac | acetyl |

-continued

| | |
|---|---|
| All | allyl |
| Boz | benzoyl |
| Byr | butyryl |
| iByr | isobutyryl |
| Bz | benzyl |
| Car | carbamoyl |
| iCro | isocrotonoyl |
| Dox | (5-methyl-2-oxo-1,3-dioxolen-4-yl)methyl |
| Et | ethyl |
| Etc | ethoxycarbonyl |
| Fo | formyl |
| Fur | furyl |
| cHx | cyclohexyl |
| Me | methyl |
| Mec | methoxycarbonyl |
| Mes | methanesulfonyl |
| Nic | nicotinoyl |
| Ph | phenyl |
| Piv | pivoloyl |
| Piz | piperazinyl |
| Prc | propoxycarbonyl |
| iPrc | isopropoxycarbonyl |
| Prg | propargyl (= 2-propynyl) |
| Pyr | pyridyl |
| Sfo | sulfo |
| Tez₁ | 1H-tetrazolyl |
| Tfm | trifluoromethyl |
| Thi | thienyl |
| Thiz | thiazolyl |

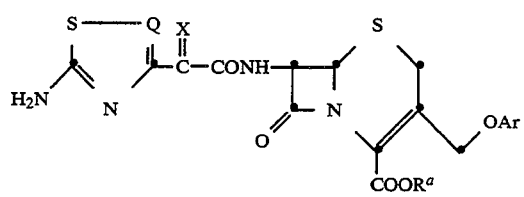

(I-1)

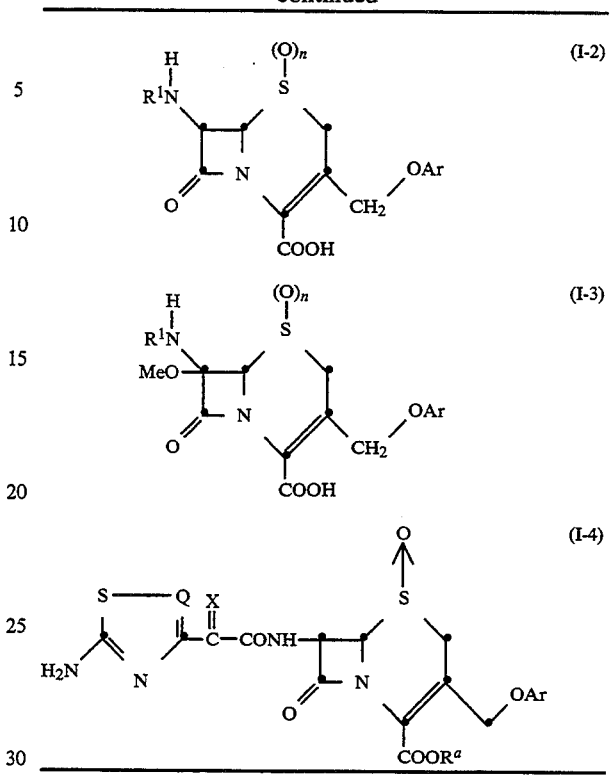

TABLE 1

| Cpd No. | Q | X | $R^a$ | Ar |
|---|---|---|---|---|
| 1-1 | CH | >NOH | H | 4-HOOCPh |
| 1-2 | CH | >NOH | H | 4-MePh |
| 1-3 | CH | >NOH | H | 3-MePh |
| 1-4 | CH | >NOH | H | 3-EtPh |
| 1-5 | CH | >NOH | H | 3-MecPh |
| 1-6 | CH | >NOH | H | 4-ClPh |
| 1-7 | CH | >NOH | H | 4-FPh |
| 1-8 | CH | >NOH | H | 3-FPh |
| 1-9 | CH | >NOH | H | 2-FPh |
| 1-10 | CH | >NOH | H | 4-BrPh |
| 1-11 | CH | >NOH | H | 3,4-diFPh |
| 1-12 | CH | >NOH | H | 2,4-diFPh |
| 1-13 | CH | >NOH | H | 4-Cl-2-FPh |
| 1-14 | CH | >NOH | H | 4-TfmPh |
| 1-15 | CH | >NOH | H | 3-TfmPh |
| 1-16 | CH | >NOH | H | 4-CarPh |
| 1-17 | CH | >NOH | H | 3-CarPh |
| 1-18 | CH | >NOH | H | 4-CNPh |
| 1-19 | CH | >NOH | H | 3-CNPh |
| 1-20 | CH | >NOH | H | 2-CNPh |
| 1-21 | CH | >NOH | H | 4-(CNMe)Ph |
| 1-22 | CH | >NOH | H | 3-(CNMe)Ph |
| 1-23 | CH | >NOH | H | 2-(CNMe)Ph |
| 1-24 | CH | >NOH | H | 3-EtcPh |
| 1-25 | CH | >NOH | H | 2,4-diClPh |
| 1-26 | CH | >NOH | H | 4-MeSPh |
| 1-27 | CH | >NOH | H | 4-MeOPh |
| 1-28 | CH | >NOH | H | 3-MeSPh |
| 1-29 | CH | >NOH | H | 3-MeOPh |
| 1-30 | CH | >NOH | H | 4-MeSOPh |
| 1-31 | CH | >NOH | H | 3-MeSO₂Ph |
| 1-32 | CH | >NOH | H | 4-MeSO₂Ph |
| 1-33 | CH | >NOH | H | 4-NO₂Ph |
| 1-34 | CH | >NOH | H | Ph |
| 1-35 | CH | >NOH | H | 4-NMe₂Ph |
| 1-36 | CH | >NOH | H | 4-(HOMe)Ph |
| 1-37 | CH | >NOH | H | 2-(2-HOEt)Ph |
| 1-38 | CH | >NOH | H | 4-(2-HOEt)Ph |

TABLE 1-continued

| Cpd No. | Q | X | R<sup>a</sup> | Ar |
|---|---|---|---|---|
| 1-39 | CH | >NOH | H | 4-(HOOCMe)Ph |
| 1-40 | CH | >NOH | H | 4-(MecMe)Ph |
| 1-41 | CH | >NOH | H | 2-(2-NMe$_2$Et)Ph |
| 1-42 | CH | >NOH | H | 4-[(2-NH$_2$Et)SMe]Ph |
| 1-43 | CH | >NOH | H | 4-(2-NH$_2$EtS)Ph |
| 1-44 | CH | >NOH | H | 4-HOPh |
| 1-45 | CH | >NOH | H | 3-HOPh |
| 1-46 | CH | >NOH | H | 4-AcPh |
| 1-47 | CH | >NOH | H | 4-Ac-3-HOPh |
| 1-48 | CH | >NOH | H | 3-NO$_2$Ph |
| 1-49 | CH | >NOH | H | 4-vinylPh |
| 1-50 | CH | >NOH | H | 4-ethynylPh |
| 1-51 | CH | >NOH | H | 4-MecPh |
| 1-52 | CH | >NOH | H | 3-CarMePh |
| 1-53 | CH | >NOH | H | 3-(2-HSEt)Ph |
| 1-54 | CH | >NOH | H | 4-HSph |
| 1-55 | CH | >NOMe | H | 4-BrPh |
| 1-56 | CH | >NOMe | H | 4-HOOCPh |
| 1-57 | CH | >NOMe | H | 3-FPh |
| 1-58 | CH | >NOEt | H | 4-FPh |
| 1-59 | CH | >NOAll | H | 4-CNPh |
| 1-60 | CH | >NOPrg | H | 3-CNPh |
| 1-61 | CH | >NOCH$_2$COOH | H | 3-FPh |
| 1-62 | CH | >NOCH$_2$COOH | H | 3-CNPh |
| 1-63 | CH | >NOCH$_2$COOH | H | 3-TfmPh |
| 1-64 | CH | >NOCMe$_2$COOH | H | 4-TfmPh |
| 1-65 | N | >NOH | H | Ph |
| 1-66 | N | >NOH | H | 3-CNPh |
| 1-67 | N | >NOH | H | 3-FPh |
| 1-68 | N | >NOH | H | 4-TfmPh |
| 1-69 | N | >NOH | H | 3-MeSO$_2$Ph |
| 1-70 | N | >NOH | H | 4-MeSO$_2$Ph |
| 1-71 | N | >NOMe | H | 3-TfmPh |
| 1-72 | CH | >NOH | PivOMe | 3-CNPh |
| 1-73 | CH | >NOEtc | PivOMe | 3-FPh |
| 1-74 | CH | >NOiPrc | 1-iPrcOEt | 3-CNPh |
| 1-75 | CH | >NO(MeCar) | PivOMe | 4-TfmPh |
| 1-76 | CH | >NOMec | iPrcOMe | 4-MesPh |
| 1-77 | CH | >NOCOOcHx | Dox | Ph |
| 1-78 | CH | >NODox | Dox | 3-CNPh |
| 1-79 | CH | >NOCH$_2$COOH | 1-(cHxOOCO)Et | 3-(CNCH$_2$)Ph |
| 1-80 | CH | >CHCl | H | 3-CNPh |
| 1-81 | CH | >CHCl | H | 4-FPh |
| 1-82 | CH | >CHCl | H | 4-CNPh |
| 1-83 | CH | >CHCl | PivOMe | 3-FPh |
| 1-84 | CH | >CHCl | J-(iByrO)Et | 3-TfmPh |
| 1-85 | CH | >NOH | H | 4-AcNHPh |
| 1-86 | CH | >NOH | H | 3,4,5-triMeOPh |
| 1-87 | CH | >NOH | H | 4-MesNHPh |
| 1-88 | CH | >NOH | H | 2-TfmPh |
| 1-89 | CH | >CHEt | H | 4-MeSOPh |
| 1-90 | CH | >CHEt | H | 3-FPh |
| 1-91 | CH | >CHEt | H | 3-CNPh |
| 1-92 | CH | >NOCH$_2$CN | H | 4-MeSOPh |
| 1-93 | CH | >NOCH$_2$CN | H | 3-FPh |
| 1-94 | CH | >NOCHF$_2$ | H | 3-FPh |
| 1-95 | CH | >NOCHF$_2$ | H | 4-MeSOPh |
| 1-96 | CH | >NOCHF$_2$ | H | 3-CNPh |
| 1-97 | CH | >NOCH$_2$F | H | 4-MeSOPh |
| 1-98 | CH | >NOCH$_2$F | H | 3-FPh |
| 1-99 | CH | >NOCH$_2$F | H | 3-CNPh |
| 1-100 | CH | >NOByr | PivOMe | 3-FPh |
| 1-101 | CH | >NOCH$_2$F | PivOMe | 3-FPh |
| 1-102 | CH | >NO(2-NH$_2$Etc) | PivOMe | 3-FPh |
| 1-103 | CH | >NOH | (2-NH$_2$Etc)OMe | 3-FPh |
| 1-104 | CH | >NOH | (HOOC.Mec)OMe | 3-CNPh |
| 1-105 | CH | >NOH | (HOOC.Mec)OMe | 3-FPh |
| 1-106 | CH | >NOCH$_2$F | (2-HOOC.Etc)oMe | 3-FPh |
| 1-107 | CH | >NOCH$_2$F | (2-HOOC.Etc)OMe | 4-MeSOPh |
| 1-108 | CH | >NOCH$_2$F | (3-HOOC.Prc)OMe | 4-MeSOPh |
| 1-109 | N | >NOCH$_2$F | H | 4-MeSOPh |
| 1-110 | N | >NOCH$_2$F | H | 3-FPh |
| 1-111 | N | >NOCH$_2$F | H | 4-AcNHPh |
| 1-112 | CH | >NOBoz | PivOMe | 3-FPh |
| 1-113 | CH | >NOCH$_2$F | (2-NH$_2$Etc)OMe | 4-MeSOPh |
| 1-114 | CH | >NOCH$_2$F | (2-NH$_2$Etc)OMe | 3-FPh |
| 1-115 | CH | >NOCH$_2$F | I-iPrcOEt | 3-CNPh |
| 1-116 | CH | >NO(2-NH$_2$Et) | H | 4-MeSOPh |
| 1-117 | CH | >NO(2-NH$_2$Et) | PivOMe | 4-MeSOPh |
| 1-118 | CH | >NO(2-NH$_2$Et) | H | 3-FPh |

TABLE 1-continued

| Cpd No. | Q | X | R$^a$ | Ar |
|---|---|---|---|---|
| 1-119 | CH | >NO(2-NH$_2$Et) | PivOMe | 3-FPh |
| 1-120 | CH | >NO(2-NH$_2$-2-HOOCEt) | H | 4-MeSOPh |
| 1-121 | CH | >NO(2-NH$_2$-2-HOOCEt) | H | 3-FPh |
| 1-122 | CH | >NO(2-MeNHEt) | H | 4-MeSOPh |
| 1-123 | CH | >NO(2-MeNHEt) | H | 3-FPh |
| 1-124 | CH | >NO(2-Me$_2$NEt) | H | 4-MeSoPh |
| 1-125 | CH | >NO(2-Me$_2$NEt) | H | 3-FPh |
| 1-126 | CH | >NOH | (HOOC.CH$_2$—CarO)Me | 4-MeSOPh |
| 1-127 | CH | >NOH | (HOOC.CH$_2$—CarO)Me | 3-FPh |
| 1-128 | CH | >NO(α-HOOC-3,4-diHOBz) | (HOOC.CH$_2$—CarO)Me | 4-MeSOPh |
| 1-129 | CH | >NO(α-HOOC-3,4-diHOBz) | (HOOC.CH$_2$—CarO)Me | 3-FPh |

TABLE 2

| Cpd No. | R$^1$ | Ar |
|---|---|---|
| 2-1 | α-NH$_2$-α-PhAc | 3-FPh |
| 2-2 | α-NH$_2$-α-PhAc | 4-MeSOPh |
| 2-3 | α-NH$_2$-α-PhAc | 3-CNPh |
| 2-4 | α-NH$_2$-α-(4-HOPh)Ac | 3-FPh |
| 2-5 | α-NH$_2$-α-(4-HOPh)Ac | 4-MeSOPh |
| 2-6 | α-NH$_2$-α-(4-HOPh)Ac | 3-CNPh |
| 2-7 | α-HO-α-PhAc | 3-FPh |
| 2-8 | α-HO-α-PhAc | 4-MeSOPh |
| 2-9 | α-HO-α-PhAc | 3-CNPh |
| 2-10 | α-FoO-α-PhAc | 3-FPh |
| 2-11 | α-FoO-α-PhAc | 4-MeSOPh |
| 2-12 | α-FoO-α-PhAc | 3-CNPh |
| 2-13 | α-Sfo-α-PhAc | 3-FPh |
| 2-14 | α-Sfo-α-PhAc | 4-MeSOPh |
| 2-15 | α-Sfo-α-PhAc | 3-CNPh |
| 2-16 | α-HOOC-α-(4-HoPh)Ac | 3-FPh |
| 2-17 | α-HOOC-α-(4-HOPh)Ac | 4-MeSOPh |
| 2-18 | α-HOOC-α-(4-HoPh)Ac | 3-CNPh |
| 2-19 | α-(4-HONicNH)-α-(4-HOPh)Ac | 3-FPh |
| 2-20 | α-(4-HONicNH)-α-(4-HOPh)Ac | 4-MeSOPh |
| 2-21 | α-(4-HONicNH)-α-(4-HOPh)Ac | 3-CNPh |
| 2-22 | α-(4-Et-2,3-dioxo-1-PizCONH)-α-(4-HOPh)Ac | 3-FPh |
| 2-23 | α-(4-Et-2,3-dioxo-1-PizCONH)-α-(4-HOPh)Ac | 4-MeSOPh |
| 2-24 | α-(4-Et-2,3-dioxo-1-PizCONH)-α-(4-HOPh)Ac | 3-CNPh |
| 2-25 | α-(2-NH$_2$CH$_2$-Ph)Ac | 3-FPh |
| 2-26 | α-(2-NH$_2$CH$_2$-Ph)Ac | 4-MeSOPh |
| 2-27 | α-(2-NH$_2$CH$_2$-Ph)Ac | 3-CNPh |
| 2-28 | α-NH$_2$-α-cyclohexα-1,4-dienyl-Ac | 3-FPh |
| 2-29 | α-NH$_2$-α-cyclohexα-1,4-dienyl-Ac | 4-MeSOPh |
| 2-30 | α-NH$_2$-α-cyclohexα-1,4-dienyl-Ac | 3-CNPh |
| 2-31 | NCAc | 3-FPh |
| 2-32 | NCAc | 4-MeSOPh |
| 2-33 | NCAc | 3-CNPh |
| 2-34 | 2-ThiAc | 3-FPh |
| 2-35 | 2-ThiAc | 4-MeSOPh |
| 2-36 | 2-ThiAc | 3-CNPh |
| 2-37 | α-(MeO.N=)-α-(2-Fur)Ac | 3-FPh |
| 2-38 | α-(MeO.N=)-α-(2-Fur)Ac | 4-MeSOPh |
| 2-39 | α-(MeO.N=)-α-(2-Fur)Ac | 3-CNPh |
| 2-40 | (2-NH$_2$-4-Thiz)Ac | 3-FPh |
| 2-41 | (2-NH$_2$-4-Thiz)Ac | 4-MeSoPh |
| 2-42 | (2-NH$_2$-4-Thiz)Ac | 3-CNPh |
| 2-43 | 2-(2-NH$_2$-4-Thiz)-4-HOOC.iCro | 3-FPh |
| 2-44 | 2-(2-NH$_2$-4-Thiz)-4-HOOC.iCro | 4-MeSOPh |
| 2-45 | 2-(2-NH$_2$-4-Thiz)-4-HOOC.iCro | 3-CNPh |
| 2-46 | α-(2-NH$_2$-4-Thiz)-α-(FoNH)Ac | 3-FPh |
| 2-47 | α-(2-NH$_2$-4-Thiz)-α-(FoNH)Ac | 4-MeSOPh |
| 2-48 | α-(2-NH$_2$-4-Thiz)-α-(FoNH)Ac | 3-CNPh |
| 2-49 | 4-PyrSAc | 3-FPh |
| 2-50 | 4-PyrSAc | 4-MeSOPh |
| 2-51 | 4-PyrSAc | 3-CNPh |
| 2-52 | Tez$_1$Ac | 3-FPh |
| 2-53 | Tez$_1$Ac | 4-MeSOPh |
| 2-54 | Tez$_1$Ac | 3-CNPh |

TABLE 3

| Cpd. No. | R$^1$ | Ar |
|---|---|---|
| 3-1 | F$_2$CHSAc | 3-FPh |
| 3-2 | F$_2$CHSAc | 4-MeSOPh |
| 3-3 | F$_2$CHSAc | 3-CNPh |
| 3-4 | NC.CH$_2$SAc | 3-FPh |
| 3-5 | NC.CH$_2$SAc | 4-MeSOPh |
| 3-6 | NC.CH$_2$SAc | 3-CNPh |
| 3-7 | (2-NH$_2$-2-HOOC.EtS)Ac | 3-FPh |
| 3-8 | (2-NH$_2$-2-HOOC.EtS)Ac | 4-MeSOPh |
| 3-9 | (2-NH$_2$-2-HOOC.EtS)Ac | 3-CNPh |
| 3-10 | 4-(α-Car-α-HOOC-methylene)-1,3-dithietanyl.CO— | 3-FPh |
| 3-11 | 4-(α-Car-α-HOOC-methylene)-1,3-dithietanyl.CO— | 4-MeSOPh |
| 3-12 | 4-(α-Car-α.-HOOC-methylene)-1,3-dithietanyl.CO— | 3-CNPh |

TABLE 4

| Cpd No. | Q | x | R$^a$ | Ar |
|---|---|---|---|---|
| 4-1 | CH | >NOH | H | 3-FPh |
| 4-2 | CH | >NOH | H | 3,4-diFPh |
| 4-3 | CH | >NOH | H | 3-CNPh |
| 4-4 | CH | >NOH | H | 4-MeSOPh |
| 4-5 | CH | >NOH | H | 4-AcPh |

Of the compounds listed above, the preferred compounds are those of Table 1. More preferred compounds are Compounds No. 1-8, 1-11, 1-19, 1-30, 1-46, 1-47, 1-57, 1-60, 1-61, 1-62, 1-66, 1-67, 1-72, 1-73, 1-74, 1-78, 1-80, 1-83, 1-85, 1-86, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128 and 1-129, and the most preferred compounds are:

1-8. 7-[2-(2-Aminothiazol-4-yl)-2-(syn-hydroxyimino)acetamido]-3-(3-fluorophenoxy)methyl-3-cephem-4-carboxylic acid;

1-11. 7-[2-(2-Aminothiazol-4-yl)-2-(syn-hydroxyimino)acetamido]-3-(3,4-difluorophenoxy)methyl-3-cephem-4-carboxylic acid;

1-19. 7-[2-(2-Aminothiazol-4-yl)-2-(syn-hydroxyimino)acetamido]-3-(3-cyanophenoxy)methyl-3-cephem-4-carboxylic acid;

1-30. 7-[2-(2-Aminothiazol-4-yl)-2-(syn-hydroxyimino)acetamido]-3-(4-methanesulfinylphenoxy)-methyl-3-cephem-4-carboxylic acid;

1-46. 7-[2-(2-Aminothiazol-4-yl)-2-(syn-hydroxyimino)acetamido]-3-(4-acetylphenoxy)methyl-3-cephem-4-carboxylic acid;

1-47. 7-[2-(2-Aminothiazol-4-yl)-2-(syn-hydroxyimino)acetamido]-3-(4-acetyl-3-hydroxyphenoxy)-methyl-3-cephem-4-carboxylic acid;

1-85. 7-[2-(2-Aminothiazol-4-yl)-2-(syn-hydroxyimino)acetamido] -3-(4-acetamidophenoxy)methyl-3-cephem-4-carboxylic acid;

1-86. 7-[2-(2-Aminothiazol-4-yl)-2-(syn-hydroxyimino)acetamido]-3-(3,4,5-trimethoxyphenoxy)-methyl-3-cephem-4-carboxylic acid;

and pharmaceutically acceptable salts and esters thereof.

For use as intermediates, we also prefer the 7-amino analogs of the compounds referred to above.

In general terms, the compounds of formula (I) in which $R^1$ represents one of the aforementioned acyl groups, that is to say compounds of formula (II):

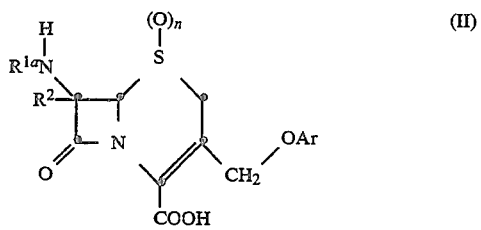

(II)

[in which: Ar, $R^2$ and n are as defined above; and $R^{1a}$ represents a $C_1$-$C_{10}$ alkanoyl group; a $C_1$-$C_{10}$ alkanoyl group having at least one substituent selected from the group consisting of substituents (a), defined above; a $C_3$-$C_{10}$ alkenoyl group; a $C_3$-$C_{10}$ alkenoyl group having at least one substituent selected from the group consisting of substituents (a), defined above; a $C_3$-$C_6$ alkynoyl group; a carbocyclic aromatic carboxylic acyl group having from 7 to 11 carbon atoms which is unsubstituted or has at least one substituent selected from the group consisting of substituents (b), defined above; a group of formula Het—CO— in which Het represents a heterocyclic group having from 4 to 7 ring atoms of which from 1 to 4 are hetero-atoms selected from the group consisting of nitrogen, oxygen and sulfur heteroatoms and is unsubstituted or has at least one substituent selected from the group consisting of substituents (c), defined above; or a cycloalkyl-carbonyl group in which the cycloalkyl part has from 3 to 7 ring carbon atoms and is unsubstituted or has at least one substituent selected from the group consisting of substituents (b), defined above], may be prepared by acylation of the corresponding 7-amino compound of formula (III):

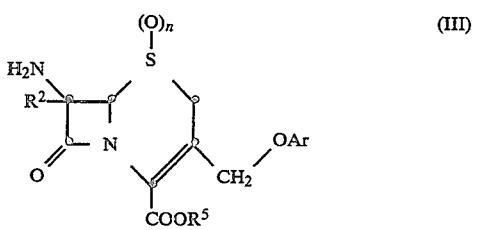

(III)

(in which Ar, $R^2$ and n are as defined above and $R^5$ represents a hydrogen atom or a carboxy-protecting group) with an acid of formula $R^{1a}$—OH ($R^{1a}$ is as defined above) or with an active derivative thereof.

The compound of formula (III), defined above, may be prepared by reacting a compound of formula (IV):

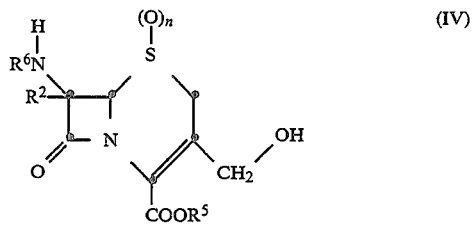

(IV)

(in which $R^2$, $R^5$ and n are as defined above and $R^6$ represents an amino-protecting group) with a compound of formula Ar—OH (in which Ar is as defined above) or with such a compound in which any reactive groups are protected in the presence of triphenylphosphine and of an azodicarboxylic acid ester, and, if required, removing any protecting groups.

In the case of those compounds of formula (II) and (III) where $R^2$ represents a $C_1$-$C_6$ alkoxy group, these may be perpared from the corresponding compound where $R^2$ represents a hydrogen atom by conventional means. For example as described in U.S. Pat. No. 4,051,320 or 4,048,155, the disclosures of which are incorporated herein by reference.

In more detail, the compounds of the invention may be prepared as shown in the following Reaction Scheme:

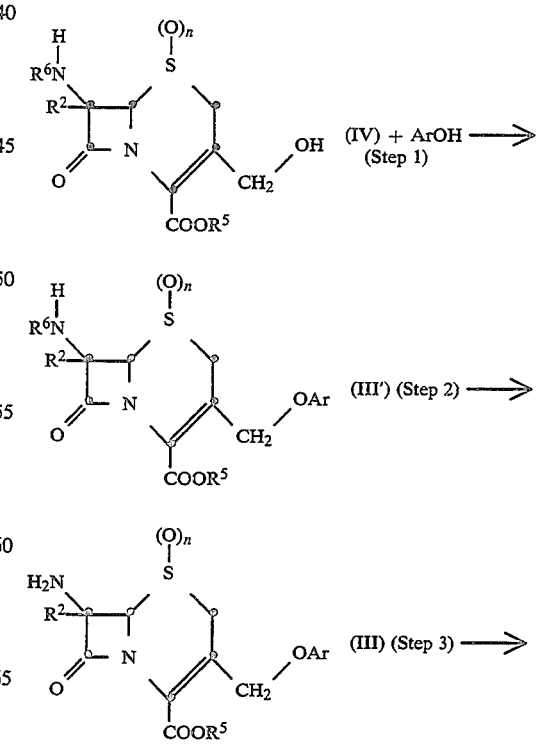

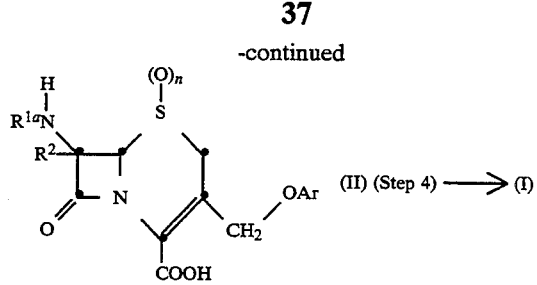

(II) (Step 4) ⟶ (I)

In the above formulae, $R^{1a}$, $R^2$, $R^5$, $R^6$, Ar and n are as defined above.

In the preferred compounds of the present invention, where $R^{1a}$ represents an aminothiazolyl or aminothiadiazolyl group, we prefer that the amino group should also be protected. In this case, the protecting group used may be the same as or different from the protecting group used to protect the 7-amino group in the compound of formula (IV).

Where the above compounds contain a hydroxyimino group, this is preferably also protected.

Examples of amino-protecting groups which may be represented by $R^6$ and which may be used to protect any other amino group in the above compounds include various acyl, substituted oxycarbonyl, allyl and substituted methyl groups.

Examples of suitable acyl groups include the phthaloyl group, the succinyl group, the benzoyl and substituted benzoyl groups (such as the benzoyl, 4-methoxybenzoyl and 4-nitrobenzoyl groups), the formyl group, the acetyl and substituted acetyl groups (such as the acetyl, chloroacetyl, bromoacetyl, phenylacetyl and phenoxyacetyl groups) and other alkanoyl groups (such as the propionyl, butyryl and pivaloyl groups).

Examples of suitable substituted oxycarbonyl groups, include the benzyloxycarbonyl and substituted benzyloxycarbonyl groups (such as the benzyloxycarbonyl, 4-methoxybenzyloxycarbonyl and 4-nitrobenzyloxycarbonyl groups), alkoxycarbonyl groups (such as the t-butoxycarbonyl group) and the-allyloxycarbonyl group.

Examples of suitable substituted methyl groups include the triphenylmethyl group.

Examples of suitable carboxy-protecting groups which may be represented by $R^5$ include the benzhydryl group, the t-butyl group, the benzyl group, the 4-nitrobenzyl group, the 4-methoxybenzyl group, the trimethylsilyl group and the t-butyldimethylsilyl group.

Examples of suitable hydroxy-protecting groups, which may be used to protect the hydroxyimino group, include the triphenylmethyl group, the t-butyl group and the benzyloxycarbonyl group.

It will, however, be appreciated that all of these protecting groups are well known in the art and that they may be replaced by other, and equally well known, protecting groups, as will be readily apparent to those skilled in the art.

In Step 1, the compound of formula (III') can be prepared from the compound of formula (IV) by reaction with the compound of formula ArOH in the presence of triphenylphosphine and of an azodicarboxylic acid ester. The reaction is normally and preferably effected in the presence of a suitable solvent. There is no particular restriction on the nature of the solvent to be employed, provided that it has no adverse effect on the reaction or on the reagents involved. Examples of suitable solvents include: ethers, such as dioxane, tetrahydrofuran and diethyl ether; halogenated hydrocarbons, especially halogenated aliphatic hydrocarbons, such as methylene chloride or 1,2-dichloroethane; esters, such as ethyl acetate; and amides, especially fatty acid amides, such as N,N-dimethylformamide. The reaction can take place over a wide range of temperatures, and the precise reaction temperature is not critical to the invention. In general, we find it convenient to carry out the reaction at a temperature from −20° C. to 90° C. The time required for the reaction may also vary widely, depending on many factors, notably the reaction temperature and the nature of the reagents. However, provided that the reaction is effected under the preferred conditions outlined above, a period of from 0.1 to 8 hours will usually suffice.

The product obtained as described above may be purified by conventional means, if required, prior to being used in the subsequent Step.

If required, the product of this Step, the compound of formula (III') where n is 0 may be converted to a compound of formula (III') where n is 1 by oxidation with a suitable reducing agent. The reducing agent is preferably a peracid. Examples of peracids which may be used in this reaction include m-chloroperbenzoic acid and peracetic acid. The reaction is preferably effected in the presence of a solvent, and there is no particular restriction on the nature of the solvent to be employed, provided that it has no adverse effect on the reaction or on the reagents involved. Examples of suitable solvents include: water; ketones, such as acetone; ethers, such as tetrahydrofuran; nitriles, such as acetonitrile; esters, such as ethyl acetate; amides, especially fatty acid amides, such as dimethylformamide or dimethylacetamide; and mixtures of any two or more of these solvents. The reaction can take place over a wide range of temperatures, and the precise reaction temperature is not critical to the invention. In general, we find it convenient to carry out the reaction at a temperature from −70° C. to 30° C. The time required for the reaction may also vary widely, depending on many factors, notably the reaction temperature and the nature of the reagents. However, provided that the reaction is effected under the preferred conditions outlined above, a period of from 0.5 to 24 hours will usually suffice.

Alternatively, if desired, a compound in which n is 0 may be converted to a corresponding compound in which n is 1 by the same reaction at any subsequent stage of this sequence of reactions.

In Step 2, the amino protecting group $R^6$ is removed. The nature of the reaction employed to remove this group will, of course, depend on the nature of the group to be removed, as is well known in the art. For example, where the protecting group is an acyl group, it can be removed by treatment with an iminohalogenating agent and subsequently alcohol followed by hydrolysis [J. Antibiotic, 40, 380 (1987)]. Where the protecting group is a haloacyl group, it can be removed by treatment with thiourea or with sodium N-methyldithiocarbamate [T. W. Greene; Protective Groups in Organic Synthesis, J. E. Wiley & Sons ed., 269 (1981); Japanese Patent Provisional Publication Tokkai No. Sho 63-152389 (1988)]. Where the protecting group is a phthaloyl or succinyl group, it can be removed by treatment with hydrazine [T. W. Greene; Protective Groups in Organic Synthesis, J. E. Wiley & Sons ed., 265 (1981)]. Where the protecting group is a substituted oxycarbonyl group, it can be removed by treatment with an acid or with a reducing agent [T. W. Greene; Protective Groups in Organic Synthesis, J. E. Wiley & Sons ed., 223-248 (1981)]. Where the protecting group is an allyl or allyloxycarbonyl group, it can be removed by treatment with palladium-triphenylphosphine or with tetrakis(triphenylphosphine)palladium-triphenylphosphine [T. W. Greene; Protective Groups in Organic Synthesis, J. E. Wiley & Sons ed., 235 (1981); J. Org. Chem., 47, 587 (1982)]. Where the protecting group is a triphenylmethyl group or a formyl group, it can be removed by treatment with an acid [T. W. Greene; Protective Groups in Organic Synthesis, J. E. Wiley & Sons ed., 247 and 250 (1981)].

In Step 3, a compound of formula (II) is prepared from the compound of formula (III) by reaction with an acylating agent. This acylating agent may be an acid of formula $R^{1a}$—OH (where $R^{1a}$ is as defined above) or it may be a reactive derivative of the carboxylic acid. The reaction is preferably effected in the presence of a suitable solvent. There is no particular restriction on the nature of the solvent to be employed, provided that it has no adverse effect on the reaction or on the reagents involved. Examples of suitable solvents include: ethers, such as acetone, dioxane or tetrahydrofuran; esters, such as ethyl acetate, halogenated hydrocarbons, especially halogenated aliphatic hydrocarbons, such as methylene chloride, 1,2-dichloroethane or chloroform; nitriles such as acetonitrile; and amides such as N,N-dimethylformamide or N,N-dimethylacetamide.

The reaction can take place over a wide range of temperatures, and the precise reaction temperature is not critical to the invention. In general, we find it convenient to carry out the reaction at a temperature from −30° C. to 90° C. The time required for the reaction may also vary widely, depending on many factors, notably the reaction temperature and the nature of the reagents. However, provided that the reaction is effected under the preferred conditions outlined above, a period of from 0.1 to 8 hours will usually suffice.

Especially where the acylating agent is the free carboxylic acid, we prefer that the reaction should be effected in the presence of a condensing agent. Suitable condensing agents for use in the reaction include dicyclohexylcarbodiimide and 2-ethoxy-1-(2H)-quinolinecarboxylic acid esters.

Apart from the acid itself, it is also possible to use a reactive derivative of the acid. Examples of suitable reactive derivatives include: an acid halide, an acid anhydride, an activated amide or an activated ester. Of the acid halides, we prefer acid chlorides and acid bromides; the acid anhydride may, for example, be a mixed anhydride of isobutylformic acid and the compound of formula $R^{1a}$—OH; the activated amide may, for example, be an amide of the compound of formula $R^{1a}$—OH with a 4-substituted imidazole, dimethylpyrazole, benzotriazole or tetrazole; and the activated ester may, for example, be an ester of the compound of formula $R^{1a}$—OH with 4-nitrophenol, 1-hydroxy-1H-benzotriazole, 1-hydroxy-6-chloro-1H-benzotriazole, mercaptopyridine, 2-mercaptobenzothiazole or 4-nitrothiophenol.

The reaction can be and may preferably be performed in the presence of an alkali. There is no particular restriction on the nature of the alkali employed, provided that it does not have any adverse effect on other parts of the molecule, especially the β-lactam ring; suitable alkalis include: alkali metal carbonates, such as sodium carbonate; and tertiary amines, such as N,N-diethylaniline or triethylamine.

If the compound of formula (II) contains a protected amino group, the protecting group is removed after Step 3. The reactions employed to remove this protecting group are the same as those employed in Step 2.

In Step 4, where the compound contains a protected hydroxyimino group, this protecting group is removed, as is also the carboxy-protecting group represented by $R^5$. The reactions in this Step can be carried out in a manner well known in the art, and the exact nature of each removal reaction will depend on the nature of the protecting group to be removed.

Removal of the hydroxy-protecting group

Where the protecting group is a triphenylmethyl or t-butyl group, it can be removed by treatment with an acid [T. W. Greene; Protective Groups in Organic Synthesis, J. E. Wiley & Sons ed., 35 and 26 (1981)]. Where the protecting group is a benzyloxycarbonyl group, it can be removed by treatment with nitromethanealuminum chloride [T. W. Greene; Protective Groups in Organic Synthesis, J. E. Wiley & Sons ed., 68 (1981)].

Removal of a carboxy-protecting group

Where the protecting group is a benzhydryl or t-butyl group, it can be removed by treatment with an acid [T. W. Greene; Protective Groups in Organic Synthesis, J. E. Wiley & Sons ed., 174 and 168 (1981)]. Where the protecting group is a benzyl, 4-methoxybenzyl or 4-nitrobenzyl group, it can be removed by reduction or by treatment with nitromethane-aluminum chloride [T. W. Greene; Protective Groups in Organic Synthesis, J. E. Wiley & Sons ed., 171-172(1981)].

A compound of formula (II), in which $R^{1a}$ represents an alkyl group having a =NOR$^3$ substituent (where $R^3$ represents an acyl, oxycarbonyl or optionally substituted carbamoyl group) may be prepared from the corresponding compound of formula (II), in which $R^3$ represents a hydrogen atom [which itself may be also prepared by removing a hydroxy-protecting group from a protected hydroxyimino group] by reacting the hydroxyimino compound with a compound of formula ClCOR$^7$, ClCOOR$^8$ or $R^9R^{10}$N=C=O, in which:

$R^7$ represents an optionally substituted $C_1$-$C_6$ aliphatic carboxylic acyl group; an aromatic carboxylic acyl group; or a group of formula Het—CO— in which Het is as defined above; all as defined above in relation to $R^3$;

$R^8$ represents a $C_1$-$C_6$ alkyl group; a $C_3$-$C_7$ cycloalkyl group; a $C_6$-$C_{10}$ aryl group which is unsubstituted or has at least one substituent selected from the group consisting of substituents (e), defined below; or an aralkyl group in which the alkyl part is $C_1$-$C_4$ and the or each aryl part is $C_6$-$C_{10}$ and is unsubstituted or has at least one substituent selected from the group consisting of substituents (e), defined below;

$R^9$ and $R^{10}$ are independently selected from the group consisting of hydrogen atoms and $C_1$-$C_6$ alkyl groups;

by conventional means.

In more detail, a compound of formula (II), in which $R^3$ represents a group of formula —COR$^7$ or —COOR$^8$, can be prepared by reacting the corresponding compound of formula (II) in which $R^3$ represents a hydrogen atom, with a compound of formula ClCOR$^7$ or ClCOOR$^8$ in the presence of a solvent and of a base. There is no particular restriction on the nature of the solvent to be employed, provided that it has no adverse effect on the reaction or on the reagents involved. Examples of suitable solvents include: aliphatic hydrocarbons, such as hexane; ethers; such as tetrahydrofuran, 1,2-dimethoxyethane or dioxane; and halogenated hydrocarbons, especially halogenated aliphatic hydrocarbons, such as methylene chloride or chloroform. The reaction can take place over a wide range of temperatures, and the precise reaction temperature is not critical to the invention. In general, we find it convenient to carry out the reaction at a temperature from −20° C. to 50° C. The time required for the reaction may also vary widely, depending on many factors, notably the reaction temperature and the nature of the reagents. However, provided that the reaction is effected under the preferred conditions outlined above, a period of from 0.1 to 5 hours will usually suffice. Examples of the base which may be used in the reaction include triethylamine, pyridine and N,N-diethylaniline.

A compound of formula (II) in which $R^3$ represents a group of formula —$CONR^9R^{10}$ can be prepared by reacting the corresponding compound of formula (II) in which $R^3$ represents a hydrogen atom with a compound of formula $R^9R^{10}N=C=O$ in the presence of a solvent. There is no particular restriction on the nature of the solvent to be employed, provided that it has no adverse effect on the reaction or on the reagents involved. Examples of suitable solvents include: aliphatic hydrocarbons, such as hexane; ethers, such as tetrahydrofuran, 1,2-dimethoxyethane or dioxane; amides, particularly fatty acid amides, such as dimethylformamide or dimethylacetamide; and halogenated hydrocarbons, especially halogenated aliphatic hydrocarbons, such as methylene chloride or chloroform. The reaction can take place over a wide range of temperatures, and the precise reaction temperature is not critical to the invention. In general, we find in convenient to carry out the reaction at a temperature from 0° to 100° C. The time required for the reaction may also vary widely, depending on many factors, notably the reaction temperature and the nature of the reagents. However, provided that the reaction is effected under the preferred conditions outlined above, a period of from 0.1 to 10 hours will usually suffice.

Where the compound contains an alkylthio or arylthio group, this may be converted to the corresponding alkylsulfinyl, alkylsulfonyl, arylsulfinyl or arylsulfonyl group by oxidation, using methods well known to those skilled in the art. In particular, the oxidation may be carried out using the oxidizing agents and conditions described above for oxidising a compound where n is 0 to a compound where n is 1.

Salts and esters of the compounds of formula (I) may be preapred by conventional salification and esterification techniques, which are well known to those skilled in the art of β-lactam antibiotics.

The compounds of the present invention exhibit outstanding antibacterial activity with a wide spectrum of activity, and they are also resistant to β-lactamase. As assessed by the agar plate dilution method, they have been shown to be active against a wide range of pathogenic microorganisms, including both Gram-positive bacteria (such as *Staphylococcus aureus* and *Bacillus subtilis*) and Gram-negative bacteria (such as *Escherichia coli*, *Shigella flexneri*, *Klebsiella pneumoniae*, *Proteus vulgaris*, *Serratia* species e.g. *Serratia marcescens*, *Enterobacter* species e.g. *Enterobacter cloacae*, *Salmonella enteritidis* and *Pseudomonas aeruginosa*) and are thus very useful for the treatment of diseases caused by such microorganisms in humans and non-human animals. In particular, they have been found to be active against methicillin-resistant staphylococcus, which is a development of potentially enormous impotrance. They also exhibit low toxicity when tested in laboratory animals.

Table 6 sets out the activities of several of the compounds of the present invention against various bacteria, in terms of their minimal inhibitory concentrations (μg/ml). In this Table, each of the compounds of the invention is identified both by the number assigned to it in the appropriate one of foregoing Tables 1 to 5 and by the number of the subsequent Example which illustrates its preparation.

TABLE 6

| Cpd No. | Cpd of Ex. No. | A | B | C | D |
|---|---|---|---|---|---|
| 8 | 3 | <0.01 | 0.05 | 0.8 | 0.8 |
| 11 | 10 | <0.01 | 0.05 | 1.5 | 1.5 |
| 19 | 12 | <0.01 | 0.1 | 0.4 | 0.8 |
| 30 | 57 | 0.02 | 0.1 | 0.1 | 0.4 |
| 46 | 13 | <0.01 | 0.05 | 0.4 | 0.8 |
| 47 | 22 | <0.01 | <0.01 | 0.8 | 0.8 |
| 85 | 52 | <0.01 | 0.1 | 0.2 | 0.4 |
| 86 | 51 | 0.02 | 0.2 | 0.2 | 0.8 |

In the above Table, the microorganisms are:
A: *Staphylococcus aureus* 209 (S)
B: *Staphylococcus aureus* 569 (R)
C: *Escherichia coli* NIHJ (S)
D: *Escherichia coli* NIHJ (R)

The results given above indicate that the compounds of the present invention may be used to treat or prevent diseases caused by a wide range of pathogenic bacteria.

The compounds of the invention may be administered either orally or parenterally for the treatment of diseases in humans and other animals, especially mammals, caused by pathogenic microorganisms. The compounds may be formulated into any conventional forms for administration. For example, for oral administration, suitable formulations include tablets, granules, capsules, powders and syrups, whilst formulations for parenteral administration include injectable solutions for intramuscular or, more preferably intravenous, injection.

The dose of the compound of the invention will vary, depending upon the age, body weight and condition of the patient, as well as upon the form and times of administration. However, in general the adult daily dose is expected to be from 250 to 3000 mg of the compound, which may be administered in a single dose or in divided doses.

The preparation of certain of the compounds of the present invention is illustrated by the following Examples.

EXAMPLE 1

7-[2-(2-Aminothiazol-4-yl)-2-(syn-hydroxyimino)acetamido]-3-phenoxymethyl-3-cephem-4-carboxylic acid trifluoroacetate 1(a) Diphenylmethyl 7-phenoxyacetamido-3-phenoxymethyl-3-cephem-4-carboxylate A solution of 0.55 ml of dimethyl azodicarboxylate in 40 ml of tetrahydrofuran was added dropwise, over a period of 15 minutes, to a solution of 2.00 g of diphenylmethyl 7-phenoxyacetamido-3-hydroxymethyl-3-cephem-4-carboxylate, 990 mg of triphenylphosphine and 430 mg of phenol in 40 ml of tetrahydrofuran, whilst ice-cooling and stirring. After stirring the mixture for a further 15 minutes, whilst ice-cooling, the reaction mixture was diluted with ethyl acetate and washed with a saturated aqueous solution of sodium chloride. The ethyl acetate solution was then dried over anhydrous sodium sulfate and concentrated by distilling off the solvent under reduced pressure. The resulting residue was purified by column chromatography through silica gel, to afford 250 mg of the title compound as a powder.
Nuclear Magnetic Resonance Spectrum (CDCl$_3$) δ ppm: 3.62 (2H, singlet); 4.57 (2H, singlet); 4.82 (1H, doublet. J=14 Hz); 4.97 (1H, doublet, J=14 Hz); 5.03 (1H, doublet, J=5 Hz); 5.96 (1H, doublet of doublets, J=5 & 9 Hz); 6.7–7.5 (22H. multiplet).

1(b) Diphenylmethyl 3-phenoxymethyl-7-[2-(2-tritylaminothiazol-4-yl)-2-(syn-trityloxyimino)acetamido]-3-cephem-4-carboxylate 0.36 ml of pyridine was added dropwise to a solution of 800 mg of phosphorus pentachloride in 18 ml of chloroform at room temperature, and then the mixture was stirred for 15 minutes. A solution of 1.00 g of diphenylmethyl 7-phenoxyacetamido-3-phenoxymethyl-3-cephem-4-carboxylate [prepared as described in step (a) above] in 8 ml of chloroform was then added dropwise to the mixture, whilst ice-cooling and stirring, and then the mixture was stirred at 15° C. for 1 hour. At the end of this time, the reaction mixture was cooled to −30° C. and mixed with 2.2 ml of propyl alcohol, and then it was allowed to warm gradually to room temperature. The reaction mixture was then diluted with methylene chloride, after which it was washed with a saturated aqueous solution of sodium chloride and dried over anhydrous sodium sulfate. The solvent was then stripped from the solution by distillation under reduced pressure. The resulting residue was washed with diisopropyl ether to afford the hydrochloride of diphenylmethyl 7-amino-3-phenoxymethyl-3-cephem-4-carboxylate as a powder.

1.2 ml of diethylaniline, 1.30 g of 2-(syn-trityloxyimino)-2-(2-tritylaminothiazol-4-yl)acetic acid and 0.18 ml of phosphorus oxychloride were then added, in that order to a solution of the hydrochloride in 20 ml of methylene chloride, whilst ice-cooling and stirring. After stirring the reaction mixture at the same temperature for 30 minutes, it was diluted with ethyl acetate, and the resulting solution was washed with 3.5% v/v aqueous hydrochloric acid, a 5% w/v aqueous solution of sodium bicarbonate and a saturated aqueous solution of sodium chloride, in that order. The organic layer was then dried over anhydrous sodium sulfate, after which the solvent was distilled off under reduced pressure. The resulting residue was purified by column chromatography through silica gel, to afford 1.19 g of the title compound as a powder.
Nuclear Magnetic Resonance Spectrum (CDCl$_3$) δ ppm: 3.40 (1H, doublet, J=19 Hz); 3.55 (1H, doublet, J=19 Hz); 4.80 (1H, doublet, J=14 Hz); 5.00 (1H, doublet, J=14 Hz); 5.05 (1H, doublet, J=5 Hz); 6.10 (1H, doublet of doublets, J=5 & 9 Hz); 6.42 (1H, singlet); 6.97 (1H, singlet).

1(c) Diphenylmethyl 7-[2-(2-aminothiazol-4-yl)-2-(syn-hydroxyimino)acetamido]-3-phenoxymethyl-3-cephem-4-carboxylate 1.16 g of diphenylmethyl 7-[2-(2-tritylaminothiazol-4-yl)-2-(syn-trityloxyimino)acetamido]-3-phenoxymethyl-3-cephem-4-carboxylate [prepared as described in step (b) above] was dissolved in a mixture of 5 ml of methanol and 5 ml of formic acid, and the solution was stirred at 45° C. for 1 hour. At the end of this time, the reaction mixture was concentrated by distillation under reduced pressure. The resulting residue was dissolved in ethyl acetate, and the solution was washed with a 5% w/v aqueous solution of sodium bicarbonate and with a saturated aqueous solution of sodium chloride, in that order, after which it was dried over anhydrous sodium sulfate. The solvent was then distilled off under reduced pressure, and the resulting residue was purified by column chromatography through silica gel, to afford 367 mg of the title compound as a powder.
Nuclear Magnetic Resonance Spectrum (hexadeuterated dimethyl sulfoxide) δ ppm: 4.74 (2H, singlet); 5.24 (1H, doublet, J=5 Hz); 5.91 (1H, doublet of doublets, J=5 & 8 Hz); 6.67 (1H, singlet); 6.95 (1H, singlet); 9.51 (1H, doublet, J=8 Hz); 11.31 (1H, broad singlet).

1(d) 7-[2-(2-Aminothiazol-4-yl)-2-(syn-hydroxyimino)acetamido]-3-phenoxymethyl-3-cephem-4-carboxylic acid trifluoroacetate 1.5 ml of trifluoroacetic acid was added dropwise to a solution of 350 mg of diphenylmethyl 7-[2-(2-aminothiazol-4-yl)-2-(syn-hydroxyimino)acetamido]-3-phenoxymethyl-3-cephem-4-carboxylate [prepared as described in step (c) above] dissolved in a mixture of 0.5 ml of methylene chloride and 1 ml of anisole, whilst ice-cooling, and then the mixture was stirred for 1 hour. At the end of this time, diisopropyl ether was added to the reaction mixture and the precipitate which deposited was collected by filtration to afford 213 mg of the title compound.
Nuclear Magnetic Resonance Spectrum (hexadeuterated dimethyl sulfoxide) δ ppm: 4.85 (2H, singlet); 5.19 (1H, doublet, J=5 Hz); 5.80 (1H, doublet of doublets, J=5 & 8 Hz); 6.74 (1H, singlet); 9.57 (1H, doublet, J=8 Hz); 11.67 (1H, broad singlet).

EXAMPLE 2

7-[2-(2-Aminothiazol-4-yl)-2-(syn-hydroxyimino)acetamido]-3-(2-fluorophenoxy)methyl-3-cephem-4-carboxylic acid trifluoroacetate 2(a) Diphenylmethyl 3-(2-fluorophenoxy)methyl-7-phenoxyacetamido-3-cephem-4-carboxylate The procedure described in Example 1(a) was repeated, but using 2.00 g of diphenylmethyl 3-hydroxymethyl-7-phenoxyacetamido-3-cephem-4-carboxylate and o-fluorophenol, to afford 510 mg of the title compound as a powder.
Nuclear Magnetic Resonance Spectrum (CDCl$_3$) δ ppm: 4.57 (2H, singlet); 4.88 (1H, doublet, J=14 Hz); 5.04 (1H, doublet, J=5 Hz); 5.06 (1H, doublet, J=14 Hz); 5.97 (1H, doublet of doublets, J=5 & 8 Hz); 6.7–7.5 (21H, multiplet).

2(b) Diphenylmethyl 3-(2-fluorophenoxymethyl)-7-[2-(2-tritylaminothiazol-4-yl)-2-(syn-trityloxyimino)acetamido]-3-cephem-4-carboxylate The procedure described in Example 1(b) was repeated, but using 700 mg of diphenylmethyl 3-(2-fluorophenoxy)methyl-7-phenoxyacetamido-3-cephem-4carboxylate [prepared as described in step (a) above], to afford 903 mg of the title compound as a powder.
Nuclear Magnetic Resonance Spectrum (CDCl$_3$) δ ppm: 3.45 (1H, doublet, J=18 Hz); 3.61 (1H, doublet, J=18 Hz); 4.86 (1H, doublet, J=14 Hz); 5.06 (1H, doublet, J=5 Hz); 5.07 (1H, doublet, J=14 Hz); 6.12 (1H, doublet of doublets, J=5 & 8 Hz); 6.43 (1H, singlet); 6.96 (1H, singlet).

2(c) Diphenylmethyl 7-[2-(2-aminothiazol-4-yl)-2-(syn-hydroxyimino)acetamido]-3-(2-fluorophenoxy)methyl-3-cephem-4-carboxylate The procedure described in Example 1(c) was repeated, but using 900 mg of diphenylmethyl 3-(2-fluorophenoxy)methyl-7-[2-(2-tritylaminothiazol-4-yl)-2-(syn-trityloxyimino)acetamido]-3-cephem-4-carboxylate [prepared as described in step (b) above], to afford 351 mg of the title compound as a powder.

Nuclear Magnetic Resonance Spectrum (hexadeuterated dimethyl sulfoxide) δ ppm: 4.81 (2H, singlet); 5.26 (1H, doublet, J=5 Hz); 5.92 (1H, doublet of doublets, J=5& 8 Hz); 6.67 (1H, singlet); 6.94 (1H, singlet); 9.52 (1H, doublet, J=8 Hz); 11.31 (1H, broad singlet).

2(d) 7-[2-(2-Aminothiazol-4-yl)-2-(syn-hydroxyimino)acetamido]-3-(2-fluorophenoxy)methyl-3-cephem-4-carboxylic acid trifluoroacetate The procedure described in Example 1(d) was repeated, but using 345 mg of diphenylmethyl 7-[2-(2-aminothiazol-4-yl)-2-(syn-hydroxyimino)acetamido]-3-(2-fluorophenoxy)methyl-3-cephem-4-carboxylate [prepared as described in step (c) above], to afford 193 mg of the title compound as a powder.

Nuclear Magnetic Resonance Spectrum (hexadeuterated dimethyl sulfoxide) δ ppm: 4.93 (2H, singlet); 5.21 (1H, doublet, J=5 Hz); 5.82 (1H, doublet of doublets, J=5 & 8 Hz); 6.74 (1H, singlet); 9.58 (1H, doublet, J=8 Hz); 11.67 (1H, broad singlet).

EXAMPLE 3

7-[2-(2-Aminothiazol-4-yl)-2-(syn-hydroxyimino)acetamido]-3-(3-fluorophenoxy)methyl-3-cephem-4-carboxylic acid trifluoroacetate 3(a) Diphenylmethyl 3-(3-fluorophenoxy)methyl-7-phenoxyacetamido-3-cephem-4-carboxylate The procedure described in Example 1(a) was repeated, but using 2.00 g of diphenylmethyl 3-hydroxymethyl-7-phenoxyacetamido-3-cephem-4-carboxylate and m-fluorophenol, to afford 357 mg of the title compound as a powder.

Nuclear Magnetic Resonance Spectrum (CDCl₃) δ ppm: 4.58 (2H, singlet); 4.79 (1H, doublet, J=14 Hz); 4.92 (1H, doublet, J=14 Hz); 5.05 (1H, doublet, J=5 Hz); 5.97 (1H, doublet of doublets, J=5 & 9 Hz); 6.6–7.5 (21H, multiplet).

3(b) Diphenylmethyl 3-(3-fluorophenoxy)methyl-7-[2-(2-tritylaminothiazol-4-yl)-2-(syn-trityloxyimino)acetamido]-3-cephem-4-carboxylate The procedure described in Example 1(b) was repeated, but using 480 mg of diphenylmethyl 3-(3-fluorophenoxy)methyl-7-phenoxyacetamido-3-cephem-4-carboxylate [prepared as described in step (a) above], to afford 620 mg of the title compound as a powder.

Nuclear Magnetic Resonance Spectrum (CDCl₃) δ ppm: 3.38 (1H, doublet, J=19 Hz); 3.54 (1H, doublet, J=19 Hz); 4.77 (1H, doublet, J=14 Hz); 4.94 (1H, doublet, J=14 Hz); 5.07 (1H, doublet, J=5 Hz); 6.11 (1H, doublet of doublets, J=5 & 8 Hz); 6.43 (1H, singlet); 6.97 (1H, singlet).

3(c) Diphenylmethyl 7-[2-(2-aminothiazol-4-yl)-2-(syn-hydroxyimino)acetamido]-3-(3-fluorophenoxy)methyl-3-cephem-4-carboxylate The procedure described in Example 1 (c) was repeated, but using 610 mg of diphenylmethyl 3-(3-fluorophenoxy)methyl-7-[2-(2-tritylaminothiazol-4-yl)-2-(syn-trityloxyimino)acetamido]-3-cephem-4-carboxylate [prepared as described in step (b) above], to afford 170 mg of the title compound as a powder.

Nuclear Magnetic Resonance Spectrum (hexadeuterated dimethyl sulfoxide) δ ppm: 4.73 (2H, singlet); 5.24 (1H, doublet, J=5 Hz); 5.91 (1H, doublet of doublets, J=5 & 8 Hz); 6.67 (1H, singlet); 6.95 (1H, singlet); 9.51 (1H, doublet, J=8 Hz); 11.31 (1H, broad singlet).

3(d) 7-[2-(2-Aminothiazol-4-yl)-2-(syn-hydroxyimino)acetamido]-3-(3-fluorophenoxy)methyl-3-cephem-4-carboxylic acid trifluoroacetate The procedure described in Example 1(d) was repeated, but using 160 mg of diphenylmethyl 7-[2-(2-aminothiazol-4-yl)-2-(syn-hydroxyimino)acetamido]-3-(3-fluorophenoxy)methyl-3-cephem-4-carboxylate [prepared as described in step (c) above], to afford 105 mg of the title compound as a powder.

Nuclear Magnetic Resonance Spectrum (hexadeuterated dimethyl sulfoxide) δ ppm: 4.82 (1H, doublet, J=12 Hz); 4.89 (1H, doublet, J=12 Hz); 5.19 (1H, doublet, J=5 Hz); 5.81 (1H, doublet of doublets, J=5 & 8 Hz); 6.70 (1H, singlet); 9.52 (1H, doublet, J=8 Hz); 11.50 (1H, broad singlet).

EXAMPLE 4

7-[2-(2-Aminothiazol-4-yl)-2-(syn-hydroxyimino)acetamido]-3-(4-fluorophenoxy)methyl-3-cephem-4-carboxylic acid trifluoroacetate 4(a) Diphenylmethyl 3-(4-fluorophenoxy)methyl-7-phenoxyacetamido-3-cephem-4-carboxylate The procedure described in Example 1(a) was repeated, but using 2.00 g of diphenylmethyl 3-hydroxymethyl-7-phenoxyacetamido-3-cephem-4-carboxylate and p-fluorophenol, to afford 400 mg of the title compound as a powder.

Nuclear Magnetic Resonance Spectrum (CDCl₃) δ ppm: 4.57 (2H, singlet); 4.77 (1H, doublet, J=14 Hz); 4.91 (1H, doublet, J=14 Hz); 5.04 (1H, doublet, J=5 Hz); 5.81 (1H, doublet of doublets, J=5 & 9 Hz); 6.5–7.5 (21H, multiplet).

4(b) Diphenylmethyl 3-(4-fluorophenoxy)methyl-7-[2-(2-tritylaminothiazol-4-yl)-2-(syn-trityloxyimino)acetamido]-3-cephem-4-carboxylate The procedure described in Example 1(b) was repeated, but using 633 mg of diphenylmethyl 3-(4-fluorophenoxy)methyl-7-phenoxyacetamido-3-cephem-4-carboxylate [prepared as described in step (a) above], to afford 601 mg of the title compound as a powder.

Nuclear Magnetic Resonance Spectrum (CDCl₃) δ ppm: 3.38 (1H, doublet, J=18 Hz); 3.53 (1H, doublet, J=18 Hz); 4.76 (1H, doublet, J=14 Hz); 4.93 (1H, doublet, J=14 Hz); 5.06 (1H, doublet, J=5 Hz); 6.10 (1H, doublet of doublets, J=5 & 9 Hz); 6.43 (1H, singlet); 6.97 (1H, singlet).

4(c) Diphenylmethyl 7-[2-(2-aminothiazol-4-yl)-2-(syn-hydroxyimino)acetamido]-3-(4-fluorophenoxy)methyl-3-cephem-4-carboxylate The procedure described in Example 1(c) was repeated, but using 590 mg of diphenylmethyl 3-(4-fluorophenoxy)methyl-7-[2-(2-tritylaminothiazol-4-yl)-2-(syn-trityloxyimino)acetamido]-3-cephem-4-carboxylate [prepared as described in step (b) above], to afford 257 mg of the title compound as a powder.

Nuclear Magnetic Resonance Spectrum (hexadeuterated dimethyl sulfoxide) δ ppm: 4.70 (2H, singlet); 5.24 (1H, doublet, J=5 Hz); 5.91 (1H, doublet of doublets, J=5 & 8 Hz); 6.67 (1H, singlet); 6.95 (1H, singlet); 9.51 (1H, doublet, J=8 Hz); 11.32 (1H, broad singlet).

4(d) 7-[2-(2-Aminothiazol-4-yl)-2-syn-hydroxyimino)acetamido]-3-(4-fluorophenoxy)methyl-3-cephem-4-carboxylic acid trifluoroacetate The procedure described in Example 1(d) was repeated, but using 245 mg of diphenylmethyl 7-[2-(2-aminothiazol-4-yl)-2-(syn-hydroxyimino)acetamido]-3-(4-fluorophenoxy)methyl-3-cephem-4-carboxylate [prepared as described in step (c) above], to afford 168 mg of the title compound as a powder.

Nuclear Magnetic Resonance Spectrum (hexadeuterated dimethyl sulfoxide) δ ppm: 4.80 (1H, doublet, J=12 Hz); 4.85 (1H, doublet, J=12 Hz); 5.18 (1H, doublet, J=5 Hz); 5.81 (1H, doublet of doublets, J=5 & 8 Hz); 6.71 (1H, singlet); 9.53 (1H, doublet, J=8 Hz); 11.55 (1H, broad singlet).

EXAMPLE 5

7-[2-(2-Aminothiazol-4-yl)-2-(syn-hydroxyimino)acetamido]-3-(2,4-difluorophenoxy)methyl-3-cephem-4-carboxylic acid trifluoroacetate 5(a) Diphenylmethyl 3-(2,4-difluorophenoxymethyl)-7-phenoxyacetamido-3-cephem-4-carboxylate The procedure described in Example 1(a) was repeated, but using 2.00 g of diphenylmethyl 3-hydroxymethyl-7-phenoxyacetamido-3-cephem-4-carboxylate and 2,4-difluorophenol, to afford 500 mg of the title compound as a powder.

Nuclear Magnetic Resonance Spectrum (CDCl$_3$) δ ppm: 4.57 (2H, singlet); 4.84 (1H, doublet, J=14 Hz); 4.99 (1H, doublet, J=14 Hz); 5.04 (1H, doublet, J=5 Hz); 5.97 (1H, doublet of doublets, J=5 & 9 Hz); 6.6-7.5 (20H, multiplet).

5(b) Diphenylmethyl 3-(2,4-difluorophenoxy)methyl-7-[2-(2-tritylaminothiazol-4-yl)-2-(syn-trityloxyimino)acetamido]-3-cephem-4-carboxylate The procedure described in Example 1(b) was repeated, but using 1.00 g of diphenylmethyl 3-(2,4-difluorophenoxy)-7-phenoxyacetamidomethyl-3-cephem-4-carboxylate [prepared as described in step (a) above], to afford 1.33 g of the title compound as a powder.

Nuclear Magnetic Resonance Spectrum (CDCl$_3$) δ ppm: 3.44 (1H, doublet, J=19 Hz); 3.61 (1H, doublet, J=19 Hz); 4.82 (1H, doublet, J=14 Hz); 5.00 (1H, doublet, J=14 Hz); 5.07 (1H, doublet, J=5 Hz); 6.11 (1H, doublet of doublets, J=5 & 9 Hz); 6.43 (1H, singlet); 6.95 (1H, singlet).

5(c) Diphenylmethyl 7-[2-(2-aminothiazol-4-yl)-2-(syn-hydroxyimino)acetamido]-3-(2,4-difluorophenoxy)-methyl-3-cephem-4-carboxylate The procedure described in Example 1(c) was repeated, but using 1.30 g of diphenylmethyl 3-(2,4-difluorophenoxy)methyl-7-[2-(2-tritylaminothiazol-4-yl)-2-(syn-trityloxyimino)acetamido]-3-cephem-4-carboxylate [prepared as described in step (b) above], to afford 500 mg of the title compound as a powder.

Nuclear Magnetic Resonance Spectrum (hexadeuterated dimethyl sulfoxide) δ ppm: 4.78 (2H, singlet); 5.25 (1H, doublet, J=5 Hz); 5.92 (1H, doublet of doublets, J=5 & 8 Hz); 6.67 (1H, singlet); 6.93 (1H, singlet); 9.52 (1H, doublet, J=8 Hz); 11.31 (1H, broad singlet).

5(d) 7-[2-(2-Aminothiazol-4-yl)-2-(syn-hydroxyimino)acetamido]-3-(2,4-difluorophenoxy)methyl-3-cephem-4-carboxylic acid trifluoroacetate The procedure described in Example 1(d) was repeated, but using 490 mg of diphenylmethyl 7-[2-(2-aminothiazol-4-yl)-2-(syn-hydroxyimino)acetamido]-3-(2,4-difluorophenoxy)methyl-3-cephem-4-carboxylate [prepared as described in step (c) above], to afford 215 mg of the title compound as a powder.

Nuclear Magnetic Resonance Spectrum (hexadeuterated dimethyl sulfoxide) δ ppm: 4.90 (2H, singlet); 5.20 (1H, doublet, J=5 Hz); 5.82 (1H, doublet of doublets, J=5 & 8 Hz); 6.73 (1H, singlet); 9.57 (1H, doublet, J=8 Hz); 11.66 (1H, broad singlet).

EXAMPLE 6

7-[2-(2-Aminothiazol-4-yl)-2-(syn-hydroxyimino)acetamido]-3-(4-bromophenoxy)methyl-3-cephem-4-carboxylic acid trifluoroacetate 6(a) Diphenylmethyl 3-(4-bromophenoxy)methyl-7-phenoxyacetamido-3-cephem-4-carboxylate The procedure described in Example 1(a) was repeated, but using 2.00 g of diphenylmethyl 3-hydroxymethyl-7-phenoxyacetamido-3-cephem-4-carboxylate and p-bromophenol, to afford 420 mg of the title compound as a powder.

Nuclear Magnetic Resonance Spectrum (CDCl$_3$) δ ppm: 4.57 (2H, singlet); 4.77 (1H, doublet, J=14 Hz); 4.92 (1H, doublet, J=14 Hz); 5.03 (1H, doublet, J=5 Hz); 5.96 (1H, doublet of doublets, J=5 & 9 Hz); 6.61 (2H, doublet, J=9 Hz); 6.8-7.5 (21H, multiplet).

6(b) Diphenylmethyl 3-(4-bromophenoxy)methyl-7-[2-(2-tritylaminothiazol-4-yl)-2-(syn-trityloxyimino)acetamido]-3-cephem-4-carboxylate The procedure described in Example 1(b) was repeated, but using 890 mg of diphenylmethyl 3-(4-bromophenoxy)methyl-7-phenoxyacetamido-3-cephem-4-carboxylate prepared as described in step (a) above], to afford 940 mg of the title compound as a powder.

Nuclear Magnetic Resonance Spectrum (CDCl$_3$) δ ppm: 3.37 (1H, doublet, J=18 Hz); 3.53 (1H, doublet, J=18 Hz); 4.76 (1H, doublet, J=14 Hz); 4.94 (1H, doublet, J=14 Hz); 5.06 (1H, doublet, J=5 Hz); 6.11 (1H, doublet of doublets, J=5 & 9 Hz); 6.42 (1H, singlet); 6.62 (2H, doublet, J=9 Hz); 6.97 (1H, singlet).

6(c) Diphenylmethyl 7-[2-(2-aminothiazol-4-yl)-2-(syn-hydroxyimino)acetamido]-3-(4-bromophenoxy)methyl-3-cephem-4-carboxylate The procedure described in Example 1(c) was repeated, but using 910 mg of diphenylmethyl 3-(4-bromophenoxy)methyl-7-[2-(2-tritylaminothiazol-4-yl)-2-(syn-trityloxyimino)acetamido]-3-cephem-4-carboxylate [prepared as described in step (b) above], to afford 350 mg of the title compound as a powder.

Nuclear Magnetic Resonance Spectrum (hexadeuterated dimethyl sulfoxide) δ ppm: 4.72 (2H, singlet); 5.23 (1H, doublet, J=5 Hz); 5.91 (1H, doublet of doublets, J=5 & 8 Hz); 6.67 (1H, singlet); 6.75 (2H, doublet, J=9 Hz); 6.94 (1H, singlet); 9.50 (1H, doublet, J=8 Hz); 11.30 (1H, singlet).

6(d) 7-[2-(2-Aminothiazol-4-yl)-2-(syn-hydroxyimino)acetamido]-3-(4-bromophenoxy)methyl-3-cephem-4carboxylic acid trifluoroacetate The procedure described in Example 1(d) was repeated, but using 340 mg of diphenylmethyl 7-[2-(2-aminothiazol-4-yl)-2-(syn-hydroxyimino)acetamido]-3-(4-bromophenoxy)methyl-3-cephem-4-carboxylate [prepared as described in step (c) above], to afford 230 mg of the title compound as a powder.

Nuclear Magnetic Resonance Spectrum (hexadeuterated dimethyl sulfoxide) δ ppm: 4.82 (1H, doublet, J=13 Hz); 4.87 (1H, doublet, J=13 Hz); 5.19 (1H, doublet, J=5 Hz); 5.81 (1H, doublet of doublets, J=5 & 8 Hz); 6.76 (1H, singlet); 6.94 (2H, doublet, J=9 Hz); 7.46 (2H, doublet, J=9 Hz); 9.59 (1H, doublet, J=8 Hz); 11.81 (1H, broad singlet).

EXAMPLE 7

7-[2-(2-Aminothiazol-4-yl)-2-(syn-hydroxyimino)acetamido]-3-(4-cyanophenoxy)methyl-3-cephem-4-carboxylic acid trifluoroacetate 7(a) Diphenylmethyl 3-(4-cyanophenoxy)methyl-7-phenoxyacetamido-3-cephem-4-carboxylate The procedure described in Example 1(a) was repeated, but using 2.00 g of diphenylmethyl 3-hydroxymethyl-7-phenoxyacetamido-3-cephem-4-carboxylate and p-cyanophenol, to afford 270 mg of the title compound as a powder.

Nuclear Magnetic Resonance Spectrum (CDCl$_3$) δ ppm: 4.58 (2H, singlet); 4.85 (1H, doublet, J=13 Hz); 4.98 (1H, doublet, J=13 Hz); 5.05 (1H, doublet, J=5 Hz); 5.98 (1H, doublet of doublets, J=5 & 9 Hz); 6.7–7.7 (21H, multiplet).

7(b) Diphenylmethyl 3-(4-cyanophenoxy)methyl-7-[2-(2-tritylaminothiazol-4-yl)-2-(syn-trityloxyimino)acetamido]-3-cephem-4-carboxylate The procedure described in Example 1(b) was repeated, but using 503 mg of diphenylmethyl 3-(4-cyanophenoxy)methyl-7-phenoxyacetamido-3-cephem-4-carboxylate [prepared as described in step (a) above], to afford 524 mg of the title compound as a powder.

Nuclear Magnetic Resonance Spectrum (CDCl$_3$) δ ppm: 3.37 (1H, doublet, J=19 Hz); 3.54 (1H, doublet, J=19 Hz); 4.84 (1H, doublet, J=13 Hz); 5.00 (1H, doublet, J=13 Hz); 5.08 (1H, doublet, J=5 Hz); 6.12 (1H, doublet of doublets, J=5 & 9 Hz); 6.44 (1H, singlet); 6.79 (2H, doublet, J=9 Hz); 6.97 (1H, singlet); 7.51 (2H, doublet, J=9 Hz).

7(c) Diphenylmethyl 7-[2-(2-aminothiazol-4-yl)-2-(syn-hydroxyimino)acetamido]-3-(4-cyanophenoxy)methyl-3-cephem-4-carboxylate The procedure described in Example 1(c) was repeated, but using 518 mg of diphenylmethyl 3-(4-cyanophenoxy)methyl-7-[2-(2-tritylaminothiazol-4-yl)-2-(syn-trityloxyimino)acetamido]-3-cephem-4-carboxylate [prepared as described in step (b) above], to afford 226 mg of the title compound as a powder.

Nuclear Magnetic Resonance Spectrum (hexadeuterated dimethyl sulfoxide) δ ppm: 4.87 (1H, doublet, J=13 Hz); 5.01 (1H, doublet, J=13 Hz); 5.09 (1H, doublet, J=5 Hz); 5.97 (1H, doublet of doublets, J=5 & 8 Hz); 6.80 (2H, doublet, J=9 Hz); 6.98 (1H, singlet); 7.51 (2H, doublet, J=9 Hz); 11.30 (1H, broad singlet).

7(d) 7-[2-(2-Aminothiazol-4-yl)-2-(syn-hydroxyimino)acetamido]-3-(4-cyanophenoxy)methyl-3-cephem-4-carboxylic acid trifluoroacetate The procedure described in Example 1(d) was repeated, but using 220 mg of diphenylmethyl 7-[2-(2-aminothiazol-4-yl)-2-(syn-hydroxyimino)acetamido]-3-(4-cyanophenoxy)methyl-3-cephem-4-carboxylate [prepared as described in step (c) above], to afford 145 mg of the title compound as a powder.

Nuclear Magnetic Resonance Spectrum (hexadeuterated dimethyl sulfoxide) δ ppm: 4.90 (1H, doublet, J=12 Hz); 4.97 (1H, doublet, J=12 Hz); 5.20 (1H, doublet, J=5 Hz); 5.82 (1H, doublet of doublets, J=5 & 8 Hz); 6.72 (1H, singlet); 7.14 (2H, doublet, J=9 Hz); 7.78 (2H, doublet, J=9 Hz); 9.54 (1H, doublet, J=8 Hz); 11.57 (1H, broad singlet).

EXAMPLE 8

7-[2-(2-Aminothiazol-4-yl)-2-(syn-hydroxyimino)acetamido]3-(4-carboxyphenoxy)methyl-3-cephem-4-carboxylic acid trifluoroacetate 8(a) Diphenylmethyl 3-(4-diphenylmethoxycarbonylphenoxy)methyl-7-phenoxyacetamido-3-cephem-4-carboxylate The procedure described in Example 1(a) was repeated, but using 2.00 g of diphenylmethyl 3-hydroxymethyl-7-phenoxyacetamido-3-cephem-4-carboxylate and p-(diphenylmethoxycarbonyl)phenol, to afford 864 mg of the title compound as a powder.

Nuclear Magnetic Resonance Spectrum (CDCl$_3$) δ ppm: 4.57 (2H, singlet); 4.86 (1H, doublet, J=13 Hz); 5.02 (1H, doublet, J=13 Hz); 5.04 (1H, doublet, J=5 Hz); 5.97 (1H, doublet of doublets, J=5 & 9 Hz); 6.77 (2H, doublet, J=9 Hz); 8.02 (2H, doublet, J=9Hz).

8(b) Diphenylmethyl 3-(4-diphenylmethyloxycarbonylphenoxy)methyl-7-[2-(2-tritylaminothiazol-4-yl)-2-(syn-trityloxyimino)acetamido]-3-cephem-4-carboxylate The procedure described in Example 1(b) was repeated, but using 900 mg of diphenylmethyl 3-(4diphenylmethoxycarbonylphenoxy)methyl-7-phenoxyacetamido-3-cephem-4-carboxylate [prepared as described in step (a) above], to afford 1.11 g of the title compound as a powder.

Nuclear Magnetic Resonance Spectrum (CDCl$_3$) δ ppm: 3.37 (1H, doublet, J=19 Hz); 3,53 (1H, doublet, J=19 Hz); 4.84 (1H, doublet, J=14 Hz); 5.05 (1H, doublet, J=14 Hz); 5.06 (1H, doublet, J=5 Hz); 6.11 (1H, doublet of doublets, J=5 & 9 Hz); 6.42 (1H, singlet); 6.77 (2H, doublet, J=9 Hz); 6.98 (1H, singlet); 7.09 (1H, singlet); 8.02 (2H, doublet, J=9Hz).

8(c) Diphenylmethyl 7-[2-(2-aminothiazol-4-yl)-2-(syn-hydroxyimino)acetamido]-3-(4-diphenylmethyloxycarbonylphenoxy)methyl-3-cephem-4-carboxylate The procedure described in Example 1(c) was repeated, but using 1.10 g of diphenylmethyl 3-(4-diphenylmethyloxycarbonylphenoxy)methyl-7-[2-(2-tritylaminothiazol-4-yl)-2-(syn-trityloxyimino)acetamido]-3-cephem-4-carboxylate [prepared as described in step (b) above], to afford 430 mg of the title compound as a powder.

Nuclear Magnetic Resonance Spectrum (hexadeuterated dimethyl sulfoxide) δ ppm: 4.85 (2H, singlet); 5.24 (1H, doublet, J=5 Hz); 5.92 (1H, doublet of doublets, J=5 & 8 Hz); 6.67 (1H, singlet); 6.92 (2H, doublet, J=9 Hz); 6.95 (1H, singlet); 7.02 (1H, singlet); 7.99 (2H, doublet, J=9 Hz); 9.51 (1H, doublet, J=8 Hz); 11.31 (1H, singlet).

8(d) 7-[2-(2-Aminothiazol-4-yl)-2-(syn-hydroxyimino)acetamido]-3-(4-carboxyphenoxy)methyl-3-cephem-4-carboxylic acid trifluoroacetate The procedure described in Example 1(d) was repeated, but using 420 mg of diphenylmethyl 7-[2-(2-aminothiazol-4-yl)-2-(syn-hydroxyimino)acetamido]-3-(4-diphenylmethyloxycarbonylphenoxy)methyl-3-cephem-4-carboxylate [prepared as described in step (c) above], to afford 250 mg of the title compound as a powder.

Nuclear Magnetic Resonance Spectrum (hexadeuterated dimethyl sulfoxide) δ ppm: 4.92 (2H, singlet); 5.20 (1H, doublet, J=5 Hz); 5.82 (1H, doublet of doublets, J=5 & 8 Hz); 7.04 (2H, doublet, J=9 Hz);

7.89 (2H, doublet, J=9 Hz); 9.55 (1H, doublet, J=8 Hz); 11.63 (1H, broad singlet).

EXAMPLE 9

7-[2-(2-Aminothiazol-4-yl)-2-(syn-hydroxyimino)acetamido]-3-(4-carbamoylphenoxy)methyl-3-cephem-4-carboxylic acid trifluoroacetate 9(a) Diphenylmethyl 7-allyloxyformamido-3-(4-carbamoylphenoxy)methyl-3-cephem-4-carboxylate A solution of 0.3 ml of dimethyl azodicarboxylate in 20 ml of tetrahydrofuran was added dropwise over a period of 15 minutes to a solution of 1.00 g of diphenylmethyl 7-allyloxyformamido-3-hydroxymethyl-3-cephem-4-carboxylate, 660 mg of triphenylphosphine and 350 mg of p-hydroxybenzamido in 20 ml of tetrahydrofuran, whilst ice-cooling and stirring. After stirring the reaction mixture, whilst ice-cooling it, for a further 15 minutes, it was diluted with ethyl acetate. The mixture was then washed with a saturated aqueous solution of sodium chloride and dried over anhydrous sodium sulfate. The solvent was then distilled off under reduced pressure, and the resulting residue was purified by column chromatography through silica gel to afford 207 mg of the title compound as a powder.

Nuclear Magnetic Resonance Spectrum (CDCl$_3$) δ ppm: 4.62 (2H, doublet, J=5 Hz); 4.82 (1H, doublet, J=14 Hz); 5.00 (1H, doublet, J=5 Hz); 5.02 (1H, doublet, J=14 Hz); 5.70 (1H, doublet of doublets, J=5 & 9 Hz); 6.78 (2H, doublet, J=9 Hz); 6.97 (1H, singlet); 7.70 (2H, doublet, J=9 Hz).

9(b) Diphenylmethyl 3-(4-carbamoylphenoxy)methyl-7-[2-(2-tritylaminothiazol-4-yl)-2-(syn-trityloxyimino)acetamido]-3-cephem-4-carboxylate A solution of 200 mg of diphenylmethyl 7-allyloxyformamido-3-(4-carbamoylphenoxy)methyl-3-cephem-4-carboxylate [prepared as described in step (a) above], 40 mg of tetrakis(triphenylphosphine)palladium and 9 mg of triphenylphosphine in 10 ml of methylene chloride was stirred at 15° C. for 1 hour. At the end of this time, 0.2 ml of diethylaniline, 275 mg of 2-(syn-trityloxyimino)-2-(2-tritylaminothiazol-4-yl)acetic acid and 0.04 ml of phosphorus oxychloride were added, in that order, to the solution, whilst ice-cooling and stirring. After the reaction mixture had been stirred at the same temperature for a further 30 minutes, it was diluted with ethyl acetate and washed with 3.5% v/v aqueous hydrochloric acid, with a 5% w/v aqueous solution of sodium bicarbonate and with a saturated aqueous solution of sodium chloride, in that order. It was then dried over anhydrous sodium sulfate. The solvent was then distilled off under reduced pressure, and the resulting residue was purified by column chromatography through silica gel to afford 283 mg of the title compound as a powder.

Nuclear Magnetic Resonance Spectrum (hexadeuterated dimethyl sulfoxide) δ ppm: 4.81 (1H, doublet, J=16 Hz); 5.01 (1H, doublet, J=16 Hz); 5.28 (1H, doublet, J=4 Hz); 5.75 (1H, doublet of doublets, J=4 & 7 Hz); 6.65 (1H, singlet); 6.74 (2H, doublet, J=8 Hz); 6.99 (1H, singlet); 7.80 (2H, doublet, J=8 Hz); 9.90 (1H, doublet, J=7 Hz).

9(c) Diphenylmethyl 7-[2-(2-aminothiazol-4-yl)-2-(syn-hydroxyimino)acetamido]-3-(4-carbamoylphenoxy)methyl-3-cephem-4-carboxylate The procedure described in Example 1(c) was repeated, but using 270 mg of diphenylmethyl 3-(4-carbamoylphenoxy)methyl-7-[2-(2-tritylaminothiazol-4-yl)-2-(syn-trityloxyimino)acetamido]-3-cephem-4-carboxylate [prepared as described in step (b) above], to afford 120 mg of the title compound as a powder.

Nuclear Magnetic Resonance Spectrum (hexadeuterated dimethyl sulfoxide) δ ppm: 4.82 (1H, doublet, J=16 Hz); 5.02 (1H, doublet, J=16 Hz): 5.13 (1H, doublet, J=4 Hz); 5.70 (1H, doublet of doublets, J=4 & 7 Hz); 6.72 (2H, doublet, J=9 Hz); 6.85 (1H, singlet); 6.98 (1H, singlet); 7.85 (2H, doublet, J=9 Hz); 9.60 (1H, singlet); 11.30 (1H, broad singlet).

9(d) 7-[2-(2-Aminothiazol-4-yl)-2-(syn-hydroxyimino)acetamido]-3-(4-carbamoylphenoxy)methyl-3-cephem-4-carboxylic acid trifluoroacetate The procedure described in Example 1(d) was repeated, but using 110 mg of diphenylmethyl 7-[2-(2-aminothiazol-4-yl)- 2-(syn-hydroxyimino)acetamido]-3-(4-carbamoylphenoxy)methyl-3-cephem-4-carboxylate [prepared as described in step (c) above], to afford 83 mg of the title compound as a powder.

Nuclear Magnetic Resonance Spectrum (hexadeuterated dimethyl sulfoxide) δ ppm: 4.94 (1H, doublet, J=16 Hz); 5.00 (1H, doublet, J=16 Hz); 5.11 (1H, doublet, J=4 Hz); 5.78 (1H, doublet of doublets, J=4 & 7 Hz); 6.77 (2H, doublet, J=8 Hz); 6.85 (1H, singlet); 7.83 (2H, doublet, J=8 Hz); 9.59 (1H, doublet, J=7 Hz); 11.67 (1H, broad singlet).

EXAMPLE 10

7-[2-(2-Aminothiazol-4-yl)-2-(syn-hydroxyimino)acetamido]-3-(3,4-difluorophenoxy)methyl-3-cephem-4-carboxylic acid trifluoroacetate 10(a) Diphenylmethyl 3-(3,4-difluorophenoxy)methyl-7-phenoxyacetamido-3-cephem-4-carboxylate The procedure described in Example 1(a) was repeated, but using 2.00 g of diphenylmethyl 7-phenoxyacetamido-3-hydroxymethyl-3-cephem-4-carboxylate and 3,4-difluorophenol, to afford 326 mg of the title compound as a powder.

Nuclear Magnetic Resonance Spectrum (CDCl$_3$) δ ppm: 4.58 (2H, singlet); 4.75 (1H, doublet, J=13 Hz); 4.86 (1H, doublet, J=13 Hz); 5.05 (1H, doublet, J=5 Hz); 5.97 (1H, doublet of doublets, J=5 & 9 Hz); 6.4–7.5 (20H, multiplet).

10(b) Diphenylmethyl 3-(3,4-difluorophenoxy)methyl-7-[2-(2-tritylaminothiazol-4-yl)-2-(syn-trityloxyimino)-acetamido]-3-cephem-4-carboxylate The procedure described in Example 1(a) was repeated, but using 450 mg of diphenylmethyl3-(3,4-difluorophenoxy)methyl-7-phenoxyacetamido-3-cephem-4-carboxylate [prepared as described in step (a) above], to afford 464 mg of the title compound as a powder.

Nuclear Magnetic Resonance Spectrum (CDCl$_3$) δ ppm: 3.37 (1H, doublet, J=18 Hz); 3.54 (1H, doublet, J=18 Hz); 4.73 (1H, doublet, J=13 Hz); 4.89 (1H, doublet, J=13 Hz); 5.07 (1H, doublet, J=5 Hz); 6.11 (1H, doublet of doublets, J=5 & 9 Hz); 6.43 (1H, singlet); 6.97 (1H, singlet).

10(c) Diphenylmethyl 7-[2-(2-aminothiazol-4-yl)-2-(syn-hydroxyimino)acetamido]-3-(3,4-difluorophenoxy)methyl-3-cephem-4-carboxylate The procedure described in Example 1(c) was repeated, but using 456 mg of diphenylmethyl 3-(3,4-difluorophenoxy)methyl-7-[2-(2-tritylaminothiazol-4-yl)-2-(syn-trityloxyimino)acetamido]-3-cephem-4-carboxylate [prepared as described in step (b) above], to afford 172 mg of the title compound as a powder.

Nuclear Magnetic Resonance Spectrum (hexadeuterated dimethyl sulfoxide) δ ppm: 4.69 (2H, singlet); 5.24 (1H, doublet, J=5 Hz); 5.91 (1H, doublet of doublets, J=5 & 8 Hz); 6.84 (1H, singlet); 6.95 (1H, singlet); 9.52 (1H, doublet, J=8 Hz); 11.31 (1H, broad singlet).

10(d) 7-[2-(2-Aminothiazol-4-yl)-2-(syn-hydroxyimino)acetamido]-3-(3,4-difluorophenoxy)methyl-3-cephem-4-carboxylic acid trifluoroacetate The procedure described in Example 1(d) was repeated, but using 155 mg of diphenylmethyl 7-[2-(2-aminothiazol-4-yl)-2-(syn-hydroxyimino)acetamido]-3-(3,4-difluorophenoxy)methyl-3-cephem-4-carboxylate [prepared as described in step (c) above], to afford 63 mg of the title compound as a powder.

Nuclear Magnetic Resonance Spectrum (hexadeuterated dimethyl sulfoxide) δ ppm: 4.79 (1H, doublet, J=12 Hz); 4.87 (1H, doublet, J=12 Hz); 5.19 (1H, doublet, J=5 Hz); 5.81 (1H, doublet of doublets, J=5 & 8 Hz); 6.72 (1H, singlet); 9.54 (1H, doublet, J=8 Hz); 11.57 (1H, broad singlet).

EXAMPLE 11

7-[2-(2-Aminothiazol-4-yl)-2-(syn-methoxyimino)acetamido]-3-(3-fluorophenoxy)methyl-3-cephem-4-carboxylic acid trifluoroacetate 11(a) Diphenylmethyl 3-(3-fluorophenoxy)methyl-7-[2-(2-tritylaminothiazol-4-yl)-2-(syn-methoxyimino)acetamido]-3-cephem-4-carboxylate Following a procedure similar to that described in Example 1(b), 500 mg of diphenylmethyl 3-(3-fluorophenoxy(methyl- 7-phenoxyacetamido-3-cephem-4-carboxylate [prepared as described in Example 3(a)] was converted to its hydrochloride, which was then reacted with 411 mg of 2-(syn-methoxyimino)-2-(2-tritylaminothiazol-4-yl)acetic acid, to give 475 mg of the title compound as a powder.

Nuclear Magnetic Resonance Spectrum (CDCl3) δ ppm: 4.08 (3H, singlet); 4.79 (1H, doublet, J=13 Hz); 4.93 (1H, doublet, J=13 Hz); 5.07 (1H, doublet, J=5 Hz); 5.97 (1H, doublet of doublets, J=5 & 9 Hz); 6.75 (1H, singlet); 6.96 (1H, singlet).

11(b) Diphenylmethyl 7-[2-(2-aminothiazol-4-yl)-2-(syn-methoxyimino)acetamido]-3-(3-fluorophenoxy)methyl-3-cephem-4-carboxylate The procedure described in Example 1(c) was repeated, but using 463 mg of diphenylmethyl 3-(3-fluorophenoxy)methyl-7-[2-(2-tritylaminothiazol-4-yl)-2-(syn-methoxyimino)acetamido]-3-cephem-4-carboxylate prepared as described in step (a) above], to afford 246 mg of the title compound as a powder.

Nuclear Magnetic Resonance Spectrum (hexadeuterated dimethyl sulfoxide) δ ppm: 3.85 (3H, singlet); 4.73 (2H, singlet); 5.25 (1H, doublet, J=5 Hz); 5.90 (1H, doublet of doublets, J=5 & 8 Hz); 6.75 (1H, singlet); 6.95 (1H, singlet); 9.66 (1H, doublet, J=8 Hz).

11(c) 7-[2-(2-Aminothiazol-4-yl)-2-(syn-methoxyimino)acetamido]-3-(3-fluorophenoxy)methyl-3-cephem-4-carboxylic acid trifluoroacetate The procedure described in Example 1(d) was repeated, but using 240 mg of diphenylmethyl 7-[2-(2-aminothiazol-4-yl)-2-(syn-methoxyimino)acetamido]-3-(3-fluorophenoxy)methyl-3-cephem-4-carboxylate [prepared as described in step (b) above], to afford 190 mg of the title compound as a powder.

Nuclear Magnetic Resonance Spectrum (hexadeuterated dimethyl sulfoxide) δ ppm: 3.58 (1H, doublet, J=18 Hz); 3.70 (1H, doublet, J=18 Hz); 3.87 (3H, singlet); 4.82 (1H, doublet, J=12 Hz); 4.90 (1H, doublet, J=12 Hz); 5.20 (1H, doublet, J=5 Hz); 5.81 (1H, doublet of doublets, J=5 & 8 Hz); 6.80 (1H, singlet); 9.68 (1H, doublet, J=8 Hz).

EXAMPLE 12

7-[2-(2-Aminothiazol-4-yl)-2-(syn-hydroxyimino)acetamido]-3-(3-cyanophenoxy)methyl-3-cephem-4-carboxylic acid trifluoroacetate 12(a) Diphenylmethyl 3-(3-cyanophenoxy)methyl-7-phenoxyacetamido-3-cephem-4-carboxylate The procedure described in Example 1(a), was repeated, but using 2.00 g of diphenylmethyl 7-phenoxyacetamido-3-hydroxymethyl-3-cephem-4-carboxylate and m-cyanophenol, to afford 490 mg of the title compound as a powder.

Nuclear Magnetic Resonance Spectrum (CDCl3) δ ppm: 4.58 (2H, singlet); 4.80 (1H, doublet, J=13 Hz); 4.90 (3H, doublet, J=13 Hz); 5.06 (1H, doublet, J=5 Hz); 5.98 (1H, doublet of doublets, J=5 & 9 Hz); 6.8–7.6 (21H, multiplet).

12(b) Diphenylmethyl 3-(3-cyanophenoxy)methyl-7-[2-(2-tritylaminothiazol-4-yl)-2-(syn-trityloxyimino)acetamido]-3-cephem-4-carboxylate The procedure described in Example 1(b) was repeated, but using 571 mg of diphenylmethyl 3-(3-cyanophenoxy)methyl-7-phenoxyacetamido-3-cephem-4-carboxylate [prepared as described in step (a) above], to afford 514 mg of the title compound as a powder.

Nuclear Magnetic Resonance Spectrum (CDCl3) δ ppm: 3.34 (1H, doublet, J=19 Hz); 3.56 (1H, doublet, J=19 Hz); 4.79 (1H, doublet, J=13 Hz); 4.93 (1H, doublet, J=13 Hz); 5.09 (1H, doublet, J=5 Hz); 6.12 (1H, doublet of doublets, J=5 & 9 Hz); 6.44 (1H, singlet); 6.97 (1H, singlet).

12(c) Diphenylmethyl 7-[2-(2-aminothiazol-4-yl)-2-(syn-hydroxyimino)acetamido]-3-(3-cyanophenoxy)-methyl-3-cephem-4-carboxylate The procedure described in Example 1(c) was repeated, but using 502 mg of diphenylmethyl 3-(3-cyanophenoxy)methyl-7-[2-(2-tritylaminothiazol-4-yl)-2-(syn-trityloxyimino)acetamido]-3-cephem-4-carboxylate [prepared as described in step (b) above], to afford 170 mg of the title compound as a powder.

Nuclear Magnetic Resonance Spectrum (hexadeuterated dimethyl sulfoxide) δ ppm: 4.87 (1H, doublet, J=13 Hz); 5.01 (1H, doublet, J=13 Hz); 5.25 (1H, doublet, J=5 Hz); 5.92 (1H, doublet of doublets, J=5 & 8 Hz); 6.67 (1H, singlet); 6.95 (1H, singlet); 9.52 (1H, doublet, J=8 Hz); 11.31 (1H, broad singlet).

12(d) 7-[2-(2-Aminothiazol-4-yl)-2-(syn-hydroxyimino)acetamido]-3-(3-cyanophenoxy)methyl-3-cephem-4-carboxylic acid trifluoroacetate The procedure described in Example 1(d) was repeated, but using 163 mg of diphenylmethyl 7-[2-(2-aminothiazol-4-yl)-2-(syn-hydroxyimino)acetamido]-3-(3-cyanophenoxy)methyl-3-cephem-4-carboxylate [prepared as described in step (c) above], to afford 125 mg of the title compound as a powder.

Nuclear Magnetic Resonance Spectrum (hexadeuterated dimethyl sulfoxide) δ ppm: 4.85 (1H, doublet, J=12 Hz); 4.94 (1H, doublet, J=12 Hz); 5.20 (1H, doublet, J=5 Hz); 5.82 (1H, doublet of doublets, J=5 & 8 Hz); 6.72 (1H, singlet); 9,55 (1H, doublet, J=8 Hz); 11.57 (1H, broad singlet).

EXAMPLE 13

3-(4-Acetylphenoxy)methyl-7-[2-(2-aminothiazol-4-yl)-2-(syn-hydroxyimino)acetamido]-3-cephem-4-carboxylic acid trifluoroacetate 13(a) Diphenylmethyl 3-(4-acetylphenoxy)methyl-7-phenoxyacetamido-3-cephem-4-carboxylate The procedure described in Example 1(a) was repeated, but using 2.00 g of 7-phenoxyacetamido-3-hydroxymethyl-3-cephem-4-carboxylate and p-hydroxyacetophenone, to afford 482 mg of the title compound as a powder.
Nuclear Magnetic Resonance Spectrum (CDCl$_3$) δ ppm: 2.55 (3H, singlet); 4.57 (2H, singlet); 4.87 (1H, doublet, J=13 Hz); 5.02 (1H, doublet, J=13 Hz); 5.04 (1H, doublet, J=5 Hz); 5.97 (1H, doublet of doublets, J=5 & 9 Hz); 6.78 (2H, doublet, J=9 Hz); 6.9–7.5 (17H, multiplet); 7.89 (2H, doublet, J=9 Hz).

13(b) Diphenylmethyl 3-(4-acetylphenoxy)methyl-7-[2-(2-tritylaminothiazol-4-yl)-2-(syn-trityloxyimino)acetamido]-3-cephem-4-carboxylate The procedure described in Example 1(b) was repeated, but using 530 mg of diphenylmethyl 3-(4-acetylphenoxy)methyl-7-phenoxyacetamido-3-cephem-4-carboxylate [prepared as described in step (a) above], to afford 524 mg of the title compound as a powder.
Nuclear Magnetic Resonance Spectrum (CDCl$_3$) δ ppm: 2.55 (3H, singlet); 3.39 (1H, doublet, J=19 Hz); 3.55 (1H, doublet, J=19 Hz); 4.86 (1H, doublet, J=13 Hz); 5.05 (1H, doublet, J=13 Hz); 5.07 (1H, doublet, J=5 Hz); 6.12 (1H, doublet of doublets, J=5 & 9 Hz); 6.43 (1H, singlet); 6.79 (2H, doublet, J=9 Hz); 6.98 (1H, singlet); 7.86 (2H, doublet, J=9 Hz).

13(c) Diphenylmethyl 3-(4-acetylphenoxy)methyl-7-[2-(2-aminothiazol-4-yl)-2-(syn-hydroxyimino)acetamido]-3-cephem-4-carboxylate The procedure described in Example 1(c) was repeated, but using 510 mg of diphenylmethyl 3-(4-acetylphenoxy)methyl-7-[2-(2-tritylaminothiazol-4-yl)-2-(syn-trityloxyimino)acetamido]-3-cephem-4-carboxylate [prepared as described in step (b) above], to afford 216 mg of the title compound as a powder.
Nuclear Magnetic Resonance Spectrum (hexadeuterated dimethyl sulfoxide) δ ppm: 2.52 (3H, singlet); 4.90 (1H, doublet, J=12 Hz); 4.97 (1H, doublet, J=12 Hz); 5.24 (1H, doublet, J=5 Hz): 5.92 (1H, doublet of doublets, J=5 & 8 Hz); 6.71 (1H, singlet); 6.96 (1H, singlet); 7.87 (2H, doublet, J=9 Hz); 9.52 (1H, doublet, J=8 Hz); 11.31 (1H, broad singlet).

13(d) 3-(4-Acetylphenoxy)methyl-7-[2-(2-aminothiazol-4-yl)-2-(syn-hydroxyimino)acetamido]-3-cephem-4-carboxylic acid trifluoroacetate The procedure described in Example 1(d) was repeated, but using 208 mg of diphenylmethyl 3-(4-acetylphenoxy)methyl-7-[2-(2-aminothiazol-4-yl)-2-(syn-hydroxyimino)acetamido]-3-cephem-4-carboxylate [prepared as described in step (c) above], to afford 140 mg of the title compound as a powder.
Nuclear Magnetic Resonance Spectrum (hexadeuterated dimethyl sulfoxide) δ ppm: 2.52 (3H, singlet); 4.92 (1H, doublet, J=12 Hz); 4.97 (1H, doublet, J=12 Hz); 5.20 (1H, doublet, J=5 Hz); 5.82 (1H, doublet of doublets, J=5 & 8 Hz); 6.73 (1H, singlet); 7.06 (2H, doublet, J=9 Hz); 7.93 (2H, doublet, J=9 Hz); 9.55 (1H, doublet, J=8 Hz); 11.60 (1H, broad singlet).

EXAMPLE 14

7-[2-(2-Aminothiazol-4-yl)-2-(syn-hydroxyimino)acetamido]-3-(4-methoxyphenoxy)methyl-3-cephem-4-carboxylic acid trifluoroacetate The procedure described in Example 1, steps (a), (b), (c) and (d), was repeated, but using 1.00 g of diphenylmethyl 7-phenoxyacetamido-3-hydroxymethyl-3-cephem-4-carboxylate and 300 mg of p-methoxyphenol in the initial step, to afford 40 mg of the title compound as a powder.
Nuclear Magnetic Resonance Spectrum (hexadeuterated dimethyl sulfoxide) δ ppm: 3.69 (3H, singlet); 4.79 (2H, singlet); 5.18 (1H, doublet, J=5 Hz); 5.80 (1H, doublet of doublets, J=5 & 8 Hz); 6.72 (1H, singlet); 6.86 (4H, singlet); 9.54 (2H, doublet, J=8 Hz); 11.57 (1H, broad singlet).

EXAMPLE 15

7-[2-(2-Aminothiazol-4-yl)-2-(syn-methoxyimino)acetamido]-3-(4-bromophenoxy)methyl-3-cephem-4-carboxylic acid trifluoroacetate The procedure described in Example 11, steps (b), (c) and (d), was repeated, but using 628 mg of diphenylmethyl 3-(4-bromophenoxy)methyl-7-phenoxyacetamido-3-cephem-4-carboxylate [prepared as described in Example 6(a)], to afford 114 mg of the title compound as a powder.
Nuclear Magnetic Resonance Spectrum (hexadeuterated dimethyl sulfoxide) δ ppm: 3.88 (3H, singlet); 4.82 (1H, doublet, J=13 Hz); 4.87 (1H, doublet, J=13 Hz); 5.18 (1H, doublet, J=5 Hz); 5.82 (1H, doublet of doublets, J=5 & 8 Hz); 6.76 (1H, singlet); 6.94 (2H, doublet, J=9 Hz); 7.45 (2H, doublet, J=9 Hz); 9.62 (1H, doublet, J=8 Hz).

EXAMPLE 16

7-[2-(2-Aminothiazol-4-yl)-2-(syn-methoxyimino)acetamido]-3-(4-carboxyphenoxy)methyl-3-cephem-4-carboxylic acid trifluoroacetate The procedure described in Example 11, steps (b), (c) and (d), was repeated, but using 330 mg of diphenylmethyl 7-phenoxyacetamido-3-(4-diphenylmethoxycarbonylphenoxy)methyl-3-cephem-4-carboxylate [prepared as described in Example 8(a)], to afford 52 mg of the title compound as a powder.
Nuclear Magnetic Resonance Spectrum (hexadeuterated dimethyl sulfoxide) δ ppm: 3.87 (3H, singlet); 4.92 (2H, singlet); 5.20 (1H, doublet, J=5Hz); 5.81 (1H, doublet of doublets, J=5 & 8 Hz); 6.79 (1H, singlet); 7.04 (2H, doublet, J=9 Hz); 7.89 (2H, doublet, J=9 Hz); 9.66 (1H, doublet, J=8 Hz).

EXAMPLE 17

7-[2-(5-Amino-1,2,4-thiadiazol-3-yl)-2-(syn-hydroxyimino)acetamido]-3-(3-fluorophenoxy)methyl-3-cephem-4carboxylic acid trifluoroacetate 17(b) Diphenylmethyl 7-[2-(5-t-butoxycarbonylamino-1,2,4-thiadiazol-3-yl)-2-(syn-trityloxyimino)acetamido]-3-(3-fluorophenoxy)methyl-3-cephem-4-carboxylate Following a procedure similar to that described in Example 1(b), 460 mg of diphenylmethyl 3-(3-fluorophenoxy)methyl-7-phenoxyacetamido-3-cephem-4-carboxylate [prepared as described in Example 3(a)], was converted to its hydrochloride, which was then reacted with 330 mg of 2-(5-t-butoxycarbonylamino-1,2,4- thiadiazol-3-yl)-2-syn-trityloxyiminoacetic acid, to give 483 mg of the title compound as a powder.

Nuclear Magnetic Resonance Spectrum (CDCl$_3$) δ ppm: 3.44 (1H, doublet, J=19 Hz); 3.57 (1H, doublet, J=19 Hz); 4.78 (1H, doublet, J=13 Hz); 4.94 (1H, doublet, J=13 Hz); 5.07 (1H, doublet, J=5 Hz); 6.12 (1H, doublet of doublets, J=5 & 9 Hz); 6.46–6.71 (3H, multiplet); 6.98 (1H, singlet).

17(c) Diphenylmethyl 7-[2-(5-t-butoxycarbonylamino-1,2,4-thiadiazol-3-yl)-2-(syn-hydroxyimino)acetamido]-3-(3-fluorophenoxy)methyl-3-cephem-4-carboxylate The procedure described in Example 1(c) was repeated, but using 470 mg of diphenylmethyl 7-[2-(5-t-butoxycarbonylamino-1,2,4-thiadiazol-3-yl)-2-(syn-trityloxyimino)acetamido]-3-(3-fluorophenoxy)methyl-3-cephem-4-carboxylate [prepared as described in step (b) above], to afford 83 mg of the title compound as a powder.

Nuclear Magnetic Resonance Spectrum (CDCl$_3$) δ ppm: 3.5 (2H, multiplet); 4.84 (1H, doublet, J=13 Hz); 4.99 (1H, doublet, J=13 Hz); 5.11 (1H, doublet, J=5 Hz); 6.00 (1H, doublet of doublets, J=5 & 9 Hz); 6.48–6.71 (3H, multiplet); 6.98 (1H, singlet); 10.41 (1H, doublet, J=9 Hz).

17(d) 7-[2-(5-Amino-1,2,4-thiadiazol-3-yl)-2-(syn-hydroxyimino)acetamido]-3-(3-fluorophenoxy)methyl-3-cephem-4-carboxylic acid trifluoroacetate 0.6 ml of trifluoroacetic acid was added dropwise to a solution of 110 mg of diphenylmethyl 7-[2-(5-t-butoxycarbonylamino-1,2,4-thiadiazol-3-yl)-2-(syn-hydroxyimino)acetamido]-3-(3-fluorophenoxy)methyl-3-cephem-4-carboxylate [prepared as described in step (c) above] in anisole, and the mixture was stirred at room temperature for 1 hour. At the end of this time, diisopropyl ether was added to the reaction mixture to cause a precipitate to deposit. This was collected by filtration to afford 64 mg of the title compound.

Nuclear Magnetic Resonance Spectrum (hexadeuterated dimethyl sulfoxide) δ ppm: 4.82 (1H, doublet, J=12 Hz); 4.87 (1H, doublet, J=12 Hz); 5.16 (1H, doublet, J=5 Hz); 5.84 (1H, doublet of doublets, J=5 & 8 Hz); 6.75–6.88 (3H, multiplet); 7.27–7.36 (1H, multiplet); 8.04 (2H, singlet); 9.45 (1H, doublet, J=8 Hz).

EXAMPLE 18

Sodium 7-[2-(2-aminothiazol-4-yl)-2-(syn-hydroxyimino)acetamido]-3-(3-fluorophenoxy)methyl-3-cephem-4-carboxylate A solution of 90 mg of sodium 2-ethylhexanoate in 1 ml of methanol was added to a solution of 90 mg of 7-[2-(2-aminothiazol-4-yl)-2-(syn-hydroxyimino)acetamido]-3-(3-fluorophenoxy)methyl-3-cephem-4-carboxylic acid trifluoroacetate (prepared as described in Example 3) in methanol, and the mixture was stirred for 15 minutes. At the end of this time, diisopropyl ether was added to the reaction mixture to cause the deposition of a powder, which was collected by filtration to afford 82 mg of the title compound.

Nuclear Magnetic Resonance Spectrum (hexadeuterated dimethyl sulfoxide) δ ppm: 4.91 (1H, doublet, J=12 Hz); 4.98 (1H, doublet, J=12 Hz); 4.99 (1H, doublet, J=5 Hz); 5.62 (1H, doublet of doublets, J=5 & 8 Hz); 6.73 (1H, singlet); 9.55 (1H, doublet, J=8 Hz); 11.50 (1H, broad singlet).

EXAMPLE 19

Pivaloyloxymethyl 7-[2-(2-aminothiazol-4-yl)-2-(syn-hydroxyimino)acetamido]-3-(3-fluorophenoxy)methyl-3-cephem-4-carboxylate 0.04 ml of pivaloyloxymethyl iodide was added to solution of 75 mg of sodium 7-[2-(2-aminothiazol-4-yl)-2-(syn-hydroxyimino)acetamido]-3-(3-fluorophenoxy)-methyl-3-cephem-4-carboxylate (prepared as described in Example 18) in 2 ml of dimethylacetamide, whilst ice-cooling, and the mixture was stirred for 1 hour. At the end of this time, the reaction mixture was poured into water and extracted with ethyl acetate. The extract was washed with a saturated aqueous solution of sodium chloride and dried over anhydrous sodium sulfate. The solvent was distilled off under reduced pressure, and the resulting residue was purified by column chromatography through silica gel to afford 58 mg of the title compound as a powder.

Nuclear Magnetic Resonance Spectrum (hexadeuterated dimethyl sulfoxide) δ ppm: 4.81 (1H, doublet, J=12 Hz); 5.23 (1H, doublet, J=5 Hz); 5.81 (1H, doublet, J=6 Hz); 5.82 (1H, doublet of doublets, J=5 & 8 Hz); 5.90 (1H, doublet, J=6 Hz); 6.66 (1H, singlet); 9.49 (1H, doublet, J=8 Hz); 11.30 (1H, broad singlet).

EXAMPLE 20

7-[2-(2-Aminothiazol-4-yl)-2-(syn-hydroxyimino)acetamido]-3-(3-methoxyphenoxy)methyl-3-cephem-4-carboxylic acid trifluoroacetate The procedure described in Example 1 was repeated, but using 6.50 g of diphenylmethyl 7-phenoxyacetamido-3-hydroxymethyl-3-cephem-4-carboxylate and 2.0 ml of m-methoxyphenol, to give 242 mg of the title compound in the form of a powder.

Nuclear Magnetic Resonance Spectrum (hexadeuterated dimethyl sulfoxide) δ ppm: 3.72 (3H, singlet); 4.84 (2H, singlet); 5.16 (1H, doublet, J=5 Hz); 5.80 (1H, doublet of doublets, J=5 & 8 Hz); 6.65 (1H, singlet); 9.46 (1H, doublet, J=8 Hz); 11.28 (1H, singlet).

EXAMPLE 21

7-[2-(2-Aminothiazol-4-yl)-2-(syn-hydroxyimino)acetamido]-3-(4-hydroxyphenoxy)methyl-3-cephem-4-carboxylic acid trifluoroacetate The procedure described in Example 1 was repeated, but using 5.00 g of diphenylmethyl 7-phenoxyacetamido-3-hydroxymethyl-3-cephem-4-carboxylate and 2.50 g of p-[(2-methoxy)ethoxymethoxy]phenol, to give 56 mg of the title compound in the form of a powder.

Nuclear Magnetic Resonance Spectrum (hexadeuterated dimethyl sulfoxide) δ ppm: 4.69 (1H, doublet, J=12 Hz); 4.75 (1H, doublet, J=12 Hz); 5.51 (1H, doublet, J=4 Hz); 6 04 (1H, doublet of doublets, J=4 & 8 Hz); 6.67 (2H, doublet, J=9 Hz); 6.76 (1H, singlet); 6.78 (2H, doublet, J=9 Hz); 9.43 (1H, doublet, J=8 Hz); 11.64 (1H, singlet).

EXAMPLE 22

3-(4-Acetyl-3-hydroxyphenoxy)methyl-7-[2-(2-aminothiazol-4-yl)-2-(syn-hydroxyimino)acetamido]-3-cephem-4-carboxylic acid trifluoroacetate The procedure described in Example 1 was repeated, but using 6.00 g of diphenylmethyl 7-phenoxyacetamido-3-hydroxymethyl-3-cephem-4-carboxylate and 3.50 g of 4-acetyl-3-[2-(methoxy)ethoxymethoxy]-phenol, to give 25 mg of the title compound in the form of a powder.

Nuclear Magnetic Resonance Spectrum (hexadeuterated dimethyl sulfoxide) δ ppm: 2.57 (3H, singlet); 4.89 (1H, doublet, J=12 Hz); 4.96 (1H, doublet, J=12 Hz); 5.19 (1H, doublet, J=5 Hz); 5.82 (1H, doublet of doublets, J=5 & 8 Hz); 6.71 (1H, singlet); 9.52 (1H, doublet, J=8 Hz); 11.51 (1H, singlet); 12.58 (1H, singlet).

EXAMPLE 23

1-(Isopropoxycarbonyloxy)ethyl 7-[2-(2-aminothiazol-4-yl)-2-(syn-hydroxyimino)acetamido]-3-(3-fluorophenoxy)methyl-3-cephem-4-carboxylate (a mixture of diastereoisomers)

200 mg of sodium 7-[2-(2-aminothiazol-4-yl)-2-(syn-hydroxyimino)acetamido]-3-(3-fluorophenoxy)methyl-3-cephem-4-carboxylate (prepared as described in Example 18) and 150 mg of 1-(isopropoxycarbonyloxy)ethyl iodide were reacted and worked up by a similar method to that described in Example 19, to give 89 mg of the title compound in the form of a powder.

Nuclear Magnetic Resonance Spectrum (hexadeuterated dimethyl sulfoxide) δ ppm: 1.20 & 1.22 (6H in total, doublet×2, J=6 Hz); 1.46 & 1.48 (3H in total, doublet×2, J=6 Hz); 4.6–4.9 (1H, multiplet); 4.81 (2H, singlet); 5.21 & 5.23 (1H in total, doublet×2, J=5 Hz); 5.8–6.0 (1H, multiplet); 6.65 (1H, singlet); 9.47 (1H, doublet, J=8 Hz); 11.29 (1H, singlet).

EXAMPLE 24

1-Acetoxyethyl 7-[2-(2-aminothiazol-4-yl)-2-(syn-hydroxyimino)acetamido]-3-(3-fluorophenoxy)methyl-3-cephem-4-carboxylate (a mixture of diastereoisomers)

200 mg of sodium 7-[2-(2-aminothiazol-4-yl)-2-(syn-hydroxyimino)acetamido]-3-(3-fluorophenoxy)methyl-3-cephem-4-carboxylate (prepared as described in Example 18) and 130 mg of 1-acetoxyethyl iodide were reacted and worked up by a similar method to that described in Example 19, to give 102 mg of the title compound in the form of a powder.

Nuclear Magnetic Resonance Spectrum (hexadeuterated dimethyl sulfoxide) δ ppm: 1.44 & 1.46 (3H in total, doublet×2, J=6 Hz); 1.92 & 2.05 (3H in total, singlet×2); 4.79 (2H, singlet); 5.20 & 5.22 (1H in total, doublet×2, J=5 Hz); 5.8–6.0 (1H, multiplet); 6.80 (1H, singlet); 9.47 (1H, doublet, J=8 Hz); 11.29 (1H, singlet).

EXAMPLE 25

1-(Ethoxycarbonyloxy)ethyl 7-[2-(2-aminothiazol-4-yl)-2-(syn-hydroxyimino)acetamido]-3-(3-fluorophenoxy)methyl-3-cephem-4-carboxylate (a mixture of diastereoisomers)

200 mg of sodium 7-[2-(2-aminothiazol-4-yl)-2-(syn-hydroxyimino)acetamido]-3-(3-fluorophenoxy)methyl-3-cephem-4-carboxylate (prepared as described in Example 18) and 150 mg of 1-(ethoxycarbonyloxy)ethyl iodide were reacted and worked up by a similar method to that described in Example 19, to give 190 mg of the title compound in the form of a powder.

Nuclear Magnetic Resonance Spectrum (hexadeuterated dimethyl sulfoxide) δ ppm: 1.19 & 1.20 (3H in total, triplet×2, J=7 Hz); 1.47 & 1.49 (3H in total, doublet×2, J=5 Hz); 4.1–4.4 (2H, multiplet); 4.79 & 4.82 (2H in total, singlet×2); 5.21 & 5.23 (1H in total, doublet×2, J=5 Hz); 5.8–6.0 (1H, multiplet); 6.65 & 6.66 (1H in total, singlet×2); 9.48 (1H, doublet, J=8 Hz); 11.30 (1H, singlet).

EXAMPLE 26

Methyl 7-[2-(2-aminothiazol-4-yl)-2-(syn-hydroxyimino)acetamido]-3-(3-fluorophenoxy)methyl-3-cephem-4-carboxylate 150 mg of sodium 7-[2-(2-aminothiazol-4-yl)-2-(syn-hydroxyimino)acetamido]-3-(3-fluorophenoxy)methyl-3-cephem-4-carboxylate (prepared as described in Example 18) and 0.1 ml of methyl iodide were reacted and worked up by a similar method to that described in Example 19, to give 64 mg of the title compound in the form of a powder.

Nuclear Magnetic Resonance Spectrum (hexadeuterated dimethyl sulfoxide) δ ppm: 3.78 (3H, singlet); 4.78 (1H, doublet, J=12 Hz); 4.85 (1H, doublet, J=12 Hz); 5.21 (1H, doublet, J=4 Hz); 5.84 (1H, doublet of doublets, J=4 & 8 Hz); 6.65 (1H, singlet); 9.48 (1H, doublet, J=8 Hz); 11.29 (1H, singlet).

EXAMPLE 27

Pivaloyloxymethyl 7-[2-(2-aminothiazol-4-yl)-2-(syn-hydroxyimino)acetamido]-3-(3-cyanophenoxy)methyl-3-cephem-4-carboxylate 200 mg of 7-[2-(2-aminothiazol-4-yl)-2-(syn-hydroxyimino)acetamido]-3-(3-cyanophenoxy)methyl-3-cephem-4-carboxylic acid trifluoroacetate (prepared as described in Example 12) and 0.1 ml of pivaloyloxymethyl iodide were reacted and worked up by similar methods to those described in Examples 18 and 19, to give 160 mg of the title compound in the form of a powder.

Nuclear Magnetic Resonance Spectrum (hexadeuterated dimethyl sulfoxide) δ ppm: 4.83 (1H, doublet, J=12 Hz); 4.89 (1H, doublet, J=12 Hz); 5.25 (1H, doublet, J=5 Hz); 5.81 (1H, doublet, J=6 Hz); 5.85 (1H, doublet of doublets, J=5 & 8 Hz); 5.90 (1H, doublet, J=6 Hz); 6.74 (1H, singlet); 9.58 (1H, doublet, J=8 Hz); 11.65 (1H, singlet).

EXAMPLE 28

1-(Ethoxycarbonyloxy)ethyl 7-[2-(2-aminothiazol-4-yl)-2-(syn-hydroxyimino)acetamido]-3-(3cyanophenoxy)methyl-3-cephem-4-carboxylate (a mixture of diastereoisomers)

200 mg of 7-[2-(2-aminothiazol-4-yl)-2-(syn-hydroxyimino)acetamido] -3-(3-cyanophenoxy)methyl-3-cephem-4-carboxylic acid trifluoroacetate (prepared as described in Example 12) and 150 mg of 1-(ethoxycarbonyloxy)ethyl iodide were reacted and worked up by similar methods to those described in Examples 18 and 19, to give 150 mg of the title compound in the form of a powder.

Nuclear Magnetic Resonance Spectrum (hexadeuterated dimethyl sulfoxide) δ ppm: 1.19 & 1.20 (3H in total, triplet×2, J=7 Hz); 1.47 & 1.49 (3H in total, doublet×2, J=6 Hz); 4.0–4.4 (2H, multiplet); 4.83 & 4.86 (2H in total, singlet×2); 5.22 & 5.24 (1H in total, doublet×2, J=5 Hz); 5.8–6.0 (1H, multiplet); 6.65 & 6.66 (1H in total, singlet×2); 9.48 (1H, doublet, J=8 Hz); 11.30 (1H, singlet).

EXAMPLE 29

1-(Isopropoxycarbonyloxy)ethyl
7-[2-(2-aminothiazol-4-yl)-2-(syn-hydroxyimino)acetamido]-3-(3-cyanophenoxy)methyl-3-cephem-4-carboxylate (a mixture of diastereoisomers)

200 mg of 7-[2-(2-aminothiazol-4-yl)-2-(syn-hydroxyimino)acetamido]-3-(3-cyanophenoxy)methyl-3-cephem-4-carboxylic acid trifluoroacetate (prepared as described in Example 12) and 150 mg of 1-(isopropoxycarbonyloxy)ethyl iodide were reacted and worked up by similar methods to those described in Examples 18 and 19, to give 150 mg of the title compound in the form of a powder.

Nuclear Magnetic Resonance Spectrum (hexadeuterated dimethyl sulfoxide) δ ppm: 1.20 & 1.21 (6H in total, doublet×2, J=6 Hz); 1.46 & 1.48 (3H in total, doublet×2, J=6 Hz); 4.6–4.9 (1H, multiplet); 4.85 (2H, singlet); 5.22 & 5.24 (1H in total, doublet×2, J=5 Hz); 5.8–6.0 (1H, multiplet); 6.65 (1H, singlet); 9.48 (1H, doublet, J=8 Hz); 11.30 (1H, singlet).

EXAMPLE 30

1-Acetoxyethyl
7-[2-(2-aminothiazol-4-yl)-2-(syn-hydroxyimino)acetamido]-3-(3-cyanophenoxy)methyl-3-cephem-4-carboxylate (a mixture of diastereoisomers)

150 mg of 7-[2-(2-aminothiazol-4-yl)-2-(syn-hydroxyimino)acetamido]-3-(3-cyanophenoxy)methyl-3-cephem-4-carboxylic acid trifluoroacetate (prepared as described in Example 12) and 130 mg of 1-acetoxyethyl iodide were reacted and worked up by similar methods to those described in Examples 18 and 19, to give 120 mg of the title compound in the form of a powder.

Nuclear Magnetic Resonance Spectrum (hexadeuterated dimethyl sulfoxide) δ ppm: 1.43 & 1.46 (3H in total, doublet×2, J=6 Hz); 1.92 & 2.05 (3H in total, singlet×2); 4.87 (2H, singlet); 5.2–5.4 (1H, multiplet); 5.8–6.0 (1H, multiplet); 6.66 (1H, singlet); 9.48 (1H, doublet, J=8 Hz); 11.30 (1H, singlet).

EXAMPLE 31

(5-Methyl-2-oxo-1,3-dioxolen-4-yl)methyl
7-[2-(2-aminothiazol-4-yl)-2-(syn-hydroxyimino)acetamido]-3-(3-cyanophenoxy)methyl-3-cephem-4-carboxylate 100 mg of 7-[2-(2-aminothiazol-4-yl)-2-(syn-hydroxyimino)acetamido]-3-(3-cyanophenoxy)methyl-3-cephem-4-carboxylic acid trifluoroacetate (prepared as described in Example 12 ) and 55 mg of 4-bromomethyl-2-oxo-5-methyl-1,3-dioxolene were reacted and worked up by similar methods to those described in Examples 18 and 19, to give 55 mg of the title compound in the form of a powder.

Nuclear Magnetic Resonance Spectrum (hexadeuterated dimethyl sulfoxide) δ ppm: 2.12 (3H, singlet); 4.83 (2H, singlet); 5.09 (1H, doublet, J=14 Hz); 5.22 (1H, doublet, J=5 Hz); 5.23 (1H, doublet, J=14 Hz); 5.86 (1H, doublet of doublets, J=5 & 8 Hz); 6.66 (1H, singlet); 9.47 (1H, doublet, J=8 Hz); 11.29 (1H, singlet).

EXAMPLE 32

Pivaloyloxymethyl
7-[2-(2-aminothiazol-4-yl)2-(syn-ethoxycarbonyloxyimino)acetamido]-3-(3-fluorophenoxy)methyl-3-cephem-4-carboxylate trifluoroacetate 32(a) Pivaloyloxymethyl 7-[2-(2-tritylaminothiazol-4-yl)-2-(syn-hydroxyimino)acetamido]-3-(3-fluorophenoxy)methyl-3-cephem-4-carboxylate 1.30 g of pivaloyloxymethyl 7-amino-3-(3-fluorophenoxy)methyl-3-cephem-4-carboxylate hydrochloride [prepared as described hereafter in Example 45(a)] was dissolved in 15 ml of methylene chloride. 1.3 ml of diethylaniline and 1.5 molar equivalents of bromoacetyl bromide were then added to the resulting solution whilst ice-cooling, after which the mixture was stirred for 15 minutes. At the end of this time, the reaction mixture was diluted with ethyl acetate and washed, in turn, with a dilute hydrochloric acid and with a saturated aqueous solution of sodium chloride; it was then dried over anhydrous sodium sulfate. The solvent was removed by evaporation under reduced pressure to leave 1.11 g of a residue, which was dissolved in 8 ml of acetic acid. 150 mg of sodium nitrite were added to the solution, and then the mixture was stirred at room temperature for 30 minutes. At the end of this time, the solvent was removed by evaporation under reduced pressure and the residue was dissolved in ethyl acetate. The resulting solution was adjusted to neutrality by the addition of an aqueous solution of sodium bicarbonate, after which it was washed with water and dried over anhydrous sodium sulfate. The solvent was removed by evaporation under reduced pressure to leave 1.10 g of residue, which was dissolved in 10 ml of dimethylacetamide. 230 mg of sodium bicarbonate and 690 mg of tritylthiourea were added to this solution, and then the mixture was stirred at room temperature for 2 hours. At the end of this time, the reaction mixture was diluted with ethyl acetate, washed with water and dried over anhydrous sodium sulfate. The solvent was then removed by evaporation under reduced pressure to give 1.16 g of the title compound in the form of a powder.

Nuclear Magnetic Resonance Spectrum (hexadeuterated dimethyl sulfoxide) δ ppm: 1.12 (9H, singlet); 4.85 (2H, singlet); 5.24 (1H, doublet, J=5 Hz); 5.82 (1H, doublet, J=6 Hz); 5.89 (1H, doublet of doublets, J=5 & 8 Hz); 5.90 (1H, doublet, J=6 Hz); 6.80 (1H, singlet); 9.48 (1H, doublet, J=8 Hz); 11.34 (1H, singlet).

32(b) Pivaloyloxymethyl 7-[2-(2-tritylaminothiazol-4-yl)-2-(syn-ethoxycarbonyloxyimino)acetamido]-3-(3-fluorophenoxy)methyl-3-cephem-4-carboxylate 0.05 ml of ethyl chloroformate was added dropwise, whilst ice-cooling, to a solution of 300 mg of pivaloyloxymethyl 7-[2-(2-tritylaminothiazol-4-yl)-2-(syn-hydroxyimino)acetamido]-3-(3-fluorophenoxy)methyl-3-cephem-4-carboxylate [prepared as described in step (a) above] and 0.09 ml of diethylaniline in 5 ml of methylene chloride, and then the mixture was stirred for 30 minutes. At the end of this time, the reaction mixture was diluted with ethyl acetate, washed, in turn, with a dilute hydrochloric acid, with water, with an aqueous solution of sodium bicarbonate and with a saturated aqueous solution of sodium chloride, and then dried over anhydrous sodium sulfate. The solvent was then removed by evaporation under reduced pressure and the resulting residue was mixed with diisopropyl ether to give 224 mg of the title compound in the form of a powder.

Nuclear Magnetic Resonance Spectrum (CDCl₃) δ ppm: 1.20 (9H, singlet); 1.35 (3H, triplet, J=7 Hz); 4.87 (1H, doublet, J=14 Hz); 5.04 (1H, doublet, J=14 Hz); 5.09 (1H, doublet, J=5 Hz); 5.88 (1H, doublet, J=6 Hz); 5.92 (1H, doublet, J=6 Hz); 5.8–6.0 (1H, multiplet); 6.96 (1H, singlet).

32(c) Pivaloyloxymethyl 7-[2-(2-aminothiazol-4-yl)-2-(syn-ethoxycarbonyloxyimino)acetamido]-3-(3-fluorophenoxy)methyl-3-cephem-4-carboxylate trifluoroacetate 210 mg of pivaloyloxymethyl 7-[2-(2-tritylaminothiazol-4-yl)-2-(syn-ethoxycarbonyloxyimino)acetamido]-3-(3-fluorophenoxy)methyl-3-cephem-4-carboxylate [prepared as described in step (b) above] were dissolved in a mixture of 0.5 ml of anisole, 2 ml of trifluoroacetic acid and 1 ml of methylene chloride, and then the solution was stirred at room temperature for 4 hours. At the end of this time, diisopropyl ether was added to the reaction mixture to give a precipitate, which was collected by filtration to afford 146 mg of the title compound in the form of a powder.

Nuclear Magnetic Resonance Spectrum (hexadeuterated dimethyl sulfoxide) δ ppm: 1.12 (9H, singlet); 1.26 (3H, triplet, J=7 Hz); 3.64 (1H, doublet, J=18 Hz); 3.76 (1H, doublet, J=18 Hz); 4.24 (2H, triplet, J=7 Hz); 4.81 (1H, doublet, J=14 Hz); 4.86 (1H, doublet, J=14 Hz); 5.26 (1H, doublet, J=5 Hz); 5.82 (1H, doublet, J=6 Hz); 5.89 (1H, doublet of doublets, J=4 & 8 Hz); 5.90 (1H, doublet, J=6 Hz); 6.81 (1H, singlet); 9.97 (1H, doublet, J=8 Hz).

EXAMPLE 33

Pivaloyloxymethyl 7-[2-(2-aminothiazol-4-yl)-2-(syn-isobutyryloxyimino)acetamido]-3-(3-fluorophenoxy)methyl-3-cephem-4-carboxylate trifluoroacetate 300 mg of pivaloyloxymethyl 7-[2-(2-tritylaminothiazol-4-yl)-2-(syn-hydroxyimino)acetamido]-3-fluorophenoxy)methyl-3-cephem-4-carboxylate [prepared as described in Example 32(a)] and 0.06 ml of isobutyryl chloride were reacted and worked up by similar methods to those described in steps (b) and (c) of Example 32 to give 120 mg of the title compound in the form of a powder.

Nuclear Magnetic Resonance Spectrum (hexadeuterated dimethyl sulfoxide) δ ppm: 1.12 (9H, singlet); 1.14 (6H, doublet, J=7 Hz); 2.6–2.9 (1H, multiplet); 4.83 (2H, singlet); 5.27 (1H, doublet, J=5 Hz); 5.81 (1H, doublet, J=6 Hz); 5.90 (1H, doublet, J=6 Hz); 5.9–6.1 (1H, multiplet); 6.80 (1H, singlet); 9.91 (1H, doublet, J=8 Hz).

EXAMPLE 34

Pivaloyloxymethyl 7-[2-(2-aminothiazol-4-yl)-2-(syn-pivaloyloxyimino)acetamido]-3-(3-fluorophenoxy)methyl-3-cephem-4-carboxylate trifluoroacetate 300 mg of pivaloyloxymethyl 7-[2-(2-tritylaminothiazol-4-yl)-2-(syn-hydroxyimino)acetamido]-3-(3-fluorophenoxy)methyl-3-cephem-4-carboxylate [prepared as described in Example 32(a)] and 0.05 ml of pivaloyl chloride were reacted and worked up by similar methods to those described in steps (b) and (c) of Example 32 to give 160 mg of the title compound in the form of a powder.

Nuclear Magnetic Resonance Spectrum (hexadeuterated dimethyl sulfoxide) δ ppm: 1.12 (9H, singlet); 1.20 (9H, singlet); 4.84 (2H, singlet); 5.27 (1H, doublet, J=5 Hz); 5.80 (1H, doublet, J=6 Hz); 5.91 (1H, doublet, J=6 Hz); 5.8–6.0 (1H, multiplet); 6.80 (1H, singlet); 9.69 (1H, doublet, J=8 Hz).

EXAMPLE 35

Pivaloyloxymethyl 7-[2-(2-aminothiazol-4-yl)-2-(syn-butyryloxyimino)acetamido]-3-(3-fluorophenoxy)methyl-3-cephem-4-carboxylate trifluoroacetate 220 mg of pivaloyloxymethyl 7-[2-(2-tritylaminothiazol-4-yl)-2-(syn-hydroxyimino)acetamido]-3-(3-fluorophenoxy)methyl- 3-cephem-4-carboxylate [prepared as described in Example 32(a)] and 0.05 ml of butyryl chloride were reacted and worked up by similar methods to those described in steps (b) and (c) of Example 32 to give 110 mg of the title compound in the form of a powder.

Nuclear Magnetic Resonance Spectrum (hexadeuterated dimethyl sulfoxide) δ ppm: 0.91 (3H, triplet, J=8 Hz); 1.11 (9H, singlet); 1.5–1.7 (2H, multiplet); 2.50 (2H, triplet, J=8 Hz); 4.87 (2H, singlet); 5.28 (1H, doublet, J=5 Hz); 5.81 (1H, doublet, J=6 Hz); 5.90 (1H, doublet, J=6 Hz); 5.8–6.0 (1H, multiplet); 6.82 (1H, singlet); 9.90 (1H, doublet, J=8 Hz).

EXAMPLE 36

Pivaloyloxymethyl 7-[2-(2-aminothiazol-4-yl)-2-(syn-ethoxycarbonyloxyimino)acetamido]-3-(3-cyanophenoxy)-methyl-3-cephem-4-carboxylate trifluoroacetate 36(a) Pivaloyloxymethyl 7-[2-(2-tritylaminothiazol-4-yl)-2-(syn-hydroxyimino)acetamido]-3-(3-cyanophenoxy)methyl-3-cephem-4-carboxylate The procedures of step (a) of Example 45 (described below) and step (a) of Example 32 were repeated, but using 2.50 g of diphenylmethyl 3-(3-cyanophenoxy)-methyl-7-phenoxyacetamido-3-cephem-4-carboxylate [prepared as described in Example 12(a)], to give 1.27 g of the title compound in the form of a powder.

Nuclear Magnetic Resonance Spectrum (hexadeuterated dimethyl sulfoxide) δ ppm: 1.11 (9H, singlet); 4.84 (2H, singlet); 5.20 (1H, doublet, J=5 Hz); 5.74 (1H, doublet of doublets, J=5 & 8 Hz); 5.81 (1H, doublet, J=6 Hz); 5.89 (1H, doublet, J=6 Hz); 6.61 (1H, singlet); 9.47 (1H, doublet, J=8 Hz); 11.33 (1H, singlet).

36(b) Pivaloyloxymethyl 7-[2-(2-aminothiazol-4-yl)-2-(syn-ethoxycarbonyloxyimino)acetamido]-3-(3-cyanophenoxy)methyl-3-cephem-4-carboxylate trifluoroacetate 200 mg of pivaloyloxymethyl 7-[2-(2-tritylaminothiazol-4-yl)-2-(syn-hydroxyimino)acetamido]-3-(3-cyanophenoxy)methyl-3-cephem-4-carboxylate [prepared as described in step (a) above] and 0.06 ml of ethyl chloroformate were reacted and worked up by similar methods to those described in steps (b) and (c) of Example 32 to give 134 mg of the title compound in the form of a powder.

Nuclear Magnetic Resonance Spectrum (hexadeuterated dimethyl sulfoxide) δ ppm: 1.11 (9H, singlet); 1.26 (3H, triplet, J=7 Hz); 4.24 (2H, quartet, J=7 Hz); 4.84 (1H, doublet, J=12 Hz); 4.90 (1H, doublet, J=12 Hz); 5.26 (1H, doublet, J=5 Hz); 5.81 (1H, doublet, J=6 Hz); 5.90 (1H, doublet, J=6 Hz); 5.91 (1H, doublet of doublets, J=4 & 8 Hz); 7.07 (1H, singlet); 9.97 (1H, doublet, J=8 Hz).

EXAMPLE 37

Pivaloyloxymethyl 7-{2-(2-aminothiazol-4-yl)-2-[syn-(2-methoxyethoxy)-carbonyloxyimino]acetamido-3-(3-cyanophenoxy)methyl-3-cephem-4-carboxylate trifluoroacetate 2 00 mg of pivaloyloxymethyl 7-[2-(2-tritylamino-thiazol-4-yl)-2-(syn-hydroxyimino)acetamido]-3-(3-cyanophenoxy)methyl-3-cephem-4-carboxylate [prepared as described in Example 36(a)] and 0.04 ml of 2-methoxyethyl chloroformate were reacted and worked up by similar methods to those described in steps (b) and (c) of Example 32 to give 148 mg of the title compound in the form of a powder.
Nuclear Magnetic Resonance Spectrum (hexadeuterated dimethyl sulfoxide) δ ppm: 1.11 (9H, singlet); 3.26 (3H, singlet); 3.57 (2H, multiplet); 4.30 (2H, multiplet); 4.86 (2H, singlet); 5.26 (1H, doublet, J=5 Hz); 5.82 (1H, doublet of doublets, J=5 & 8 Hz); 7.07 (1H, singlet); 9.98 (1H, doublet, J=8 Hz).

EXAMPLE 38

Pivaloyloxymethyl 7-{2-(2-aminothiazol-4-yl)-2-[syn-(2-ethylhexyloxy)carbonyloxyimino]acetamido-3-(3-cyanophenoxy)methyl-3-cephem-4-carboxylate trifluoroacetate 200 mg of pivaloyloxymethyl 7-[2-(2-tritylamino-thiazol-4-yl)-2-(syn-hydroxyimino)acetamido]-3-(3-cyanophenoxy)methyl-3-cephem-4-carboxylate [prepared as described in Example 36(a)] and 0.07 ml of 2-ethylhexyl chloroformate were reacted and worked up by similar methods to those described in steps (b) and (c) of Example 32 to give 103 mg of the title compound in the form of a powder.
Nuclear Magnetic Resonance Spectrum (hexadeuterated dimethyl sulfoxide) δ ppm: 0.85 (6H, triplet, J=7 Hz); 1.11 (9H, singlet); 4.1–4.3 (2H, multiplet); 4.84 (1H, doublet, J=12 Hz); 4.91 (1H, doublet, J=12 Hz); 5.27 (1H, doublet, J=5 Hz); 5.81 (1H, doublet, J=6 Hz); 5.85 (1H, doublet of doublets, J=5 & 8 Hz); 5.90 (1H, doublet, J=6 Hz); 7.08 (1H, singlet); 9.97 (1H, doublet, J=8 Hz).

EXAMPLE 39

Pivaloyloxymethyl 7-[2-(2-aminothiazol-4-yl)-2-(syn-butyryloxyimino)acetamido]-3-(3-cyanophenoxy)methyl-3-cephem-4-carboxylate trifluoroacetate 200 mg of pivaloyloxymethyl 7-[2-(2-tritylamino-thiazol- 4-yl)-2-(syn-hydroxyimino)acetamido]-3-(3-cyanophenoxy)methyl-3-cephem-4-carboxylate [prepared as described in Example 36(a)] and 0.04 ml of butyryl chloride were reacted and worked up by similar methods to those described in steps (b) and (c) of Example 32 to give 115 mg of the title compound in the form of a powder.
Nuclear Magnetic Resonance Spectrum (hexadeuterated dimethyl sulfoxide) δ ppm: 0.91 (3H, triplet, J=8 Hz); 1.11 (9H, singlet); 1.5–1.7 (2H, multiplet); 2.50 (2H, triplet, J=8 Hz); 4.87 (2H, singlet); 5.28 (1H, doublet, J=5 Hz); 5.81 (1H, doublet, J=6 Hz); 5.84 (1H, doublet of doublets, J=5 & 8 Hz); 5.90 (1H, doublet, J=6 Hz); 7.08 (1H, singlet); 9.90 (1H, doublet, J=8 Hz).

EXAMPLE 40

Pivaloyloxymethyl 7-[2-(syn-2-aminopropionyloxyimino)-2-(2-aminothiazol-4-yl)acetamido]-3-(3-cyanophenoxy)methyl-3-cephem-4-carboxylate trifluoroacetate 400 mg of pivaloyloxymethyl 7-[2-(2-tritylamino-thiazol-4-yl)-2-(syn-hydroxyimino)acetamido]-3-(3-cyanophenoxy)methyl-3-cephem-4-carboxylate [prepared as described in Example 36(a)] and 125 mg of t-butoxycarbonyl-L-alanine were dissolved in 10 ml of methylene chloride. 122 mg of dicyclohexylcarbodiimide were added to the resulting solution, and then the mixture was stirred at room temperature for 1 hour. At the end of this time, the crystals which had separated were filtered off, and the filtrate was concentrated under reduced pressure to give 220 mg of a powder. This powder was reacted and worked up by similar a method to that described in step (c) of Example 32 to give 103 mg of the title compound in the form of a powder.
Nuclear Magnetic Resonance Spectrum (hexadeuterated dimethyl sulfoxide) δ ppm: 1.11 (9H, singlet); 1.47 (3H, triplet, J=7 Hz); 4.1–4.3 (1H, multiplet); 4.88 (2H, singlet); 5.30 (1H, doublet, J=5 Hz); 5.82 (1H, doublet, J=6 Hz); 5.90 (1H, doublet, J=6 Hz); 5.92 (1H, doublet of doublets, J=5 & 8 Hz); 7.18 (1H, singlet); 10.00 (1H, doublet, J=8 Hz).

EXAMPLE 41

7-[2-(2-Aminothiazol-4-yl)-2-(syn-difluoromethoxyimino)acetamido]-3-(3-fluorophenoxy)methyl-3-cephem-4-carboxylic acid trifluoroacetate 1.00 g of diphenylmethyl 3-(3-fluorophenoxy)methyl-7-phenoxyacetamido-3-cephem-4-carboxylate [prepared as described in Example 3(a)] and 560 mg of 2-(syn-difluoromethoxyimino)-2-(2-tritylaminothiazol-4-yl)acetic acid were reacted and worked up by similar methods to those described in steps (b), (c) and (d) of Example 3 to give 282 mg of the title compound in the form of a powder.
Nuclear Magnetic Resonance Spectrum (hexadeuterated dimethyl sulfoxide) δ ppm: 3.58 (1H, doublet, J=18 Hz); 3.70 (1H, doublet, J=18 Hz); 4.83 (1H, doublet, J=12 Hz); 4.90 (1H, doublet, J=12 Hz); 5.23 (1H, doublet, J=5 Hz); 5.83 (1H, doublet of doublets, J=5 & 8 Hz); 7.01 (1H, singlet); 7.13 (1H, triplet, J=65 Hz); 9.97 (1H, doublet, J=8 Hz).

EXAMPLE 42

Pivaloyloxymethyl 7-[2-(2-aminothiazol-4-yl)-2-(syn-difluoromethoxyimino)acetamido]-3-(3-fluorophenoxy)methyl-3-cephem-4-carboxylate 150 mg of 7-[2-(2-aminothiazol-4-yl)-2-(syn-difluoromethoxyimino)acetamido]-3-(3-fluorophenoxy)methyl-3-cephem-4-carboxylic acid trifluoroacetate (prepared as described in Example 41) were reacted and worked up by similar methods to those described in Examples 18 and 19 to give 100 mg of the title compound in the form of a powder.
Nuclear Magnetic Resonance Spectrum (hexadeuterated dimethyl sulfoxide) δ ppm: 1.11 (9H, singlet); 3.64 (1H, doublet, J=18 Hz); 3.75 (1H, doublet, J=18 Hz); 4.80 (1H, doublet, J=12 Hz); 4.87 (1H, doublet, J=12 Hz); 5.26 (1H, doublet, J=5 Hz); 5.88 (1H, doublet of doublets, J=5 & 8 Hz); 7.00 (1H, singlet); 7.12 (1H, triplet, J=69 Hz); 9.97 (1H, doublet, J=8 Hz).

EXAMPLE 43

7-[2-(2-Aminothiazol-4-yl)-2-(syn-fluoromethoxyimino)acetamido]-3-(3-fluorophenoxy)methyl-3-cephem-4-carboxylic acid trifluoroacetate 1.00 g of diphenylmethyl 3-(3-fluorophenoxy)methyl-7-phenoxyacetamido-3-cephem-4-carboxylate [prepared as described in Example 3(a)] and 500 mg of 2-(syn-fluoromethoxyimino)-2-(2-tritylaminothiazol-4-yl)acetic acid were reacted and worked up by similar methods to those described in steps (b), (c) and (d) of Example 3 to give 310 mg of the title compound in the form of a powder.

Nuclear Magnetic Resonance Spectrum (hexadeuterated dimethyl sulfoxide) δ ppm: 4.82 (1H, doublet, J=12 Hz); 4.90 (1H, doublet, J=12 Hz); 5.22 (1H, doublet, J=5 Hz); 5.75 (1H, doublet, J=55 Hz); 5.82 (1H, doublet of doublets, J=5 & 8 Hz); 6.95 (1H, singlet); 9.86 (1H, doublet, J=8 Hz).

EXAMPLE 44

Pivaloyloxymethyl 7-[2-(2-aminothiazol-4-yl)-2-(syn-fluoromethoxyimino)acetamido]-3-(3-fluorophenoxy)methyl-3-cephem-4-carboxylate 200 mg of 7-[2-(2-aminothiazol-4-yl)-2-(syn-fluoromethoxyimino)acetamido]-3-(3-fluorophenoxy)methyl-3-cephem-4-carboxylic acid trifluoroacetate (prepared as described in Example 43) were reacted and worked up by similar methods to those described in Examples 18 and 19 to give 73 mg of the title compound in the form of a powder.

Nuclear Magnetic Resonance Spectrum (hexadeuterated dimethyl sulfoxide) δ ppm: 1.11 (9H, sinblet); 4.82 (2H, singlet); 5.26 (1H, doublet, J=5 Hz); 5.75 (1H, doublet, J=55 Hz); 5.82 (1H, doublet, J=6 Hz); 5.89 (1H, doublet, J=6 Hz); 5.8–6.0 (1H, multiplet); 6.80 (1H, singlet); 9.85 (1H, doublet, J=8 Hz).

EXAMPLE 45

Pivaloyloxymethyl 7-[2-(2-aminothiazol-4-yl)-2-(syn-pivaloyloxymethoxyimino)acetamido]-3-(3-fluorophenoxy)methyl-3-cephem-4-carboxylate trifluoroacetate 45(a) Pivaloyloxymethyl 7-amino-3-(3-fluorophenoxy)methyl-3-cephem-4-carboxylate hydrochloride 3.61 g of diphenylmethyl 3-(3-fluorophenoxy)methyl-7-phenoxyacetamido-3-cephem-4-carboxylate [prepared as described in Example 3(a)] were dissolved in a mixture of 0.8 ml of anisole, 4.5 ml of trifluoroacetic acid and 10 ml of methylene chloride, and then the solution was stirred for 1 hour, whilst ice-cooling. At the end of this time, diisopropyl ether was added to the reaction mixture to give 2.60 g of a precipitate, which was collected by filtration and dissolved in 30 ml of methanol. A solution of 1.41 g of sodium 2-ethylhexanoate in 10 ml of methanol was added at room temperature, and then the mixture was stirred for 15 minutes. Diiosopropyl ether was then added to give a precipitate, which was collected by filtration to give 1.80 g of the sodium salt. The whole of this salt was stirred, whilst ice-cooling, for 1 hour in a solution of 1.1 ml of pivaloyl iodide in 50 ml of dimethylacetamide. The reaction mixture was then diluted with ethyl acetate, washed with water and dried over anhydrous sodium sulfate, after which the solvent was removed by distillation under reduced pressure to give a residue, which was purified by column chromatography through silica gel to give 1.58 g of the pivaloyloxymethyl ester in the form of a powder.

Meanwhile, 0.43 ml of pyridine was added dropwise to a solution of 970 mg of phosphorus pentachloride in 30 ml of chloroform at room temperature and then the mixture was stirred for 15 minutes. A solution of the whole of the pivaloyloxymethyl ester (which had been prepared as described above) in 10 ml of chloroform was added dropwise to the mixture, whilst ice-cooling, and then the whole mixture was stirred at room temperature for 1 hour. At the end of this time, the mixture was cooled to −30° C., and 2.7 ml of propanol were added. The whole mixture was then allowed to warm gradually to room temperature. The reaction mixture was then diluted with methylene chloride, washed with a small volume of a saturated aqueous solution of sodium chloride and dried over anhydorus sodium sulfate. The solvent was then removed by evaporation Under reduced pressure to leave a residue, which was formed into a powder by the addition of diisopropyl ether, to give 1.30 g of the title compound.

Nuclear Magnetic Resonance Spectrum (hexadeuterated dimethyl sulfoxide) δ ppm: 1.12 (9H, singlet); 3.80 (2H, singlet); 4.85 (1H, doublet, J=12 Hz); 4.92 (1H, doublet, J=12 Hz); 5.25 (1H, doublet, J=5 Hz); 5.30 (1H, doublet, J=5 Hz); 5.82 (1H, doublet. J=6 Hz); 5.91 (1H, doublet. J=6 Hz); 6.7–6.9 (3H, multiplet); 7.2–7.4 (1H, multiplet).

45(b) Pivaloyloxymethyl 7-[2-(2-aminothiazol-4-yl)-2-(syn-pivaloyloxymethoxyimino)acetamido]-3-(3-fluorophenoxy)methyl-3-cephem-4-carboxylate trifluoroacetate 420 mg of pivaloyloxymethyl 7-amino-3-(3-fluorophenoxy)methyl-3-cephem-4-carboxylate hydrochloride [prepared as described in step (a) above] and 700 mg of 2-(syn-pivaloyloxymethoxyimino)-2-(2-tritylaminothiazol-4-yl)acetic acid were reacted and worked up by a similar method to that described in Example 1(b), after which the reaction product was treated with trifluoroacetic acid, to give 78 mg of the title compound in the form of a powder.

Nuclear Magnetic Resonance Spectrum (hexadeuterated dimethyl sulfoxide) δ ppm: 1.12 (9H, singlet); 1.15 (9H, singlet); 4.79 (1H, doublet, J=12 Hz); 4.85 (1H, doublet, J=12 Hz); 5.24 (1H, doublet, J=5 Hz); 5.70 (2H, singlet); 5.81 (1H, doublet, J=6 Hz); 5.86 (1H, doublet of doublets, J=5 & 8 Hz); 5.90 (1H, doublet, J=6 Hz); 6.86 (1H, singlet); 9.74 (1H, doublet, J=8 Hz).

EXAMPLE 46

Pivaloyloxymethyl 7-[2-(2-aminothiazol-4-yl)-2-(syn-methoxyimino)acetamido]-3-(3-fluorophenoxy)methyl-3-cephem-4-carboxylate 100 mg of 7-[2-(2-aminothiazol-4-yl)-2-(syn-methoxyimino)acetamido]-3-(3-fluorophenoxy)methyl-3-cephem-4-carboxylic acid trifluoroacetate (prepared as described in Example 11) were reacted and worked up by similar methods to those described in Examples 18 and 19 to give 65 mg of the title compound in the form of a powder.

Nuclear Magnetic Resonance Spectrum (hexadeuterated dimethyl sulfoxide) δ ppm: 1.12 (9H, singlet); 3.84 (3H, singlet); 4.81 (2H, singlet); 5.23 (1H, doublet, J=5 Hz); 5.81 (1H, doublet, J=6 Hz); 5.89 (1H, doublet, J=6 Hz); 5.8–6.0 (1H, multiplet); 6.75 (1H, singlet); 9.63 (1H, doublet, J=8 Hz).

EXAMPLE 47

7-[2-(2-Aminothiazol-4-yl)-2-(syn-hydroxyimino)acetamido]-3-(2-cyanophenoxy)methyl-3-cephem-4-carboxylic acid trifluoroacetate The procedure described in Example 1 was repeated, but using 2.0 g of diphenylmethyl 7-phenoxyacetamido-3-hydroxymethyl-3-cephem-4-carboxylate and 0.53 g of o-cyanophenol, to give 0.21 g of the title compound in the form of a powder.
Nuclear Magnetic Resonance Spectrum (hexadeuterated dimethyl sulfoxide) δ ppm: 4.99 (1H, doublet, J=12 Hz); 5.06 (1H, doublet, J=12 Hz); 5.24 (1H, doublet, J=5 Hz); 5.83 (1H, doublet of doublets, J=5 & 8 Hz); 6.76 (1H, singlet); 9.61 (1H, doublet, J=8 Hz). 11.79 (1H, singlet).

EXAMPLE 48

7-[2-(2-Aminothiazol-4-yl)-2-syn-hydroxyimino)acetamido]-3-(4-methylthiophenoxy)methyl-3-cephem-4-carboxylic acid trifluoroacetate The procedure described in Example 1 was repeated, but using 5.0 g of diphenylmethyl 7-phenoxyacetamido-3-hydroxymethyl-3-cephem-4-carboxylate and 1.99 g of p-methylthiophenol, to give 0.207 g of the title compound in the form of a powder.
Nuclear Magnetic Resonance Spectrum (hexadeuterated dimethyl sulfoxide) δ ppm: 2.41 (3H, singlet); 4.83 (2H, singlet); 5.18 (1H, doublet, J=5 Hz); 5.80 (1H, doublet of doublets, J=5 & 8 Hz); 6.73 (1H, singlet); 9.54 (1H, doublet, J=8 Hz). 11.62 (1H, singlet).

EXAMPLE 49

7-[2-(2-Aminothiazol-4-yl)-2-(syn-hydroxyimino)acetamido]-3-(3-methylphenoxy)methyl-3-cephem-4-carboxylic acid trifluoroacetate The procedure described in Example 1 was repeated, but using 4.0 g of diphenylmethyl 7-phenoxyacetamido-3-hydroxymethyl-3-cephem-4-carboxylate and 1.20 ml of m-cresol, to give 0.027 g of the title compound in the form of a powder.
Nuclear Magnetic Resonance Spectrum (hexadeuterated dimethyl sulfoxide) δ ppm: 2.26 (3H, singlet); 5.04 (2H, singlet); 5.19 (1H, doublet, J=5 Hz); 5.94 (1H, doublet of doublets, J=5 & 8 Hz); 6.74 (1H, singlet); 9.61 (1H, doublet, J=8 Hz). 11.66 (1H, singlet).

EXAMPLE 50

7-[2-(2-Aminothiazol-4-yl)-2-(syn-hydroxyimino)acetamido]-3-(3-trifluoromethylphenoxy)methyl-3-cephem-4-carboxylic acid trifluoroacetate The procedure described in Example 1 was repeated, but using 4.0 g of diphenylmethyl 7-phenoxyacetamido-3-hydroxymethyl-3-cephem-4-carboxylate and 1.08 ml of m-trifluoromethylphenol, to give 0.146 g of the title compound in the form of a powder.
Nuclear Magnetic Resonance Spectrum (hexadeuterated dimethyl sulfoxide) δ ppm: 4.88 (1H, doublet, J=12 Hz); 4.96 (1H, doublet, J=12 Hz); 5.19 (1H, doublet, J=5 Hz); 5.81 (1H, doublet of doublets, J=5 & 8 Hz); 6.72 (1H, singlet); 9.54 (1H, doublet, J=8 Hz). 11.57 (1H, singlet).

EXAMPLE 51

7-[2-(2-Aminothiazol-4-yl)-2-(syn-hydroxyimino)acetamido]-3-(3,4,5-trimethoxyphenoxy)methyl-3-cephem-4-carboxylic acid trifluoroacetate The procedure described in Example 1 was repeated, but using 6.0 g of diphenylmethyl 7-phenoxyacetamido-3-hydroxymethyl-3-cephem-4-carboxylate and 3.13 g of 3,4,5-trimethoxyphenol, to give 0.093 g of the title compound in the form of a powder.
Nuclear Magnetic Resonance Spectrum (hexadeuterated dimethyl sulfoxide) δ ppm: 3.73 (9H, singlet); 4.80 (1H, doublet, J=12 Hz); 4.84 (1H, doublet, J=12 Hz); 5.18 (1H, doublet, J=5 Hz); 5.80 (1H, doublet of doublets, J=5 & 8 Hz); 6.71 (1H, singlet); 9.53 (1H, doublet, J=8 Hz). 11.59 (1H, singlet).

EXAMPLE 52

7-[2-(2-Aminothiazol-4-yl)-2-(syn-hydroxyimino)acetamido]-3-(4-acetylaminophenoxy)methyl-3-cephem-4-carboxylic acid trifluoroacetate The procedure described in Example 1 was repeated, but using 6.0 g of diphenylmethyl 7-phenoxyacetamido-3-hydroxymethyl-3-cephem-4-carboxylate and 2.84 g of p-acetylaminophenol, to give 0.252 g of the title compound in the form of a powder.
Nuclear Magnetic Resonance Spectrum (hexadeuterated dimethyl sulfoxide) δ ppm: 1.99 (3H, singlet); 4.81 (2H, singlet); 5.18 (1H, doublet, J=5 Hz); 5.79 (1H, doublet of doublets, J=5 & 8 Hz); 6.75 (1H, singlet); 9.56 (1H, doublet, J=8 Hz). 9.77 (1H, singlet); 11.70 (1H, singlet).

EXAMPLE 53

7-[2-(2-Aminothiazol-4-yl)-2-(syn-hydroxyimino)acetamido]-3-(4-methoxycarbonylphenoxy)-methyl-3-cephem-4-carboxylic acid trifluoroacetate The procedure described in Example 1 was repeated, but using 6.0 g of diphenylmethyl 7-phenoxyacetamido-3-hydroxymethyl-3-cephem-4-carboxylate and 2.59 g of methyl p-hydroxybenzoate, to give 0.527 g of the title compound in the form of a powder.
Nuclear Magnetic Resonance Spectrum (hexadeuterated dimethyl sulfoxide) δ ppm: 3.81 (3H, singlet); 4.92 (2H, singlet); 5.20 (1H, doublet, J=5 Hz); 5.81 (1H, doublet of doublets, J=5 & 8 Hz); 6.74 (1H, singlet); 9.57 (1H, doublet, J=8 Hz). 11.70 (1H, singlet).

EXAMPLE 54

7-[2-(2-Aminothiazol-4-yl)-2-(syn-hydroxyimino)acetamido]-3-(4-ethoxycarbonylphenoxy)methyl-3-cephem-4-carboxylic acid trifluoroacetate The procedure described in Example 1 was repeated, but using 5.0 g of diphenylmethyl 7-phenoxyacetamido-3-hydroxymethyl-3-cephem-4-carboxylate and 2.35 g of ethyl p-hydroxybenzoate, to give 0.323 g of the title compound in the form of a powder.
Nuclear Magnetic Resonance Spectrum (hexadeuterated dimethyl sulfoxide) δ ppm: 1.30 (3H, triplet, J=8 Hz); 4.27 (2H, quartet, J=8 Hz); 4.92 (2H, singlet); 5.19 (1H, doublet, J=5 Hz); 5.81 (1H, doublet of doublets, J=5 & 8 Hz); 6.71 (1H, singlet); 9.54 (1H, doublet, J=8 Hz). 11.59 (1H, singlet).

EXAMPLE 55

7-[2-(2-Aminothiazol-4-yl)-2-(syn-hydroxyimino)acetamido]-3-(4-methoxycarbonylmethylphenoxy)methyl-3-cephem-4-carboxylic acid trifluoroacetate The procedure described in Example 1 was repeated, but using 5.0 g of diphenylmethyl 7-phenoxyacetamido-3hydroxymethyl-3-cephem-4-carboxylate and 2.35 g of methyl p-hydroxyphenylacetate, to give 0.406 g of the title compound in the form of a powder.

Nuclear Magnetic Resonance Spectrum (hexadeuterated dimethyl sulfoxide) δ ppm: 3.59 (3H, singlet); 4.83 (2H, singlet); 5.19 (1H, doublet, J=5 Hz); 5.80 (1H, doublet of doublets, J=5 & 8 Hz); 6.72 (1H, singlet); 9.54 (1H, doublet, J=8 Hz). 11.61 (1H, singlet).

EXAMPLE 56

7-[2-(2-Aminothiazol-4-yl)-2-(syn-hydroxyimino)acetamido]-3-[4-(2-hydroxyethyl)phenoxy]methyl-3-cephem-4-carboxylic acid trifluoroacetate The procedure described in Example 1 was repeated, but using 5.0 g of diphenylmethyl 7-phenoxyacetamido-3-hydroxymethyl-3-cephem-4-carboxylate and 3.30 g of p-trityloxyethylphenol, to give 0.029 g of the title compound in the form of a powder.

Nuclear Magnetic Resonance Spectrum (hexadeuterated dimethyl sulfoxide) δ ppm: 2.8–3.0 (2H, multiplet); 4.82 (2H, singlet); 5.18 (1H, doublet, J=5 Hz); 5.80 (1H, doublet of doublets, J=5 & 8 Hz); 6.73 (1H, singlet); 9.54 (1H, doublet, J=8 Hz). 11.62 (1H, singlet).

EXAMPLE 57

7-[2-(2-Aminothiazol-4-yl)-2-(syn-hydroxyimino)acetamido]-3-(4-methylsulfinylphenoxy)methyl-3-cephem-4-carboxylic acid trifluoroacetate The procedure described in steps (a), (b) and (c) of Example 1 was repeated, but using 10.0 g of diphenylmethyl 7-phenoxyacetamido-3-hydroxymethyl-3-cephem-4-carboxylate and 3.98 g of p-methylthiophenol. The reaction product was then dissolved in a mixture of 66.2 ml of methylene chloride and 5.0 ml of methanol. 0.196 g of m-perbenzoic acid was added, and then the mixture was allowed to react at an inner temperature of between −50° C. and −35° C. for 30 minutes, after which it was worked up by a similar procedure to that described in step (d) of Example 1, to give 0.142 g of the title compound in the form of a powder.

Nuclear Magnetic Resonance Spectrum (hexadeuterated dimethyl sulfoxide) δ ppm: 2.69 (3H, singlet); 4.88 (1H, doublet, J=12 Hz); 4.94 (1H, doublet, J=12 Hz); 5.20 (1H, doublet, J=5 Hz); 5.81 (1H, doublet of doublets, J=5 & 8 Hz); 6.73 (1H, singlet); 9.56 (1H, doublet, J=8 Hz). 11.65 (1H, singlet).

EXAMPLE 58

7-[2-(2-Aminothiazol-4-yl)-2-(syn-benzoyloxyimino)acetamido]-3-(3-fluorophenoxy)methyl-3-cephem-4-carboxylic acid trifluoroacetate The procedure described in steps (b) and (c) of Example 32 was repeated, but using 300 mg of pivaloyloxymethyl 7-[2-(2-tritylaminothiazol-4-yl)-2-syn-hydroxyimino)acetamido]-3-(3-fluorophenoxy)methyl-3-cephem-4-carboxylate [prepared as described in Example 32(a)] and 0.06 ml of benzoyl chloride, to give 182 mg of the title compound in the form of a powder.

Nuclear Magnetic Resonance Spectrum (hexadeuterated dimethyl sulfoxide) δ ppm: 1.11 (9H, singlet); 4.83 (2H, singlet); 5.30 (1H, doublet, J=5 Hz); 5.82 (1H, doublet, J=6 Hz); 5.94 (1H, doublet, J=6 Hz); 6.02 (1H, doublet of doublets, J=5 & 8 Hz); 8.02 (2H, doublet, J=8 Hz); 10.08 (1H, doublet, J=8 Hz).

EXAMPLE 59

7-[2-(2-Aminothiazol-4-yl)-2-(syn-carboxymethoxyimino)acetamido]-3-(3-fluorophenoxy)methyl-3-cephem-4-carboxylic acid trifluoroacetate 59(a) Diphenylmethyl 7-amino-3-(3-fluorophenoxy)-methyl-3-cephem-4-carboxylate hydrochloride The procedure described in Example 1(b) was repeated, but using 700 mg of diphenylmethyl 3-(3-fluorophenoxy)methyl-7-phenoxyacetamido-3-cephem-4-carboxylate [prepared as described in Example 3(a)], to give 580 mg of the title compound.

Nuclear Magnetic Resonance Spectrum (CDCl$_3$) δ ppm: 3.52 (1H, doublet, J=17 Hz); 3.82 (1H, doublet, J=17 Hz); 4.74 (1H, doublet, J=14 Hz); 4.97 (1H, broad singlet); 4.99 (1H, doublet, J=14 Hz); 6.4–7.4 (18H, multiplet).

59(b) Diphenylmethyl 7-[2-(2-aminothiazol-4-yl)-2-(syn-t-butoxycarbonylmethoxyimino)acetamido]-3-(3-fluorophenoxy)methyl-3-cephem-4-carboxylate The whole of the compound obtained in step (a) above was neutralized with an equimolar amount of sodium bicarbonate, after which it was dissolved, together with 560 mg of benzothiazol-2-ylthio 2-(aminothiazol-4-yl)-2-(syn-t-butoxycarbonylmethoxyimino-)acetate, in 5 ml of methylene chloride. After the solution had been allowed to stand overnight at room temperature, it was diluted with ethyl acetate, washed, in turn, with an aqueous solution of sodium bicarbonate and with an aqueous solution of sodium chloride and then dried. The solvent was then removed by evaporation under reduced pressure, and the residue was purified by column chromatography through silica gel, eluted with a 1:1 by volume mixture of ethyl acetate and hexane, to give 422 mg of the title compound as a foam.

Nuclear Magnetic Resonance Spectrum (CDCl$_3$) δ ppm: 1.42 (9H, singlet); 3.53 (1H, doublet, J=17 Hz); 3.60 (1H, doublet, J=17 Hz); 4.5–5.0 (4H, multiplet); 5.09 (1H, doublet, J=5 Hz); 5.96 (1H, doublet of doublets, J=5 & 9 Hz); 6.4–7.8 (18H, multiplet); 8.7 (1H, doublet, J=7 Hz).

59(c) 7-[2-(2-Aminothiazol-4-yl)-2-(syn-carboxymethoxyimino)acetamido]-3-(3-fluorophenoxy)methyl-3-cephem-4-carboxylic acid trifluoroacetate 380 mg of diphenylmethyl 7-[2-(2-aminothiazol-4-yl)-2-(syn-t-butoxycarbonylmethoxyimino)acetamido]-3-(3-fluorophenoxy)methyl-3-cephem-4-carboxylate [prepared as described in step (a) above] were dissolved in a mixture of 1 ml of anisole, 4 ml of trifluoroacetic acid and 1 ml of methylene chloride, and then the mixture was stirred at room temperature for 3 hours. At the end of this time, a powder was precipitated from the reaction mixture by the addition of diisopropyl ether, to give 133 mg of the title compound.

Nuclear Magnetic Resonance Spectrum (CDCl$_3$) δ ppm: 4.61 (2H, singlet); 4.82 (1H, doublet, J=12 Hz); 4.90 (1H, doublet, J=12 Hz); 5.21 (1H, doublet, J=5 Hz); 5.84 (1H, doublet of doublets, J=5 & 8 Hz); 6.83 (1H, singlet); 9.58 (1H, doublet, J=8 Hz).

EXAMPLE 60

7-[2-(Furan-2-yl)-2-(syn-methoxyimino)acetamido]-3-(3-fluorophenoxy)methyl-3-cephem-4-carboxylic acid 60(a) Diphenylmethyl 3-(3-fluorophenoxy)methyl-7-[2-(furan-2-yl)-2-(syn-methoxyimino)acetamido]-3-cephem-4-carboxylate The procedure described in Example 1(b) was repeated, but using 500 mg of diphenylmethyl 7-amino-3-(3-fluorophenoxy)methyl-3-cephem-4-carboxylate hydrochloride [prepared as described in step Example 59(a)] and 192 mg of 2-(furan-2-yl)-2-(syn-methoxyimino)acetic acid, to give 250 mg of the title compound in the form of a foam.

Nuclear Magnetic Resonance Spectrum (CDCl$_3$) δ ppm: 3.63 (2H, broad singlet); 4.09 (3H, singlet); 4.80 (1H, doublet, J=13 Hz); 4.92 (1H, doublet, J=13 Hz); 5.09 (1H, doublet, J=5 Hz); 5.98 (1H, doublet of doublets, J=5 & 9 Hz); 6.4–7.6 (19H, multiplet).

60(b) 3-(3-Fluorophenoxy)methyl-7-[2-(Furan-2-yl)-2-(syn-methoxyimino)acetamido]-3-cephem-4-carboxylic acid The procedure described in Example 1(d) was repeated, but using the whole of the compound obtained in step (a) above, and the precipitation was effected using a mixture of diisopropyl ether and hexane, to give 120 mg of the title compound in the form of a powder.

Nuclear Magnetic Resonance Spectrum (hexadeuterated dimethyl sulfoxide) δ ppm: 3.90 (3H, singlet); 4.82 (1H, doublet, J=12 Hz); 4.90 (1H, doublet, J=12 Hz); 5.22 (1H, doublet, J=5 Hz); 5.83 (1H, doublet of doublets, J=5 & 8 Hz); 7.82 (1H, doublet, J=2 Hz); 9.84 (1H, doublet, J=8 Hz).

EXAMPLE 61

7-[2-Amino-2-phenylacetamido]-3-(3-fluorophenoxy)methyl-3-cephem-4-carboxylic acid trifluoroacetate 61(a) Diphenylmethyl 3-(3-fluorophenoxy)methyl-7-[2-phenyl-2-(t-butoxycarbonylamino)acetamido]-3-cephem-4-carboxylate A solution of 335 mg of t-butoxycarbonyl-D-phenylglycine, 651 mg of diphenylmethyl 7-amino-3-(3-fluorophenoxy)methyl-3-cephem-4-carboxylate and 330 mg of 2-ethoxy-1-ethoxycarbonyl-1,2-dihydroquinoline in 5 ml of methylene chloride was allowed to stand at room temperature for 4 hours. At the end of this time, the reaction mixture was washed, in turn, with an aqueous solution of sodium bicarbonate, with an aqueous solution of sodium chloride, with an aqueous solution of sodium bicarbonate and with an aqueous solution of sodium chloride, and then dried. The solvent was then removed by evaporation under reduced pressure and the residue was purified by column chromatogrpahy through silica gel, eluted with a 2:3 by volume mixture of ethyl acetate and hexane, to give 457 mg of the title compound in the form of a foam.

Nuclear Magnetic Resonance Spectrum (CDCl$_3$) δ ppm: 1.42 (9H, singlet); 3.44 (1H, doublet, J=19 Hz); 3.53 (1H, doublet, J=19 Hz); 4.72 (1H, doublet, J=14 Hz); 4.86 (1H, doublet, J=14 Hz); 4.93 (1H, doublet, J=5 Hz); 5.19 (1H, broad singlet); 5.61 (1H, doublet, J=6 Hz); 5.84 (1H, doublet of doublets, J=5 & 9 Hz); 6.4–7.5 (21H, multiplet).

61(b) 7-[2-Amino-2-phenylacetamido]-3-(3-fluorophenoxy)methyl-3-cephem-4-carboxylic acid The procedure described in Example 1(d) was repeated, except that 420 mg of diphenylmethyl 3-(3-fluorophenoxy)methyl-7-[2-phenyl-2-(t-butoxycarbonylamino)acetamido]-3-cephem-4-carboxylate [prepared as described in step (a) above] were used and the reaction was effected at room temperature for 2 hours, to give 300 mg of the title compound in the form of a powder.

Nuclear Magnetic Resonance Spectrum (hexadeuterated dimethyl sulfoxide) δ ppm: 4.78 (1H, doublet, J=12 Hz); 4.86 (1H, doublet, J=12 Hz); 5.03 (1H, singlet); 5.08 (1H, doublet, J=5 Hz); 5.79 (1H, doublet of doublets, J=5 & 8 Hz); 9.58 (1H, doublet, J=8 Hz).

EXAMPLE 62

Tetradecanoyloxymethyl 7-[(2-aminothiazol-4-yl)-3-(3-fluorophenoxy)methyl-2-(syn-hydroxyimino)acetamido]-3-cephem-4-carboxylate The procedure described in Example 19 was repeated, but using 200 mg of sodium 7-[2-(2-aminothiazol-4-yl)-2-(syn-hydroxyimino)acetamido]-3-(3-fluorophenoxy)methyl-3-cephem-4-carboxylate (prepared as described in Example 18) and 200 mg of tetradecanoyloxymethyl iodide, to give 51 mg of the title compound in the form of a powder.

Nuclear Magnetic Resonance Spectrum (hexadeuterated dimethyl sulfoxide) δ ppm: 0.85 (3H, broad triplet); 4.80 (2H, singlet); 5.21 (1H, doublet, J=5 Hz); 5.8–5.9 (3H, multiplet); 6.66 (1H, singlet); 9.48 (1H, doublet, J=8 Hz); 11.35 (1H, singlet).

EXAMPLE 63

Benzoyloxymethyl 7-[(2-aminothiazol-4-yl)-3-(3-fluorophenoxy)methyl-2-(syn-hydroxyimino)acetamido]-3-cephem-4-carboxylate The procedure described in Example 19 was repeated, but using 204 mg of sodium 7-[2-(2-aminothiazol-4-yl)-2-(syn-hydroxyimino)acetamido]-3-(3-fluorophenoxy)methyl-3-cephem-4-carboxylate (prepared as described in Example 18) and 197 mg of benzoyloxymethyl iodide, to give 54 mg of the title compound in the form of a powder.

Nuclear Magnetic Resonance spectrum (hexadeuterated dimethyl sulfoxide) δ ppm: 4.82 (2H, singlet); 5.25 (1H, doublet, J=5 Hz); 5.82 (1H, doublet of doublets, J=5 & 8 Hz); 6.08 (1H, doublet, J=6 Hz); 6.16 (1H, doublet, J=6 Hz); 6.5–8.0 (10H, multiplet); 9.45 (1H, doublet, J=8 Hz); 11.3 (1H, singlet).

EXAMPLE 64

Pivaloyloxymethyl 7-[(2-aminothiazol-4-yl)-2-(syn-2-aminoethoxycarbonyloxymethoxyimino)acetamido]-3-(3-fluorophenoxy)methyl-3-cephem-4-carboxylate trifluoroacetate The procedures described in step (b) of Example 1 and step (c) of Example 32 were repeated, but using 700 mg of pivaloyloxymethyl 7-amino-3-(3-fluorophenoxy)methyl-3-cephem-4-carboxylate hydrochloride [prepared as described in Example 45(a)] and 1.30 g of 2-(syn-t-butoxycarbonylaminoethoxycarbonyloxymethoxyimino)-2-(2-tritylaminothiazol-4-yl)acetic acid, to give 210 mg of the title compound in the form of a powder.

Nuclear Magnetic Resonance Spectrum (hexadeuterated dimethyl sulfoxide) δ ppm: 1.11 (9H, singlet); 3.1–3.3 (2H, multiplet); 4.31 (2H, triplet, J=5 Hz); 4.82 (2H, singlet); 5.24 (1H, doublet, J=5 Hz); 5.72 (1H, doublet, J=7 Hz); 5.76 (1H, doublet, J=7 Hz); 5.82 (1H, doublet, J=6 Hz); 5.89 (1H, doublet, J=6 Hz); 5.7–5.9 (1H, multiplet); 6.88 (1H, singlet); 9.80 (1H, doublet, J=8 Hz).

EXAMPLE 65

2-Aminoethoxycarbonyloxymethyl 7-[2-(2-aminothiazol-4-yl)-2-(syn-hydroxyimino)acetamido]-3-(3-fluorophenoxy)methyl-3-cephem-4-carboxylate trifluoroacetate 65(a) Allyl 3-(3-fluorophenoxy)methyl-7-[2-(2-tritylaminothiazol-4-yl)-2-(syn-trityloxyimino)acetamido]-3-cephem-4-carboxylate The procedure described in Example 45 was repeated, but using 1.00 g of diphenylmethyl 3-(3-fluorophenoxy)methyl-7-phenoxyacetamido-3-cephem-4-carboxylate [prepared as described in Example 3(a)] and 0.2 ml of allyl bromide to give 310 mg of allyl 7-amino-3-(3-fluorophenoxy)methyl-3-cephem-4-carboxylate hydrochloride. The procedure described in Example 1(b) was then repeated, but using the whole of this product, to afford 474 mg of the title compound in the form of powder.
Nuclear Magnetic Resonance Spectrum (CDCl₃) δ ppm: 3.37 (1H, doublet, J=19 Hz); 3.57 (1H, doublet, J=19 Hz); 4.7–4.8 (2H, multiplet); 4.86 (1H, doublet, J=13 Hz); 5.06 (1H, doublet, J=13 Hz) 5.07 (1H, doublet, J=5 Hz); 5.31 (1H, doublet, J=10 Hz); 5.40 (1H, doublet, J=17 Hz); 5.9–6.1 (2H, multiplet); 6.69 (1H, singlet).

65(b) Sodium 3-(3-fluorophenoxy)methyl-7-[2-(2-tritylaminothiazol-4-yl)-2-(syn-trityloxyimino)acetamido]-3-cephem-4-carboxylate A mixture of 460 mg of allyl 7-[2-(2-tritylaminothiazol-4-yl)-2-(syn-trityloximino)acetamido]-3-(3-fluorophenoxy)methyl-3-cephem-4-carboxylate [prepared as described in step (a) above], 55 mg of tetrakis(triphenylphosphine)palladium and 24 mg of triphenylphosphine in 10 ml of methylene chloride was stirred for 1 hour at room temperature. At the end of this time, the solvent was distilled off under reduced pressure to leave a residue, which was then dissolved in 4 ml of methanol. A solution of 115 mg of sodium 2-ethylhexanoate in 1 ml of methanol was added to the resulting solution, and then the mixture was stirred for 15 minutes. Diisopropyl ether was added to the reaction mixture to give a precipitate, which was collected by filtration to afford 400 mg of the title compound as a powder.
Nuclear Magnetic Resonance Spectrum (hexadeuterated dimethyl sulfoxide) δ ppm: 4.91 (1H, doublet, J=12 Hz); 5.01 (1H, doublet, J=12 Hz); 5.03 (1H, doublet, J=5 Hz); 5.63 (1H, doublet of doublets, J=5 & 8 Hz); 6.58 (1H, singlet); 8.75 (1H, singlet); 9.84 (1H, doublet, J=8 Hz).

65(c) 2-Aminoethoxycarbonyloxymethyl 7-[2-(2-aminothiazol-4-yl)-2-(syn-hydroxyimino)acetamido]-3-(3-fluorophenoxy)methyl-3-cephem-4-carboxylate trifluoroacetate The procedure described in Example 19 was repeated, but using 390 mg of the sodium salt prepared as described in step (b) above and 200 mg of 2-(t-butoxycarbonylamino)ethoxycarbonyloxymethyl iodide, to afford 230 mg of an ester as a powder. A mixture of 220 mg of this ester, 0.2 ml of methylene chloride, 0.4 ml of anisole and 2 ml of trifluoroacetic acid was stirred at room temperature for 2.5 hours. At the end of this time, diisopropyl ether was added to the reaction mixture to give a precipitate, which was collected by filtration, to afford 120 mg of the title compound as a powder.
Nuclear Magnetic Resonance Spectrum (hexadeuterated dimethyl sulfoxide) δ ppm: 3.0–3.2 (2H, multiplet); 4.2–4.4 (2H, multiplet); 4.85 (2H, singlet); 5.24 (1H, doublet, J=5 Hz); 5.8–6.0 (3H, multiplet); 6.70 (1H, singlet); 9.52 (1H, doublet, J=8 Hz); 11.51 (1H, broad singlet).

We claim:

1. A compound of the formula

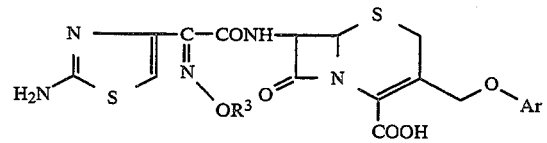

wherein

R³ represents a hydrogen atom or a substituted C₁–C₆ alkyl group having two halogen substituents or one carboxy substituent;

Ar represents a substituted phenyl group having 1 to 3 substituents selected from the group consisting of a substituted C₁–C₆ alkyl group having at least one halogen, hydroxy, or C₂–C₇ alkoxycarbonyl substituent; a C₁–C₆ aliphatic carboxylic acyl group; a C₁–C₆ aliphatic carboxylic acylamino group; a C₂–C₆ alkoxycarbonyl group; a halogen atom; a cyano group; and pharmaceutically acceptable salts and esters thereof.

2. The compound of claim 1, wherein

R³ represents a hydrogen atom, or a methyl group having 2 halogen substituents or having 1 carboxy substituent;

Ar represents a phenyl group having 1 to 3 substituents selected from the group consisting of a substituted C₁–C₂ alkyl group having 1 to 3 halogens, methoxycarbonyl, or hydroxy substituents; an acetylamino group; a C₂–C₃ alkoxycarbonyl group; a halogen atom; a cyano group and pharmaceutically acceptable salts and esters thereof.

3. The compound of claim 1, wherein

R³ represents a hydrogen atom, or a difluoromethyl group;

Ar represents a phenyl group having 1 or 2 substituents selected from the group consisting of a trifluoromethyl group, a 2-hydroxyethyl group, a methoxycarbonylmethyl group, an acetylamino group, a methoxycarbonyl group, an ethoxycarbonyl group, a fluorine atom and a cyano group, and pharmaceutically acceptable salts and esters thereof.

4. The compound of claim 1, wherein R³ is selected from the group consisting of hydrogen, difluoromethyl and carboxymethyl.

5. The compound of claim 4, wherein Ar is selected from the group consisting of 2-fluorophenyl, 3-fluorophenyl, 4-fluorophenyl, 2,4-difluorophenyl, 4-bromophenyl, 4-cyanophenyl, 3,4-difluorophenyl, 3-fluorophenyl, 3-cyanophenyl, 4-acetylphenyl, 2-cyanophenyl, 3-chlorotrifluorophenyl, 4-acetylaminophenyl, 4-methoxycarbonylphenyl and 4-(2-hydroxyethyl)phenyl.

6. A pharmaceutical composition for the treatment of bacterial infections comprising an effective antibacterial amount of the compound of claim 1 or a pharmaceutically acceptable salt or ester thereof, in admixture with a pharmaceutically acceptable carrier.

7. A method of treating an animal suffering from a bacterial infection by administering to said animal an effective antibacterial amount of an antibiotic, wherein the antibiotic is selected from the group consisting of compounds of the formula set forth in claim 1 and pharmaceutically acceptable salts and esters thereof.

8. The composition of claim 6, wherein said antibiotic is a compound as claimed in claim 2.

9. The composition of claim 6, wherein said antibiotic is a compound as claimed in claim 3.

10. The composition of claim 6, wherein said antibiotic is a compound as claimed in claim 4.

11. The composition of claim 6, wherein said antibiotic is a compound as claimed in claim 5.

12. The composition of claim 6, wherein said antibiotic is selected from the group consisting of:

7-[2-(2-aminothiazol-4-yl)-2-(syn-hydroxyimino)acetamido]-3-(3-fluorophenoxy)methyl-3-cephem-4-carboxylic acid;

7-[2-(2-aminothiazol-4-yl)-2-(syn-hydroxyimino)acetamido]-3-(3,4-difluorophenoxy)methyl-3-cephem-4-carboxylic acid;

7-[2-(2-aminothiazol-4-yl)-2-(syn-hydroxyimino)acetamido]-3-(3-cyanophenoxy)methyl-3-cephem-4-carboxylic acid;

7-[2-(2-aminothiazol-4-yl)-2-(syn-hydroxyimino)acetamido]-3-(4-acetylphenoxy)methyl-3-cephem-4-carboxylic acid;

7-[2-(2-aminothiazol-4-yl)-2-(syn-hydroxyimino)acetamido]-3-(4-acetyl-3-hydroxyphenoxy)methyl-3-cephem-4-carboxylic acid;

7-[2-(2-aminothiazol-4-yl)-2-(syn-hydroxyimino)acetamido]-3-(4-acetamidophenoxy)methyl-3-cephem-4-carboxylic acid; and pharmaceutically acceptable salts and esters thereof.

13. The method of claim 7, wherein said antibiotic is selected from the group consisting of:

7-[2-(2-aminothiazol-4-yl)-2-(syn-hydroxyimino)acetamido]-3-(3-fluorophenoxy)methyl-3-cephem-4-carboxylic acid;

7-[2-(2-aminothiazol-4-yl)-2-(syn-hydroxyimino)acetamido] -3-(3,4-difluorophenoxy)methyl-3-cephem-4-carboxylic acid;

7-[2-(2-aminothiazol-4-yl)-2-(syn-hydroxyimino)acetamido]-3-(3-cyanophenoxy)methyl-3-cephem-4-carboxylic acid;

7-[2-(2-aminothiazol-4-yl)-2-(syn-hydroxyimino)acetamido]-3-(4-acetylphenoxy)methyl-3-cephem-4-carboxylic acid;

7-[2-(2-aminothiazol-4-yl)-2-(syn-hydroxyimino)acetamido]-3-(4-acetyl-3-hydroxyphenoxy)methyl-3-cephem-4-carboxylic acid;

7-[2-(2-aminothiazol-4-yl)-2-(syn-hydroxyimino)acetamido]-3-(4-acetamidophenoxy)methyl-3-cephem-4-carboxylic acid; and pharmaceutically acceptable salts and esters thereof.

14. The method of claim 7, in which said bacterial infection is caused by a Methicillin-resistant strain of Staphylococcus.

15. The method of claim 13, in which said bacterial infection is caused by a Methicillin-resistant strain of Staphylococcus.

16. The compound of claim 1, selected from the group consisting of 7-[2-(2-aminothiazol-4-yl)-2-(syn-hydroxyimino)acetamido]-3-(3-fluorophenoxy)methyl-3-cephem-4-carboxylic acid and pharmaceutically acceptable salts and esters thereof.

17. The compound of claim 1, selected from the group consisting of 7-[2-(2-aminothiazol-4-yl)-2-(syn-hydroxyimino)acetamido]-3-(3,4-difluorophenoxy)-methyl-3-cephem-4-carboxylic acid and pharmaceutically acceptable salts and esters thereof.

18. The compound of claim 1, selected from the group consisting of 7-[2-(2-aminothiazol-4-yl)-2-(syn-hydroxyimino)acetamido]-3-(3-cyanophenoxy)methyl-3-cephem-4-carboxylic acid and pharmaceutically acceptable salts and esters thereof.

19. The compound of claim 1, selected from the group consisting of 7-[2-(2-aminothiazol-4-yl)-2-(syn-hydroxyimino)acetamido]-3-(4-acetylphenoxy)methyl-3-cephem-4-carboxylic acid and pharmaceutically acceptable salts and esters thereof.

20. The compound of claim 1, selected from the group consisting of 7-[2-(2-aminothiazol-4-yl)-2-(syn-hydroxyimino)acetamido] -3-(4-acetyl-3-hydroxyphenoxy)methyl-3-cephem-4-carboxylic acid and pharmaceutically acceptable salts and esters thereof.

21. The compound of claim 1, selected from the group consisting of 7-[2-(2-aminothiazol-4-yl)-2-(syn-hydroxyimino)acetamido]-3-(4-acetamidophenoxy)-methyl-3-cephem-4-carboxylic acid and pharmaceutically acceptable salts and esters thereof.

* * * * *